US012595286B2

(12) United States Patent
Hayashi et al.

(10) Patent No.:     US 12,595,286 B2
(45) Date of Patent:          Apr. 7, 2026

(54) FUCOSE-BINDING PROTEIN, METHOD FOR PRODUCING SAME, AND USE OF SAME

(71) Applicants: TOSOH CORPORATION, Yamaguchi (JP); SAGAMI CHEMICAL RESEARCH INSTITUTE, Kanagawa (JP)

(72) Inventors: Masahiro Hayashi, Kanagawa (JP); Takahiro Maruyama, Kanagawa (JP); Hiroyuki Ito, Kanagawa (JP); Aya Asagoshi, Kanagawa (JP); Kouta Hatayama, Kanagawa (JP); Megumi Hoya, Kanagawa (JP)

(73) Assignees: TOSOH CORPORATION, Yamaguchi (JP); SAGAMI CHEMICAL RESEARCH INSTITUTE, Kanagawa (JP)

( * ) Notice: Subject to any disclaimer, the term of this patent is extended or adjusted under 35 U.S.C. 154(b) by 1317 days.

(21) Appl. No.: 17/267,891

(22) PCT Filed: Aug. 8, 2019

(86) PCT No.: PCT/JP2019/031402
§ 371 (c)(1),
(2) Date: May 10, 2021

(87) PCT Pub. No.: WO2020/036118
PCT Pub. Date: Feb. 20, 2020

(65)          Prior Publication Data
US 2021/0261629 A1     Aug. 26, 2021

(30)          Foreign Application Priority Data
Aug. 13, 2018     (JP) ................................. 2018-152361

(51) Int. Cl.
| | |
|---|---|
| *A61K 38/00* | (2006.01) |
| *B01D 15/38* | (2006.01) |
| *B01J 20/24* | (2006.01) |
| *B01J 20/30* | (2006.01) |
| *C07H 1/06* | (2006.01) |
| *C07K 14/195* | (2006.01) |
| *C12N 5/09* | (2010.01) |

(52) U.S. Cl.
CPC ........ *C07K 14/195* (2013.01); *B01D 15/3823* (2013.01); *B01J 20/24* (2013.01); *B01J 20/30* (2013.01); *C07H 1/06* (2013.01); *C12N 5/0693* (2013.01)

(58) Field of Classification Search
CPC ..... B01D 15/3823; B01J 20/24; B01J 20/286; B01J 20/30; B01J 20/3219; B01J 20/3274; B01J 2220/58; C07H 1/06; C07K 14/195; C07K 17/08; C12N 15/70; C12N 5/0693
See application file for complete search history.

(56)          References Cited

U.S. PATENT DOCUMENTS

| | | | |
|---|---|---|---|
| 2013/0079499 A1 | 3/2013 | Hatayama et al. | |
| 2015/0111218 A1* | 4/2015 | Tateno ............. | G01N 33/56966 |
| | | | 435/7.1 |
| 2015/0204870 A1 | 7/2015 | Tateno et al. | |
| 2018/0250360 A1 | 9/2018 | Tateno et al. | |

FOREIGN PATENT DOCUMENTS

| | | |
|---|---|---|
| JP | 2001-103973 | 4/2001 |
| JP | 2006-25659 | 2/2006 |
| JP | 2011-206046 | 10/2011 |
| JP | 2018-38 | 1/2018 |
| JP | 2018000038 A  * | 1/2018 |
| WO | 2013/065302 | 5/2013 |

(Continued)

OTHER PUBLICATIONS

English language translation of JP-2018000038-A provided by Espacenet (Year: 2018).*
EESR issued in corresponding EP Application No. 19850701.4, dated May 9, 2022.
Tateno, H. et al., "Podocalyxin Is a Glycoprotein Ligand of the Human Pluripotent Stem Cell-Specific Probe rBC2LCN", Stem Cells Transl Med, Mar. 22, 2013, vol. 2, pp. 265-273.
Sulak, O. et al., "A TNF-like Trimeric Lectin Domain from Burkholderia cenocepacia with Specificity for Fucosylated Human Histo-Blood Group Antigens", Structure, Jan. 13, 2010, vol. 18, pp. 59-72.
Tateno, H. et al., "Glycome Diagnosis of Human Induced Pluripotent Stem Cells Using Lectin Microarray", The Journal of Biological Chemistry, vol. 286, Jun. 10, 2011, pp. 20345-20353.

(Continued)

*Primary Examiner* — Lianko G Garyu
*Assistant Examiner* — Mercy H Sabila
(74) *Attorney, Agent, or Firm* — GREENBLUM & BERNSTEIN, P.L.C.

(57)          ABSTRACT
The present invention aims to provide a fucose-binding protein that shows improved productivity in cases of expression in a host such as *Escherichia coli*, improved binding affinity to a fucose-containing sugar chain such as a sugar chain containing a structure composed of Fucα1-2Galβ1-3GlcNAc and/or Fucα1-2Galβ1-3GalNAc, and/or improved thermal stability. The above object is achieved by deleting a plurality of amino acid residues in the C-terminal side of the amino acid sequence of the fucose-binding protein BC2LCN of SEQ ID NO: 1, and, when necessary, substituting the glycine residue at position 36 in SEQ ID NO: 1 with a cysteine residue, substituting the glutamine residue at position 39 in SEQ ID NO: 1 with a leucine residue or methionine residue, substituting the glutamine residue at position 65 in SEQ ID NO: 1 with a leucine residue, substituting the cysteine residue at position 72 in SEQ ID NO: 1 with a glycine residue or alanine residue, substituting the glutamic acid residue at position 81 in SEQ ID NO: 1 with a cysteine residue, glutamine residue, histidine residue, or methionine residue, and/or substituting the glycine residue identified as the residue at position 36 in SEQ ID NO: 1 with a cysteine residue.

23 Claims, 2 Drawing Sheets
Specification includes a Sequence Listing.

(56)          References Cited

FOREIGN PATENT DOCUMENTS

WO       2013/128914       9/2013
WO       2017/061449 A1    4/2017

OTHER PUBLICATIONS

Tang, C. et al., "An antibody against SSEA-5 glycan on human pluriptoent stem cells enables removal of teratoma-forming cells", Nature Biotechnology, 2011, vol. 29, pp. 829-834.
International Search Report issued in International Patent Application No. PCT/JP2019/031402, dated Nov. 5, 2019.

* cited by examiner

[Fig. 1]
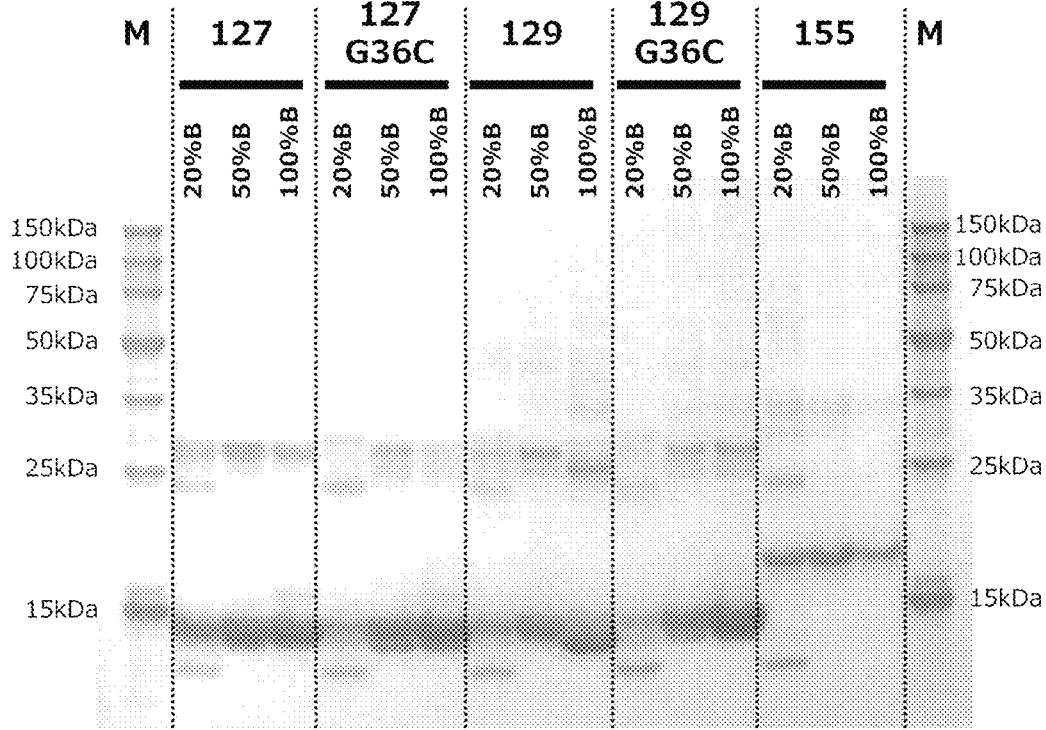
127        : Fucose-binding protein 127
127G36C : Fucose-binding protein 127G36C
129        : Fucose-binding protein 129
129G36C : Fucose-binding protein 129G36C
155        : Recombinant BC2LCN(155)cys
20%B    : 20% B eluted fraction in nickel chelate chromatography
50%B    : 50% B eluted fraction in nickel chelate chromatography
100%B   : 100% B eluted fraction in nickel chelate chromatography

[Fig. 2]
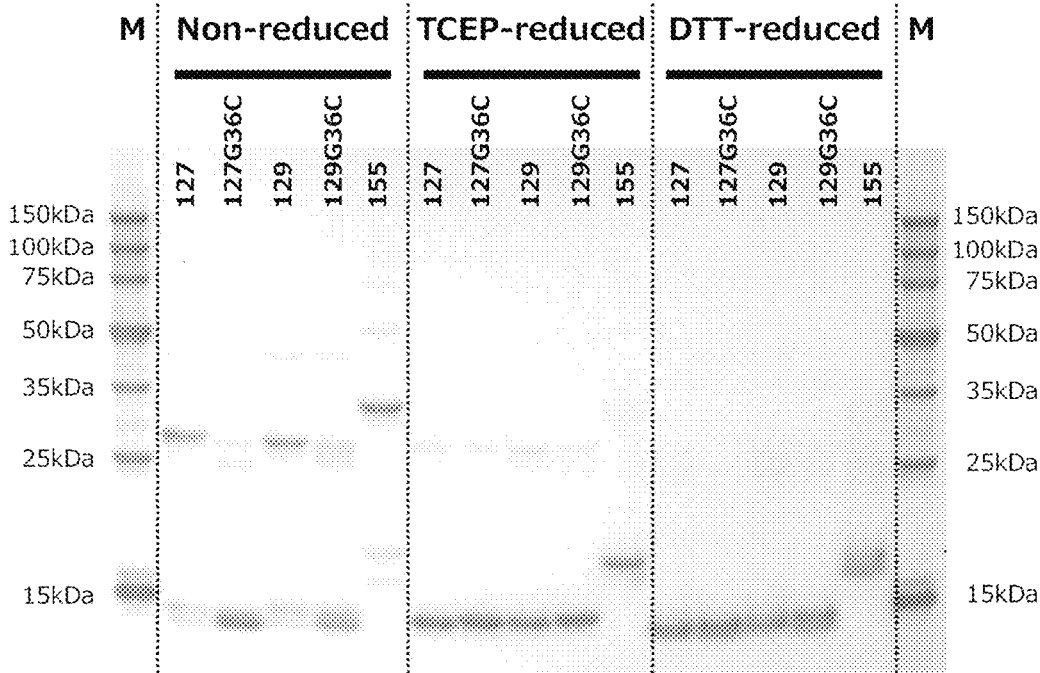
127         : Purified 127 solution
127G36C : Purified 127G36C solution
129         : Purified 129 solution
129G36C : Purified 129G36C solution
155         : Purified BC2LCN(155) solution
Non-reduced   : Non-reduced sample solution in Reference Example 1
TCEP-reduced  : TCEP-reduced sample solution in Reference Example 1
DTT-reduced   : DTT-reduced sample solution in Reference Example 1

FUCOSE-BINDING PROTEIN, METHOD FOR PRODUCING SAME, AND USE OF SAME

SEQUENCE LISTING

The instant application contains a Sequence Listing which has been submitted electronically in ASCII format and is hereby incorporated by reference in its entirety. Said ASCII copy, created on May 10, 2021, is named 02_OP-19264-PCT_Eng_seq_ver01 (04796709).TXT and is 58,002 bytes in size.

TECHNICAL FIELD

The present invention relates to a fucose-binding protein, a production method therefor, and a use thereof. The present invention may be related especially to a fucose-binding protein that shows improved productivity in cases of expression in a host such as *Escherichia coli*, improved binding affinity to a fucose-containing sugar chain such as a sugar chain containing a structure composed of Fucα1-2Galβ1-3GlcNAc and/or Fucα1-2Galβ1-3GalNAc, and/or improved thermal stability.

BACKGROUND ART

BC2LCN, derived from the N-terminal domain of BC2L-C lectin produced by a gram-negative bacterium (*Burkholderia cenocepacia*), is a protein having binding affinities to sugar chains containing a fucose residue. For example, BC2LCN is known to have high binding affinities not only to H type 1 sugar chain (Fucα1-2Galβ1-3GlcNAc) and H type 3 sugar chain (Fucα1-2Galβ1-3GalNAc), which are known to be undifferentiation sugar chain markers as described in Non-patent Document 1, Patent Document 1, and Patent Document 2, but also to a plurality of kinds of sugar chains containing a fucose residue, including Lewis Y sugar chain (Fucα1-2Galβ1-4 (Fucα1-3) GlcNAc) and Lewis X sugar chain (Galβ1-4 (Fucα1-3) GlcNAc) (Non-patent Document 2). It is also known that, while BC2LCN binds to human iPS cells and human ES cells in the undifferentiated state showing high expression of H type 1 sugar chain and H type 3 sugar chain, it does not bind to human somatic cells (Non-patent Document 3). Further, since BC2LCN has the binding capacity to the undifferentiation sugar chain markers described above, it is used for, for example, detection of glycoconjugates containing an undifferentiation sugar chain marker, and detection of undifferentiated cells such as human iPS cells or human ES cells (Patent Document 1 and Patent Document 2). Further, H type 1 sugar chain is known to be highly expressed as SSEA-5 in particular cancer cells (Non-patent Document 4). BC2LCN has an ability to detect undifferentiated stem cells, and the ability is equivalent to those of known antibodies for detection of undifferentiated cells, such as anti-Nanog antibodies (Patent Document 2). However, binding of BC2LCN to a sugar chain of undifferentiated cells is dependent on electrostatic interaction, and the binding strength is affected by the external environment such as the solvent and the salt concentration. Therefore, in detection of the undifferentiated cells and/or glycoconjugates containing the undifferentiation sugar chain marker, the binding affinity of the sugar chain to BC2LCN may be low depending on experimental conditions, so that BC2LCN having improved binding affinity to the undifferentiation sugar chain marker has been demanded.

In a known method for improving a function of a protein, amino acid mutation is introduced to the protein by a protein engineering method, to thereby improve the desired function. For example, Patent Document 3 describes an Fc-binding protein having improved stability against heat, acid, and/or alkali due to substitution of a particular amino acid residue(s) with another/other amino acid residue(s). However, there has so far been no report on BC2LCN having improved thermal stability and/or binding affinity to sugar chains due to amino acid substitution at a particular position(s). Further, for industrial application of BC2LCN, from the viewpoint of stable supply and large-scale supply, productivity in the case of production using a microorganism such as *Escherichia coli* is preferably high. However, there has so far been no report on BC2LCN having improved productivity.

PRIOR ART DOCUMENTS

Patent Documents

Patent Document 1: WO 2013/065302
Patent Document 2: WO 2013/128914
Patent Document 3: JP 2011-206046 A

Non-Patent Documents

Non-patent Document 1: Tateno, H et al., Stem Cells Transl Med. 2013, 2 (4): 265-273.
Non-patent Document 2: Sulak, O et al., Structure. 2010, 18 (1): 59-72.
Non-patent Document 3: Tateno, H et al., J Biol Chem. 2011, 286 (23): 20345-20353.
Non-patent Document 4: Tang, C, Nat Biotechnol. 2011, 29 (9): 829-835

SUMMARY OF THE INVENTION

Problems to be Solved by the Invention

An object of the present invention is to provide a fucose-binding protein having excellent properties. More specifically, an object of the present invention may be to provide a fucose-binding protein that shows improved productivity in cases of expression in a host such as *Escherichia coli*, improved binding affinity to a fucose-containing sugar chain such as a sugar chain containing a structure composed of Fucα1-2Galβ1-3GlcNAc and/or Fucα1-2Galβ1-3GalNAc, and/or improved thermal stability.

Means for Solving the Problems

As a result of intensive study to solve the above problem, the present inventors discovered that, by deleting a plurality of amino acid residues in the C-terminal side of the amino acid sequence of BC2LCN composed of the 155 amino acid residues of SEQ ID NO: 1, productivity in cases of expression in *Escherichia coli* can be remarkably improved. The present inventors also discovered that, by substituting the glutamine residue at position 39 in the amino acid sequence of SEQ ID NO: 1 with a leucine residue or a methionine residue, and/or substituting the glutamine residue at position 65 in the amino acid sequence of SEQ ID NO: 1 with a leucine residue, and/or substituting the cysteine residue at position 72 in the amino acid sequence of SEQ ID NO: 1 with a glycine residue or an alanine residue, a fucose-binding protein having improved thermal stability can be obtained. The present inventors also discovered that, by substituting the glutamic acid residue at position 81 in the amino acid sequence of SEQ ID NO: 1 with a cysteine residue, a glutamine residue, a histidine residue, a methionine residue, a valine residue, a lysine residue, a serine residue, an isoleucine residue, a tyrosine residue, a glycine residue, a proline residue, a leucine residue, or an asparagine residue, a fucose-binding protein having improved binding affinity to a sugar chain containing a structure composed of Fucα1-2Galβ1-3GlcNAc and/or Fucα1-2Galβ1-3GalNAc can be obtained. The present inventors also discovered that substitution of the glycine residue at position 36 in the amino acid sequence of SEQ ID NO: 1 with a cysteine residue suppresses generation of a dimer due to disulfide bond formation that occurs when an oligopeptide containing one or more cysteine residues is added to the C-terminus in the production. The present inventors completed the present invention based on these discoveries.

More specifically, the present invention includes, for example, the inventions described in the following [1] to [24].

[1] A fucose-binding protein comprising an amino acid sequence described in any of the following (a) to (d):

(a) the amino acid sequence from the proline residue at position 1 to the amino acid residue at position X in the amino acid sequence of SEQ ID NO: 1, wherein X is an integer of 110 to 140;

(b) an amino acid sequence which is the same as the amino acid sequence from the proline residue at position 1 to the amino acid residue at position X in the amino acid sequence of SEQ ID NO: 1 except that the above amino acid sequence contains deletion, substitution, insertion, and/or addition of one or more amino acid residues, wherein X is an integer of 110 to 140;

(c) an amino acid sequence having a homology of not less than 90% to the amino acid sequence from the proline residue at position 1 to the amino acid residue at position X in the amino acid sequence of SEQ ID NO: 1, wherein X is an integer of 110 to 140; and (d) an amino acid sequence which is the same as the amino acid sequence described in any of the (a) to (c) except that the above amino acid sequence contains a particular amino acid substitution, wherein the particular amino acid substitution is one or more amino acid substitutions selected from the amino acid substitutions described in the following (1) to (5):

(1) substitution of the amino acid residue corresponding to the glutamine residue at position 39 in the amino acid sequence of SEQ ID NO: 1, with an amino acid residue other than a glutamine residue;

(2) substitution of the amino acid residue corresponding to the cysteine residue at position 72 in the amino acid sequence of SEQ ID NO: 1, with an amino acid residue other than a cysteine residue;

(3) substitution of the amino acid residue corresponding to the glutamine residue at position 65 in the amino acid sequence of SEQ ID NO: 1, with an amino acid residue other than a glutamine residue;

(4) substitution of the amino acid residue corresponding to the glutamic acid residue at position 81 in the amino acid sequence of SEQ ID NO: 1, with an amino acid residue other than a glutamic acid residue; and (5) substitution of the amino acid residue corresponding to the glycine residue at position 36 in the amino acid sequence of SEQ ID NO: 1, with an amino acid residue other than a glycine residue;

wherein the fucose-binding protein has binding affinity to a sugar chain containing a structure composed of Fucα1-2Galβ1-3GlcNAc and/or a sugar chain containing a structure composed of Fucα1-2Galβ1-3GalNAc, provided that the fucose-binding protein is not a protein containing the amino acid sequence of SEQ ID NO: 1.

[2] The fucose-binding protein according to [1], wherein the amino acid substitutions described in (1) to (5) are the amino acid substitutions described in the following (6) to (10), respectively:

(6) substitution of the amino acid residue corresponding to the glutamine residue at position 39 in the amino acid sequence of SEQ ID NO: 1, with a leucine residue or a methionine residue;

(7) substitution of the amino acid residue corresponding to the cysteine residue at position 72 in the amino acid sequence of SEQ ID NO: 1, with a glycine residue or an alanine residue;

(8) substitution of the amino acid residue corresponding to the glutamine residue at position 65 in the amino acid sequence of SEQ ID NO: 1, with a leucine residue;

(9) substitution of the amino acid residue corresponding to the glutamic acid residue at position 81 in the amino acid sequence of SEQ ID NO: 1, with a cysteine residue, a glutamine residue, a histidine residue, a methionine residue, a valine residue, a lysine residue, a serine residue, an isoleucine residue, a tyrosine residue, a glycine residue, a proline residue, a leucine residue, or an asparagine residue; and

(10) substitution of the amino acid residue corresponding to the glycine residue at position 36 in the amino acid sequence of SEQ ID NO: 1, with a cysteine residue.

[3] The fucose-binding protein according to [1] or [2], having a total length of 95 to 175 residues.

[4] The fucose-binding protein according to any one of [1] to [3], wherein the length of the amino acid sequence described in each of (a) to (d) is 95 to 155 residues.

[5] The fucose-binding protein according to any one of [1] to [4], comprising the amino acid sequence of any of SEQ ID NO: 2 to SEQ ID NO: 16.

[6] The fucose-binding protein according to any one of [1] to [5], comprising an additional amino acid sequence(s) at the N-terminus and/or C-terminus.

[7] The fucose-binding protein according to any one of [1] to [6], wherein the amino acid sequence added to the C-terminus is an oligopeptide containing a cysteine residue.

[8] The fucose-binding protein according to any one of [1] to [7], wherein the amino acid sequence added to the N-terminus is an oligopeptide containing a polyhistidine sequence.

[9] A DNA encoding the fucose-binding protein according to any one of [1] to [8].

[10] An expression vector comprising the DNA according to [9].

[11] A transformant comprising the DNA according to [9] or the expression vector according to [10].

[12] The transformant according to [11], which is *Escherichia coli*.

[13] A method of producing a fucose-binding protein, the method comprising the steps of:

culturing the transformant according to or to allow expression of the fucose-binding protein; and collecting the expressed fucose-binding protein;

wherein the fucose-binding protein is the fucose-binding protein according to any one of [1] to [8].

[14] An adsorbent comprising:

an insoluble carrier; and the fucose-binding protein according to any one of [1] to [8], wherein the fucose-binding protein is immobilized on the insoluble carrier.

[15] A method of producing an adsorbent, the method comprising the steps of:

producing a reactive insoluble carrier from an insoluble carrier; and immobilizing the fucose-binding protein according to any one of [1] to [8] on the reactive insoluble carrier;

wherein the adsorbent is the adsorbent according to [14].

[16] The method according to [15], wherein the reactive insoluble carrier is an insoluble carrier comprising a maleimide group or a haloacetyl group.

[17] A column packed with the adsorbent according to [14].

[18] A method of separating cells, the method comprising the steps of:

bringing the adsorbent according to into contact with a cell mixture; and separating cells adsorbed on the adsorbent, from cells not adsorbed on the adsorbent.

[19] The method according to [18], wherein the cell mixture is a mixture containing first cells and second cells, wherein the first cells are each a cell containing a sugar chain containing a structure composed of Fucα1-2Galβ1-3GlcNAc and/or a sugar chain containing a structure composed of Fucα1-2Galβ1-3GalNAc; and wherein the second cells are each a cell containing neither a sugar chain containing a structure composed of Fucα1-2Galβ1-3GlcNAc nor a sugar chain containing a structure composed of Fucα1-2Galβ1-3GalNAc.

[20] The method according to or [19], wherein the first cells are each an undifferentiated cell, and the second cells are each a differentiated cell.

[21] The method according to or [19], wherein the first cells are each a cancer cell.

[22] A method of purifying a substance containing a fucose-containing sugar chain, the method comprising the steps of:

bringing the adsorbent according to into contact with the substance containing the fucose-containing sugar chain; and eluting the substance bound to the adsorbent, wherein the fucose-containing sugar chain is a sugar chain containing a structure composed of Fucα1-2Galβ1-3GlcNAc and/or a sugar chain containing a structure composed of Fucα1-2Galβ1-3GalNAc;

[23] The method according to [22], wherein the substance is the fucose-containing sugar chain and/or glycoconjugates containing the fucose-containing sugar chain.

[24] The method according to any one of to [23], wherein the column according to is used.

BRIEF DESCRIPTION OF THE DRAWINGS

FIG. 1 shows the results (a photograph) of analysis of the fucose-binding protein 129 in Example 1, the fucose-binding protein 127 in Example 2, the fucose-binding protein 129G36C in Example 3, the fucose-binding protein 127G36C in Example 4, and the recombinant BC2LCN (155)cys in Comparative Example 1, which analysis was carried out by the SDS-PAGE method under reducing conditions.

FIG. 2 shows the results (a photograph) of analysis of the purified 129 solution, purified 127 solution, purified 129G36C solution, purified 127G36C solution, and purified BC2LCN(155) solution in Example 5, which analysis was carried out by the SDS-PAGE method under non-reducing conditions and reducing conditions.

MODE FOR CARRYING OUT THE INVENTION

The present invention is described below in detail.

The fucose-binding protein of the present invention is a particular fucose-binding protein. The "fucose-binding protein" means a protein having binding capacity to a fucose-containing sugar chain. The "binding capacity" is also referred to as "binding affinity". Thus, the fucose-binding protein of the present invention has binding affinity to a fucose-containing sugar chain. The "fucose-containing sugar chain" means a sugar chain containing a fucose residue. The structure of the fucose-containing sugar chain (for example, the length of the fucose-containing sugar chain, the number and positions of fucose residues, and the types, number, and positions of sugar residues other than fucose residues) is not limited as long as the fucose-containing sugar chain contains a fucose residue. Examples of the fucose-containing sugar chain include sugar chains comprising a sugar chain structure containing a fucose residue, such as a structure composed of Fucα1-2Galβ1-3GlcNAc, a structure composed of Fucα1-2Galβ1-3GalNAc, a structure composed of Fucα1-2Galβ1-3 (Fucα1-4) GlcNAc, a structure composed of Galβ1-4 (Fucα1-3) GlcNAc, and a structure composed of Fucα1-2Galβ1-4 (Fucα1-3) GlcNAc. The sugar chains comprising these sugar chain structures may be sugar chains composed of these respective sugar chain structures. The structure composed of Fucα1-2Galβ1-3GlcNAc is also referred to as "H type 1 sugar chain structure"; the structure composed of Fucα1-2Galβ1-3GalNAc is also referred to as "H type 3 sugar chain structure"; the structure composed of Fucα1-2Galβ1-4 (Fucα1-3) GlcNAc is also referred to as "Lewis Y sugar chain structure"; and the structure composed of Fucα1-2Galβ1-3 (Fucα1-4) GlcNAc is also referred to as "Lewis b sugar chain structure". The sugar chain composed of Fucα1-2Galβ1-3GlcNAc (H type 1 sugar chain structure) is also referred to as "H type 1 sugar chain"; the sugar chain composed of Fucα1-2Galβ1-3GalNAc (H type 3 sugar chain structure) is also referred to as "H type 3 sugar chain"; the sugar chain composed of Fucα1-2Galβ1-4 (Fucα1-3) GlcNAc (Lewis Y sugar chain structure) is also referred to as "Lewis Y sugar chain"; and the sugar chain composed of Fucα1-2Galβ1-3 (Fucα1-4) GlcNAc (Lewis b sugar chain structure) is also referred to as "Lewis b sugar chain". The fucose-binding protein of the present invention may have, for example, binding affinity to one or more kinds of fucose-containing sugar chains selected from these fucose-containing sugar chains. The fucose-binding protein of the present invention may have binding affinity especially to at least a sugar chain containing a structure composed of Fucα1-2Galβ1-3GlcNAc and/or Fucα1-2Galβ1-3GalNAc. The "sugar chain containing a structure composed of Fucα1-2Galβ1-3GlcNAc and/or Fucα1-2Galβ1-3GalNAc" may mean a sugar chain containing a structure composed of Fucα1-2Galβ1-3GlcNAc (H type 1 sugar chain structure) and/or a sugar chain containing a structure composed of Fucα1-2Galβ1-3GalNAc (H type 3 sugar chain structure).

Binding affinity of a protein to a sugar chain can be evaluated by, for example, the ELISA (enzyme-linked immunosorbent assay) method or the surface plasmon resonance method. For example, evaluation of the binding affinity by the surface plasmon resonance method is as described below. Measurement for the evaluation of the binding affinity by the surface plasmon resonance method may be carried out by, for example, using a Biacore T200 apparatus (manufactured by GE Healthcare), wherein the protein is used as an analyte, and wherein the sugar chain is used as a solid phase. A sensor chip on which the sugar chain is immobilized can be obtained by, for example, binding a biotin-labeled sugar chain to a streptavidin-coated sensor chip (Sensor Chip SA, manufactured by GE Healthcare), or to a dextran-coated sensor chip (Sensor Chip CM5, manufactured by GE Healthcare) on which streptavidin is immobilized. The binding affinity can be evaluated based on the measured data by using, for example, a kinetics analysis program attached to the apparatus.

Examples of the fucose-binding protein of the present invention include proteins containing the same amino acid sequence as the amino acid sequence of BC2LCN except that the C-terminal region is deleted. The same amino acid sequence as the amino acid sequence of BC2LCN except that the C-terminal region is deleted is also referred to as "short-type BC2LCN sequence". The deleted amino acid sequence in the C-terminal region is also referred to as "deleted sequence".

BC2LCN is a lectin having binding affinity to fucose-containing sugar chains such as H type 1 sugar chain, H type 3 sugar chain, Lewis Y sugar chain, and Lewis b sugar chain. The amino acid sequence of BC2LCN is shown in SEQ ID NO: 1. The amino acid sequence shown as SEQ ID NO: 1 is composed of 155 amino acid residues, and the same as the amino acid sequence from position 2 to position 156 in the amino acid sequence deposited in GenPept under the accession number WP_006490828. As described later in Examples, by deleting the C-terminal region of the amino acid sequence of BC2LCN, the productivity (more specifically, the expression level) in cases of production of BC2LCN using *Escherichia coli* as a host can be improved compared to cases where the C-terminal region is not deleted. Thus, the protein of the present invention shows improved productivity in cases of expression in a host such as *Escherichia coli*, compared to proteins containing the amino acid sequence of SEQ ID NO: 1 such as BC2LCN (155)cys. The protein of the present invention may show improved productivity at least in cases of expression in *Escherichia coli*, compared to proteins containing the amino acid sequence of SEQ ID NO: 1 such as BC2LCN(155)cys. Examples of the improvement of productivity include an increase in the amount of production per unit volume of culture broth, and an increase in the amount of production per host cell.

Thus, the "short-type BC2LCN sequence" means the same amino acid sequence as the amino acid sequence of SEQ ID NO: 1 except that the C-terminal region is deleted. The "short-type BC2LCN sequence", more specifically, means the amino acid sequence from the proline residue at position 1 to the amino acid residue at position X in the amino acid sequence of SEQ ID NO: 1, wherein X is an integer of less than 155. The "deleted sequence", more specifically, means an amino acid sequence from the amino acid residue at position X+1 to the glycine residue at position 155 in the amino acid sequence of SEQ ID NO: 1. X is not limited as long as the fucose-binding protein of the present invention has binding affinity to a fucose-containing sugar chain, and as long as the productivity in cases of expression in a host such as *Escherichia coli* is improved. For example, X may be not less than 110, not less than 115, not less than 120, or not less than 125, may be less than 155, not more than 150, not more than 145, not more than 140, not more than 135, or not more than 130, or may be within a range defined by their combination. In particular, X may be not less than 110, not less than 115, not less than 120, or not less than 125, may be not more than 140, not more than 135, or not more than 130, or may be within a range defined by their combination. More specifically, X may be, for example, an integer of 110 to 140, preferably an integer of 120 to 135, more preferably an integer of 125 to 130.

Specific examples of the short-type BC2LCN sequence include the amino acid sequences of SEQ ID NO: 2, SEQ ID NO: 3, and SEQ ID NO: 6. The amino acid sequence of SEQ ID NO: 2 is the same as the amino acid sequence from position 2 to position 130 in the amino acid sequence deposited in GenPept under the accession number WP_006490828, and this sequence corresponds to the short-type BC2LCN sequence wherein X is 129. The amino acid sequence of SEQ ID NO: 3 is the same as the amino acid sequence from position 2 to position 128 in the amino acid sequence deposited in GenPept under the accession number WP_006490828, and this sequence corresponds to the short-type BC2LCN sequence wherein X is 127. The amino acid sequence of SEQ ID NO: 6 is the same as the amino acid sequence from position 2 to position 127 in the amino acid sequence deposited in GenPept under the accession number WP_006490828, and this sequence corresponds to the short-type BC2LCN sequence wherein X is 126.

Examples of the fucose-binding protein of the present invention also include proteins containing a variant sequence of a short-type BC2LCN sequence. The variant sequence is not limited as long as the fucose-binding protein of the present invention has binding affinity to a fucose-containing sugar chain, and as long as the improvement in the productivity in cases of expression in a host such as *Escherichia coli* is not deteriorated.

Examples of the variant sequence include an amino acid sequence which is the same as a short-type BC2LCN sequence except that the variant sequence contains substitution, deletion, insertion, and/or addition of one or several amino acid residues at one or more positions. The meaning of the term "one or more" may vary depending on the position(s) of the amino acid residue(s) in the spatial structure of the protein, and on the type(s) of the amino acid residue(s). It may mean, for example, 1 to 15, 1 to 12, 1 to 10, 1 to 9, 1 to 8, 1 to 7, 1 to 6, 1 to 5, 1 to 4, 1 to 3, 1 to 2, or 1. Examples of the substitution of the amino acid residue(s) include conservative substitutions, in which substitution occurs between amino acid residues having similar physical properties and/or chemical properties. It is known to those skilled in the art that, in cases of conservative substitution, the protein function is generally maintained between a protein in which the substitution has occurred and a protein in which the substitution has not occurred. Examples of the amino acid residues having similar physical properties and/or chemical properties include amino acid residues whose side chains have similar properties. Examples of the amino acid residues whose side chains have similar properties include a group of amino acid residues having hydrophobic side chains (such as a glycine residue, an alanine residue, a valine residue, a leucine residue, an isoleucine residue, a proline residue, a phenylalanine residue, a methionine residue, and a tryptophan residue), a group of amino acid residues having hydrophilic, acidic side chains (such as an aspartic acid residue and a glutamic acid residue), a group of amino acid residues having hydrophilic, basic side chains (such as a lysine residue, an arginine residue, and a histidine residue), and a group of amino acid residues having hydrophilic, uncharged side chains (such as an asparagine residue, a glutamine residue, a serine residue, a threonine residue, a cysteine residue, and a tyrosine residue). Thus, it can be considered that the amino acid residues in each group have side chains whose properties are similar to each other. Examples of the substitution, deletion, insertion, and/or addition of the amino acid residue(s) also include those generated by naturally occurring mutations (mutants or variants), such as those based on a difference between individuals or species of the organism from which the protein or a gene encoding it is derived.

Examples of the variant sequence also include amino acid sequences having high homology to a short-type BC2LCN sequence. "Homology to an amino acid sequence" means homology to the entire amino acid sequence. "High homology" may mean a homology of, for example, not less than 70%, not less than 75%, not less than 80%, not less than 85%, not less than 90%, or not less than 95%. "Homology" may mean either identity or similarity. "Identity" between amino acid sequences means the ratio of amino acid residues that are of the same kind in the amino acid sequences (Experimental Medicine, February 2013, Vol. 31, No. 3, Yodosha Co., Ltd.). "Similarity" between amino acid sequences means the total of the ratio of amino acid residues that are of the same kind and the ratio of amino acid residues whose side chains have similar properties in the amino acid sequences (Experimental Medicine, February 2013, Vol. 31, No. 3, Yodosha Co., Ltd.). The amino acid residues whose side chains have similar properties are as described above. Homology between amino acid sequences can be determined using an alignment program such as BLAST or FASTA.

In cases where amino acid sequence modification that causes the difference between a short-type BC2LCN sequence and its variant sequence (for example, the addition and/or the like of one or several amino acid residues, or amino acid sequence modification within the above-described range of homology) includes addition of an amino acid residue(s) to the C-terminal side, the number of amino acid residue added to the C-terminal side is, in some cases, preferably small from the viewpoint of improvement of the productivity in cases of expression in a host such as *Escherichia coli*. The number of amino acid residues added to the C-terminal side may be preferably not more than 10 (for example, 1 to 10, 1 to 9, 1 to 8, 1 to 7, 1 to 6, 1 to 5, 1 to 4, 1 to 3, 1 to 2, or 1), more preferably not more than 5 (for example, 1 to 5, 1 to 4, 1 to 3, 1 to 2, or 1).

The fucose-binding protein of the present invention may or may not contain the later-mentioned "particular amino acid substitution". More specifically, in the fucose-binding protein of the present invention, a short-type BC2LCN sequence or a variant sequence thereof may contain the "particular amino acid substitution".

An amino acid sequence which is selected from short-type BC2LCN sequences and variant sequences thereof, and which does not contain the "particular amino acid substitution" is also referred to as "unmodified amino acid sequence". An amino acid sequence which is the same as an unmodified amino acid sequence except that the above amino acid sequence contains the "particular amino acid substitution" is also referred to as "modified amino acid sequence". Thus, examples of the fucose-binding protein of the present invention also include proteins containing a modified amino acid sequence. The unmodified amino acid sequence and the modified amino acid sequence may be the same except for the presence or absence of the "particular amino acid substitution".

The modified amino acid sequence may be, for example, an amino acid sequence which is the same as a short-type BC2LCN sequence except that the modified amino acid sequence contains the "particular amino acid substitution". Thus, the modified amino acid sequence may be, for example, the same as the short-type BC2LCN sequence except for the presence or absence of the "particular amino acid substitution". This modified amino acid sequence is also referred to as "modified amino acid sequence of the short-type BC2LCN sequence".

Further, the modified amino acid sequence may be, for example, an amino acid sequence which is the same as a variant sequence of a short-type BC2LCN sequence except that the modified amino acid sequence contains the "particular amino acid substitution". Thus, the modified amino acid sequence may be, for example, the same as the variant sequence of the short-type BC2LCN sequence except for the presence or absence of the "particular amino acid substitution". Thus, more specifically, the modified amino acid sequence may be, for example, an amino acid sequence which is the same as the short-type BC2LCN sequence except that the modified amino acid sequence contains substitution, deletion, insertion, and/or addition of one or several amino acid residues at one or more positions, as well as the "particular amino acid substitution". Further, more specifically, the modified amino acid sequence may be, for example, an amino acid sequence which is the same as an amino acid sequence having high homology to a short-type BC2LCN sequence except that the modified amino acid sequence contains the "particular amino acid substitution".

The variant sequence itself of a short-type BC2LCN sequence may be either an unmodified amino acid sequence or a modified amino acid sequence. In other words, the amino acid sequence modification that causes the difference between a short-type BC2LCN sequence and its variant sequence (for example, the substitution and/or the like of one or several amino acid residues, or amino acid sequence modification within the above-described range of homology) may or may not, partially or entirely, include the "particular amino acid substitution". Thus, for example, the modified amino acid sequence may be composed by introducing the "particular amino acid substitution" to a variant sequence of a short-type BC2LCN sequence not containing the "particular amino acid substitution", or a variant sequence of a short-type BC2LCN sequence already containing the "particular amino acid substitution" may be used as the modified amino acid sequence. The amino acid sequence modification that causes the difference between a short-type BC2LCN sequence and its variant sequence (for example, the substitution and/or the like of one or several amino acid residues or amino acid sequence modification within the above-described range of homology) may or may not, partially or entirely, include the substitutions not selected as the "particular amino acid substitution" among the amino acid substitutions described later in (1) to (5).

Further, in other words, the modified amino acid sequence may be, for example, a variant sequence of a modified amino acid sequence of a short-type BC2LCN sequence. To the variant sequence of a modified amino acid sequence of a short-type BC2LCN sequence, the description on the variant sequence of a short-type BC2LCN sequence may be applied mutatis mutandis except that the variant sequence of a modified amino acid sequence of a short-type BC2LCN sequence contains the "particular amino acid substitution". Thus, more specifically, the modified amino acid sequence may be, for example, an amino acid sequence which is the same as a modified amino acid sequence of a short-type BC2LCN sequence except that substitution, deletion, insertion, and/or addition of one or several amino acid residues is/are contained at one or more positions other than the position(s) of the "particular amino acid substitution". Further, more specifically, the modified amino acid sequence may be, for example, an amino acid sequence which has high homology to a modified amino acid sequence of a short-type BC2LCN sequence, and which contains the "particular amino acid substitution". The variant sequence of a modified amino acid sequence of a short-type BC2LCN sequence may or may not, partially or entirely, include the substitutions not selected as the "particular amino acid substitution" among the amino acid substitutions described later in (1) to (5).

Examples of the "particular amino acid substitution" include the amino acid substitutions described in the following (1) to (5):

(1) substitution of the amino acid residue corresponding to the glutamine residue at position 39 in the amino acid sequence of SEQ ID NO: 1, with an amino acid residue other than a glutamine residue;

(2) substitution of the amino acid residue corresponding to the cysteine residue at position 72 in the amino acid sequence of SEQ ID NO: 1, with an amino acid residue other than a cysteine residue;

(3) substitution of the amino acid residue corresponding to the glutamine residue at position 65 in the amino acid sequence of SEQ ID NO: 1, with an amino acid residue other than a glutamine residue;

(4) substitution of the amino acid residue corresponding to the glutamic acid residue at position 81 in the amino acid sequence of SEQ ID NO: 1, with an amino acid residue other than a glutamic acid residue; and (5) substitution of the amino acid residue corresponding to the glycine residue at position 36 in the amino acid sequence of SEQ ID NO: 1, with an amino acid residue other than a glycine residue.

The "particular amino acid substitution" may be, for example, one or more amino acid substitutions selected from the amino acid substitutions described in (1) to (5). Thus, the "particular amino acid substitution" may be any one amino acid substitution, or may be a combination of two, three, four, or five amino acid substitutions, selected from the amino acid substitutions described in (1) to (5).

By the "particular amino acid substitution", effects such as improvement of thermal stability, improvement of binding affinity to a fucose-containing sugar chain, and suppression of generation of a dimer due to disulfide bond formation may be obtained. By the "particular amino acid substitution", one or more effects selected from these effects may be obtained. Specific examples of the improvement of binding affinity to a fucose-containing sugar chain include improvement of binding affinity to a sugar chain containing a structure composed of Fucα1-2Galβ1-3GlcNAc and/or Fucα1-2Galβ1-3GalNAc.

By the amino acid substitutions described in (1) to (3), for example, improvement of thermal stability, and/or improvement of binding affinity to a fucose-containing sugar chain such as a sugar chain containing a structure composed of Fucα1-2Galβ1-3GlcNAc and/or Fucα1-2Galβ1-3GalNAc may be achieved. From the viewpoint of enabling achievement of the improved thermal stability, and/or achievement of the improved binding affinity to a fucose-containing sugar chain, the amino acid substitution described in (1) may be substitution of the amino acid residue corresponding to the glutamine residue at position 39 in the amino acid sequence of SEQ ID NO: 1 preferably with a leucine residue or a methionine residue, more preferably with a leucine residue. By substituting the amino acid residue corresponding to the glutamine residue at position 39 in the amino acid sequence of SEQ ID NO: 1 with any of these amino acid residues, for example, improved binding affinity to both sugar chains containing structures composed of Fucα1-2Galβ1-3GlcNAc and Fucα1-2Galβ1-3GalNAc, respectively, may be achieved. The substitution of the amino acid residue corresponding to the glutamine residue at position 39 in the amino acid sequence of SEQ ID NO: 1 with a leucine residue is also referred to as "Q39L". Other amino acid substitutions may be similarly abbreviated based on the types of the unsubstituted and substituted amino acid residues, and the position of these amino acid residues. In particular, from the viewpoint of enabling achievement of the improved thermal stability, and/or achievement of the improved binding affinity to a fucose-containing sugar chain, the amino acid substitution described in (2) may be substitution of the amino acid residue corresponding to the cysteine residue at position 72 in the amino acid sequence of SEQ ID NO: 1 preferably with a glycine residue or an alanine residue, more preferably with a glycine residue. By substituting the amino acid residue corresponding to the cysteine residue at position 72 in the amino acid sequence of SEQ ID NO: 1 with any of these amino acid residues, for example, improved binding affinity to both sugar chains containing structures composed of Fucα1-2Galβ1-3GlcNAc and Fucα1-2Galβ1-3GalNAc, respectively, may be achieved. In particular, from the viewpoint of enabling achievement of the improved thermal stability, the amino acid substitution described in (3) may be substitution of the amino acid residue corresponding to the glutamine residue at position 65 in the amino acid sequence of SEQ ID NO: 1 preferably with a leucine residue.

The fucose-binding protein of the present invention may contain, for example, at least one or more amino acid substitutions selected from the amino acid substitutions described in (1) to (3). Thus, the fucose-binding protein of the present invention may contain, for example, at least the amino acid substitution described in (1), (2), or (3). The fucose-binding protein of the present invention may contain, for example, at least a combination of two or three amino acid substitutions selected from the amino acid substitutions described in (1), (2), or (3). The amino acid substitutions described in (1) to (3), either individually or as a combination of a plurality thereof, can enable achievement of the improved thermal stability, and/or the improved binding affinity to a fucose-containing sugar chain. In particular, as described later in Examples, from the viewpoint of enabling achievement of remarkable improvement in the thermal stability, a combination of a plurality of the amino acid substitutions described in (1) to (3) may be preferably used. Examples of the combination include a combination of the amino acid substitutions described in (1) and (2), a combination of the amino acid substitutions described in (1) and (3), a combination of the amino acid substitutions described in (2) and (3), and a combination of the amino acid substitutions described in (1), (2), and (3). Specific examples of the combination include Q39L/C72G and Q39L/Q65L/C72G. More specifically, the fucose-binding protein of the present invention may contain, for example, at least the amino acid substitution(s) described in (1) and/or (2). More specifically the fucose-binding protein of the present invention may contain, for example, at least the amino acid substitution(s) described in (1) and/or (2), and the amino acid substitution described in (3). More specifically, the fucose-binding protein of the present invention may contain, for example, at least the amino acid substitutions described in (1), (2), and (3).

By the amino acid substitution described in (4), for example, improvement of binding affinity to a fucose-containing sugar chain such as a sugar chain containing a structure composed of Fucα1-2Galβ1-3GlcNAc and/or Fucα1-2Galβ1-3GalNAc may be achieved. In particular, from the viewpoint of enabling achievement of the improved binding affinity to a fucose-containing sugar chain, the amino acid substitution described in (4) may be substitution of the amino acid residue corresponding to the glutamic acid residue at position 81 in the amino acid sequence of SEQ ID NO: 1 preferably with a cysteine residue, a glutamine residue, a histidine residue, a methionine residue, a valine residue, a lysine residue, a serine residue, an isoleucine residue, a tyrosine residue, a glycine residue, a proline residue, a leucine residue, or an asparagine residue, more preferably with a cysteine residue, a glutamine residue, a histidine residue, or a methionine residue. By substituting the amino acid residue corresponding to the glutamic acid residue at position 81 in the amino acid sequence of SEQ ID NO: 1 with a cysteine residue, a glutamine residue, a histidine residue, or a methionine residue, for example, improved binding affinity to both sugar chains containing structures composed of Fucα1-2Galβ1-3GlcNAc and Fucα1-2Galβ1-3GalNAc, respectively, may be achieved.

By the amino acid substitution described in (5), for example, suppression of generation of a dimer due to disulfide bond formation may be achieved. In particular, from the viewpoint of enabling achievement of the suppression of generation of a dimer due to disulfide bond formation, the amino acid substitution described in (5) may be substitution of the amino acid residue corresponding to the glycine residue at position 36 in the amino acid sequence of SEQ ID NO: 1 preferably with a cysteine residue. The disulfide bond may be, for example, a disulfide bond formed in cases where an oligopeptide containing one or more cysteine residues is added in the production of the fucose-binding protein of the present invention.

"Amino acid residue at position X in the amino acid sequence of SEQ ID NO: 1" means the amino acid residue present at the Xth position as counted from the N-terminus of the amino acid sequence of SEQ ID NO: 1. "Amino acid residue corresponding to the amino acid residue at position X in the amino acid sequence of SEQ ID NO: 1" in a certain amino acid sequence means the amino acid residue, in the certain amino acid sequence, which is placed at the same position as the Xth amino acid residue in the amino acid sequence of SEQ ID NO: 1 in an alignment of the certain amino acid sequence with the amino acid sequence of SEQ ID NO: 1. For example, in the case of Q39L, "amino acid residue corresponding to the glutamine residue at position 39 in the amino acid sequence of SEQ ID NO: 1" in a certain amino acid sequence means the amino acid residue, in the certain amino acid sequence, which is placed at the same position as the glutamine residue at position 39 in the amino acid sequence of SEQ ID NO: 1 in an alignment of the certain amino acid sequence with the amino acid sequence of SEQ ID NO: 1. "Amino acid residue corresponding to the amino acid residue at position X in the amino acid sequence of SEQ ID NO: 1" in the amino acid sequence of SEQ ID NO: 1 means the Xth amino acid residue itself in the amino acid sequence of SEQ ID NO: 1. Thus, the position of the "particular amino acid substitution" does not necessarily represents the absolute position in the fucose-binding protein of the present invention, and it represents a relative position based on the amino acid sequence of SEQ ID NO: 1. More specifically, for example, in cases where the fucose-binding protein of the present invention contains insertion, deletion, or addition of an amino acid residue(s) in the N-terminal side relative to the position of the "particular amino acid substitution", the absolute position of the "particular amino acid substitution" may change in accordance therewith. The position of the "particular amino acid substitution" in the fucose-binding protein of the present invention can be identified by, for example, alignment of the amino acid sequence of the fucose-binding protein of the present invention with the amino acid sequence of SEQ ID NO: 1. The alignment can be carried out by, for example, using an alignment program such as BLAST. The same applies to the position of the "particular amino acid substitution" in an arbitrary amino acid sequence such as a variant sequence of a short-type BC2LCN sequence. The amino acid residue before the "particular amino acid substitution" represents the type of the unsubstituted amino acid residue in the amino acid sequence of SEQ ID NO: 1, and may or may not be conserved in unmodified amino acid sequences other than the amino acid sequence of SEQ ID NO: 1.

Specific examples of the fucose-binding protein of the present invention include fucose-binding proteins containing an amino acid sequence represented by any of the following: SEQ ID NO: 2 (the amino acid sequence corresponding to position 1 to position 129 in the amino acid sequence of SEQ ID NO: 1), SEQ ID NO: 3 (the amino acid sequence corresponding to position 1 to position 127 in the amino acid sequence of SEQ ID NO: 1), SEQ ID NO: 4 (the amino acid sequence which is the same as SEQ ID NO: 2 except that the glycine residue at position 36 is substituted with a cysteine residue), SEQ ID NO: 5 (the amino acid sequence which is the same as SEQ ID NO: 3 except that the glycine residue at position 36 is substituted with a cysteine residue), SEQ ID NO: 6 (the amino acid sequence corresponding to position 1 to position 126 in the amino acid sequence of SEQ ID NO: 1), SEQ ID NO: 7 (the amino acid sequence which is the same as SEQ ID NO: 2 except that the glutamic acid residue at position 81 is substituted with a cysteine residue), SEQ ID NO: 8 (the amino acid sequence which is the same as SEQ ID NO: 2 except that the glutamic acid residue at position 81 is substituted with a glutamine residue), SEQ ID NO: 9 (the amino acid sequence which is the same as SEQ ID NO: 2 except that the glutamic acid residue at position 81 is substituted with a histidine residue), SEQ ID NO: 10 (the amino acid sequence which is the same as SEQ ID NO: 2 except that the glutamic acid residue at position 81 is substituted with a methionine residue), SEQ ID NO: 11 (the amino acid sequence which is the same as SEQ ID NO: 3 except that the cysteine residue at position 72 is substituted with a glycine residue), SEQ ID NO: 12 (the amino acid sequence which is the same as SEQ ID NO: 3 except that the cysteine residue at position 72 is substituted with an alanine residue), SEQ ID NO: 13 (the amino acid sequence which is the same as SEQ ID NO: 3 except that the glutamine residue at position 39 is substituted with a leucine residue), SEQ ID NO: 14 (the amino acid sequence which is the same as SEQ ID NO: 3 except that the glutamine residue at position 39 is substituted with a methionine residue), SEQ ID NO: 15 (the amino acid sequence which is the same as SEQ ID NO: 3 except that the glutamine residue at position 39 is substituted with a leucine residue, and that the cysteine residue at position 72 is substituted with a glycine residue), and SEQ ID NO: 16 (the amino acid sequence which is the same as SEQ ID NO: 3 except that the glutamine residue at position 39 is substituted with a leucine residue, that the glutamine residue at position 65 is substituted with a leucine residue, and that the cysteine residue at position 72 is substituted with a glycine residue). The fucose-binding protein of the present invention may be, for example, composed of the amino acid sequence represented by any of these SEQ ID NOs. In particular, compared to proteins containing the amino acid sequence of SEQ ID NO: 1, such as BC2LCN(155)cys, from the viewpoint of enabling achievement of improved productivity in cases of expression in a host such as *Escherichia coli*, the fucose-binding protein of the present invention may preferably be a fucose-binding protein containing the amino acid sequence of SEQ ID NO: 2, SEQ ID NO: 3, SEQ ID NO: 4, SEQ ID NO: 5, SEQ ID NO: 6, SEQ ID NO: 11, SEQ ID NO: 13, SEQ ID NO: 15, or SEQ ID NO: 16. Further, in particular, compared to proteins containing the amino acid sequence of SEQ ID NO: 1, such as BC2LCN(155)cys, from the viewpoint of enabling achievement of improved productivity in cases of expression in a host such as *Escherichia coli*, and achievement of improved binding affinity to a fucose-containing sugar chain such as a sugar chain containing a structure composed of Fucα1-2Galβ1-3GlcNAc and/or Fucα1-2Galβ1-3GalNAc, the fucose-binding protein of the present invention may more preferably be a fucose-binding protein containing the amino acid sequence of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 15, or SEQ ID NO: 16. Further, in particular, compared to proteins containing the amino acid sequence of SEQ ID NO: 1, such as BC2LCN(155)cys, from the viewpoint of enabling achievement of improved productivity in cases of expression in a host such as *Escherichia coli*, achievement of improved binding affinity to a fucose-containing sugar chain such as a sugar chain containing a structure composed of Fucα1-2Galβ1-3GlcNAc and/or Fucα1-2Galβ1-3GalNAc, and achievement of improved thermal stability, the fucose-binding protein of the present invention may still more preferably be a fucose-binding protein containing the amino acid sequence of SEQ ID NO: 11, SEQ ID NO: 12, SEQ ID NO: 13, SEQ ID NO: 15, or SEQ ID NO: 16.

The amino acid sequences contained in the fucose-binding protein of the present invention exemplified above (such as short-type BC2LCN sequences and their variant sequences, and their modified amino acid sequences) are also collectively referred to as "core sequence". Thus, the fucose-binding protein of the present invention may be a protein containing a core sequence. The fucose-binding protein of the present invention may be a protein composed of a core sequence, or may further contain, in addition to the core sequence, an amino acid sequence(s) in the N-terminal side and/or C-terminal side thereof. The amino acid sequence contained in the N-terminal side or C-terminal side of the core sequence is also referred to as "additional sequence". The amino acid sequences contained in the N-terminal side and C-terminal side of the core sequence are also referred to as "N-terminal additional sequence" and "C-terminal additional sequence", respectively. Each additional sequence is not limited as long as the fucose-binding protein of the present invention has binding affinity to a fucose-containing sugar chain, and as long as the improvement in the productivity in cases of expression in a host such as *Escherichia coli* is not deteriorated.

The length of the N-terminal additional sequence, for example, may be not less than 1 residue, not less than 2 residues, not less than 3 residues, not less than 4 residues, not less than 5 residues, not less than 10 residues, not less than 15 residues, not less than 20 residues, or not less than 30 residues, may be not more than 60 residues, not more than 50 residues, not more than 40 residues, not more than 30 residues, not more than 20 residues, not more than 15 residues, not more than 12 residues, not more than 10 residues, not more than 7 residues, or not more than 5 residues, or may be a consistent combination thereof. More specifically, for example, the length of the N-terminal additional sequence may be 5 to 60 residues, 5 to 20 residues, or 5 to 15 residues.

The length of the C-terminal additional sequence, for example, may be not less than 1 residue, not less than 2 residues, not less than 3 residues, not less than 4 residues, or not less than 5 residues, may be not more than 15 residues, not more than 12 residues, not more than 10 residues, not more than 7 residues, or not more than 5 residues, or may be a consistent combination thereof. More specifically, for example, the length of the C-terminal additional sequence may be 2 to 10 residues.

Examples of the additional sequence include amino acid sequences useful for purification of the fucose-binding protein of the present invention (hereinafter also referred to as "purification tag"). More specifically, the purification tag may be an amino acid sequence useful for separating the fucose-binding protein of the present invention from a solution in the presence of a contaminant. Examples of the purification tag include oligopeptides containing a polyhistidine sequence; glutathion S-transferase; maltose-binding proteins; cellulose-binding domains; the myc tag; and the FLAG tag. Particular examples of the purification tag include oligopeptides containing a polyhistidine sequence. By using an oligopeptide containing a polyhistidine sequence, the fucose-binding protein of the present invention can be purified by, for example, nickel chelate affinity chromatography. "Polyhistidine sequence" means an amino acid sequence composed of a repeat of histidine residues. The number of the repeating histidine residues (that is, the length of the polyhistidine sequence) is not limited as long as a desired effect can be obtained. The number of the repeating histidine residues may be set, for example, within a range in which the fucose-binding protein of the present invention can be purified by nickel chelate affinity chromatography. The number of the repeating histidine residues may be, for example, preferably 5 to 15, more preferably 5 to 10. The oligopeptide containing a polyhistidine sequence may or may not be composed of a polyhistidine sequence. The length of the oligopeptide containing a polyhistidine sequence is not limited as long as the oligopeptide contains the polyhistidine sequence, and it may be, for example, preferably not more than 20 residues, more preferably not more than 15 residues. More specifically, for example, the length of the oligopeptide containing a polyhistidine sequence may be preferably not more than 20 residues in cases where the number of the repeating histidine residues is 5 residues to 15 residues, more preferably not more than 15 residues in cases where the number of the repeating histidine residues is 5 residues to 10 residues. The purification tag such as an oligopeptide containing a polyhistidine sequence may be added to either one of the N-terminal side and C-terminal side of the core sequence, or may be added to both. The purification tag such as an oligopeptide containing a polyhistidine sequence may preferably be added to the N-terminal side of the core sequence.

Examples of the additional sequence also include amino acid sequences useful for immobilizing the fucose-binding protein of the present invention on a carrier such as a support for chromatography (hereinafter also referred to as "carrier-immobilization tag"). Examples of the carrier-immobilization tag include oligopeptides containing a cysteine residue or lysine residue. The length of the carrier-immobilization tag is not limited as long as a desired effect can be obtained. The length of the carrier-immobilization tag, for example, may be not less than 2 residues, not less than 3 residues, not less than 4 residues, or not less than 5 residues, may be not more than 15 residues, not more than 12 residues, not more than 10 residues, not more than 7 residues, or not more than 5 residues, or may be a consistent combination thereof. More specifically, for example, the length of the carrier-immobilization tag may be 2 to 10 residues. In particular, from the viewpoint of enabling achieving the immobilization on the insoluble carrier highly selectively and highly efficiently, the carrier-immobilization tag may be preferably an oligopeptide containing one or more cysteine residues, more preferably an oligopeptide of 2 to 10 residues containing one or more cysteine residues. Specific examples of such a carrier-immobilization tag include the oligopeptide composed of the three amino acid residues "Gly-Gly-Cys", the oligopeptide composed of the five amino acid residues "Ala-Ser-Gly-Gly-Cys (SEQ ID NO: 66)", the oligopeptide composed of the seven amino acid residues "Gly-Gly-Gly-Ser-Gly-Gly-Cys (SEQ ID NO: 67)", and variant sequences thereof. To the variant sequences of the carrier-immobilization tag, the description on the variant sequences of the short-type BC2LCN sequence may be applied mutatis mutandis. The carrier-immobilization tag such as an oligopeptide containing one or more cysteine residues may be added to either one of the N-terminal side and C-terminal side of the core sequence, or may be added to both. The carrier-immobilization tag such as an oligopeptide containing one or more cysteine residues may preferably be added to the C-terminal side of the core sequence.

Examples of the additional sequence also include signal peptides. By the signal peptide, for example, efficient expression of the fucose-binding protein of the present invention in a host may be promoted. By the signal peptide, for example, the fucose-binding protein of the present invention may be secreted into the periplasm. In cases where the host is *Escherichia coli*, examples of the signal peptide include signal peptides of proteins such as PelB, DsbA, MalE, and TorT. The signal peptide may usually be added to the N-terminal side of the core sequence. In cases where the fucose-binding protein of the present invention contains the signal peptide and another N-terminal additional sequence, the signal peptide may be added to the N-terminal side of the other N-terminal additional sequence. The signal peptide may be eliminated upon secretion of the fucose-binding protein of the present invention into the periplasm or the like. Thus, the term "the fucose-binding protein of the present invention contains a signal peptide" may simply mean translation of the fucose-binding protein of the present invention in a form in which the protein contains the signal peptide, and hence does not necessarily require containing of the signal peptide in the finally obtained fucose-binding protein of the present invention.

The fucose-binding protein of the present invention is composed such that the protein does not contain the amino acid sequence of SEQ ID NO: 1. The fucose-binding protein of the present invention may also be composed such that the protein does not contain an amino acid sequence having high homology to the amino acid sequence of SEQ ID NO: 1.

Examples of the amino acid sequence having high homology to the amino acid sequence of SEQ ID NO: 1 include amino acid sequences having a homology of not less than 99%, not less than 98%, not less than 97%, not less than 96%, not less than 95%, not less than 94%, not less than 93%, not less than 92%, not less than 91%, or not less than 90% to the amino acid sequence of SEQ ID NO: 1.

The fucose-binding protein of the present invention may be composed such that it does not contain the deleted sequence. The fucose-binding protein of the present invention is composed such that the protein does not contain the deleted sequence at least adjacent to the C-terminus of the short-type BC2LCN sequence, so as not to contain the amino acid sequence of SEQ ID NO: 1. The fucose-binding protein of the present invention may be composed such that the protein does not contain an amino acid sequence having high homology to the deleted sequence. Examples of the amino acid sequence having high homology to the deleted sequence include amino acid sequences having a homology of not less than 95%, not less than 90%, not less than 85%, not less than 80%, not less than 75%, not less than 70%, not less than 65%, not less than 60%, not less than 55%, or not less than 50% to the deleted sequence. The fucose-binding protein of the present invention may be composed, for example, such that the core sequence does not contain the deleted sequence. The fucose-binding protein of the present invention may be composed, for example, such that the core sequence does not contain an amino acid sequence having high homology to the deleted sequence. The fucose-binding protein of the present invention may be composed, for example, such that the protein does not contain the deleted sequence in the C-terminal side relative to the core sequence. The fucose-binding protein of the present invention may be composed, for example, such that protein does not contain an amino acid sequence having high homology to the deleted sequence in the C-terminal side relative to the core sequence.

The term "does not contain the deleted sequence" means that the entire sequence of the deleted sequence is not contained, and hence does not exclude containing of a partial sequence of the deleted sequence. The acceptable length of the partial sequence may be appropriately set depending on conditions such as the length of the deleted sequence. The acceptable length of the partial sequence may be, for example, not more than 50%, not more than 40%, not more than 30%, not more than 20%, or not more than 10% of the length of the deleted sequence. The acceptable length of the partial sequence may be, for example, not more than 7 residues, not more than 6 residues, not more than 5 residues, not more than 4 residues, not more than 3 residues, not more than 2 residues, or 1 residue.

The length of the core sequence, for example, may be not less than (X-15) residues, not less than (X-10) residues, not less than (X-7) residues, not less than (X-5) residues, not less than (X-3) residues, not less than (X-2) residues, not less than (X-1) residues, not less than X residues, not less than (X+1) residues, not less than (X+2) residues, not less than (X+3) residues, or not less than (X+5) residues, may be not more than (X+15) residues, not more than (X+10) residues, not more than (X+7) residues, not more than (X+5) residues, not more than (X+3) residues, not more than (X+2) residues, not more than (X+1) residues, not more than X residues, not more than (X-1) residues, not more than (X-2) residues, not more than (X-3) residues, or not more than (X-5) residues, or may be a consistent combination thereof. More specifically, the length of the core sequence may be, for example, (X−15) to (X+15) residues, (X−10) to (X+10) residues, (X−5) to (X+5) residues, or (X−2) to (X+2) residues.

The length of the core sequence, for example, may be not less than 95 residues, not less than 100 residues, not less than 105 residues, not less than 110 residues, not less than 115 residues, not less than 120 residues, or not less than 125 residues, may be not more than 165 residues, not more than 160 residues, not more than 155 residues, not more than 150 residues, not more than 145 residues, not more than 140 residues, not more than 135 residues, or not more than 130 residues, or may be a combination thereof. More specifically, for example, the length of the core sequence may be 95 to 155 residues, 105 to 150 residues, or 110 to 145 residues.

The length of the core sequence may be, for example, less than 155 residues. In particular, the length of the core sequence may be within the range exemplified above, and less than 155 residues.

When the length of the core sequence is represented as Y residues, the length of the fucose-binding protein of the present invention (that is, the entire length of the fucose-binding protein of the present invention) is not less than Y residues. When the length of the core sequence is represented as Y residues, the length of the fucose-binding protein of the present invention, for example, may be not less than Y residues, not less than (Y+1) residues, not less than (Y+2) residues, not less than (Y+3) residues, not less than (Y+5) residues, not less than (Y+10) residues, or not less than (Y+15) residues, may be not more than (Y+60) residues, not more than (Y+55) residues, not more than (Y+50) residues, not more than (Y+45) residues, not more than (Y+40) residues, not more than (Y+35) residues, not more than (Y+30) residues, not more than (Y+20) residues, not more than (Y+15) residues, not more than (Y+10) residues, or not more than (Y+5) residues, or may be a consistent combination thereof. More specifically, when the length of the core sequence is represented as Y residues, the length of the fucose-binding protein of the present invention may be, for example, Y to (Y+20) residues.

The length of the fucose-binding protein of the present invention, for example, may be not less than (X−15) residues, not less than (X−10) residues, not less than (X−7) residues, not less than (X−5) residues, not less than (X−3) residues, not less than (X−2) residues, not less than (X−1) residues, not less than X residues, not less than (X+1) residues, not less than (X+2) residues, not less than (X+3) residues, not less than (X+5) residues, not less than (X+10) residues, not less than (X+15) residues, not less than (X+20) residues, or not less than (X+25) residues, may be not more than (X+75) residues, not more than (X+70) residues, not more than (X+65) residues, not more than (X+60) residues, not more than (X+55) residues, not more than (X+50) residues, not more than (X+45) residues, not more than (X+40) residues, not more than (X+35) residues, not more than (X+30) residues, not more than (X+25) residues, not more than (X+20) residues, not more than (X+15) residues, not more than (X+10) residues, not more than (X+7) residues, not more than (X+5) residues, not more than (X+3) residues, not more than (X+2) residues, not more than (X+1) residues, not more than X residues, not more than (X−1) residues, not more than (X−2) residues, not more than (X−3) residues, or not more than (X−5) residues, or may be a consistent combination thereof. More specifically, the length of the fucose-binding protein of the present invention may be, for example, (X−15) to (X+35) residues, (X−10) to (X+30) residues, (X−5) to (X+25) residues, or (X−2) to (X+20) residues.

The length of the fucose-binding protein of the present invention, for example, may be not less than not less than 95 residues, not less than 100 residues, not less than 105 residues, not less than 110 residues, not less than 115 residues, not less than 120 residues, or not less than 125 residues, may be not more than 225 residues, not more than 220 residues, not more than 215 residues, not more than 210 residues, not more than 205 residues, not more than 200 residues, not more than 195 residues, not more than 190 residues, not more than 185 residues, not more than 180 residues, not more than 175 residues, not more than 170 residues, not more than 165 residues, not more than 160 residues, not more than 155 residues, not more than 150 residues, not more than 145 residues, not more than 140 residues, not more than 135 residues, or not more than 130 residues, or may be a combination thereof. More specifically, the length of the fucose-binding protein of the present invention may be, for example, 95 to 175 residues, 105 to 170 residues, or 110 to 165 residues.

The DNA encoding the fucose-binding protein of the present invention (hereinafter also referred to as "DNA of the present invention"), the expression vector comprising the DNA of the present invention (hereinafter also referred to as "expression vector of the present invention"), and the transformant comprising the DNA of the present invention or the expression vector of the present invention (hereinafter also referred to as "transformant of the present invention") are described below.

The DNA of the present invention can be obtained by, for example, a chemical synthesis method, or a DNA amplification method such as the Polymerase Chain Reaction (PCR) method. The DNA amplification method may be carried out using, as a template, a polynucleotide containing a nucleotide sequence to be amplified. Examples of the polynucleotide used as the template include genomic DNA, cDNA, synthetic DNA fragments, and vectors, containing the nucleotide sequence to be amplified. The nucleotide sequence of the DNA of the present invention may be designed, for example, by modification of the nucleotide sequence of the BC2L-C gene region in genomic DNA of *Burkholderia cenocepacia*, or by conversion from the amino acid sequence of the fucose-binding protein of the present invention. In the conversion from the amino acid sequence to the nucleotide sequence, it is preferred to take into account the codon usage in the host used for the production of the fucose-binding protein of the present invention. For example, in cases where *Escherichia coli* is used as the host, AGA, AGG, CGG, and CGA for arginine (Arg), ATA for isoleucine (Ile), CTA for leucine (Leu), GGA for glycine (Gly), and CCC for proline (Pro) are less frequently used codons (rare codons). Therefore, it is preferred to select codons other than these codons to carry out the conversion. Further, analysis of the codon usage is possible by utilizing a public database (such as the Codon Usage Database provided on the website of Kazusa DNA Research Institute, www.kazusa.or.jp/codon/; accession date: May 7, 2018). In the preparation of the DNA of the present invention, for simplifying the operation of amino acid residue substitution, an appropriate restriction enzyme recognition sequence(s) may be introduced without changing the amino acid sequence(s) around the amino acid residue substitution site(s). The DNA of the present invention obtained may be used as it is or after appropriate modification. The DNA of the present invention obtained may be subjected to modification such as construction of a variant or introduction of the "particular amino acid substitution". The modification of the DNA may be carried out by, for example, a genetic engineering method such as the error-prone PCR method, or mutation treatment using an agent, ultraviolet, or the like.

Specific examples of the DNA of the present invention include: DNA containing the nucleotide sequence of SEQ ID NO: 17, which encodes the amino acid sequence of SEQ ID NO: 2; DNA containing the nucleotide sequence of SEQ ID NO: 18, which encodes the amino acid sequence of SEQ ID NO: 3; DNA containing the nucleotide sequence of SEQ ID NO: 19, which encodes the amino acid sequence of SEQ ID NO: 4; DNA containing the nucleotide sequence of SEQ ID NO: 20, which encodes the amino acid sequence of SEQ ID NO: 5; DNA containing the nucleotide sequence of SEQ ID NO: 21, which encodes the amino acid sequence of SEQ ID NO: 6; DNA containing the nucleotide sequence of SEQ ID NO: 22, which encodes the amino acid sequence of SEQ ID NO: 7; DNA containing the nucleotide sequence of SEQ ID NO: 23, which encodes the amino acid sequence of SEQ ID NO: 8; DNA containing the nucleotide sequence of SEQ ID NO: 24, which encodes the amino acid sequence of SEQ ID NO: 9; DNA containing the nucleotide sequence of SEQ ID NO: 25, which encodes the amino acid sequence of SEQ ID NO: 10; DNA containing the nucleotide sequence of SEQ ID NO: 26, which encodes the amino acid sequence of SEQ ID NO: 11; DNA containing the nucleotide sequence of SEQ ID NO: 27, which encodes the amino acid sequence of SEQ ID NO: 12; DNA containing the nucleotide sequence of SEQ ID NO: 28, which encodes the amino acid sequence of SEQ ID NO: 13; DNA containing the nucleotide sequence of SEQ ID NO: 29, which encodes the amino acid sequence of SEQ ID NO: 14; DNA containing the nucleotide sequence of SEQ ID NO: 30, which encodes the amino acid sequence of SEQ ID NO: 15; and DNA containing the nucleotide sequence of SEQ ID NO: 31, which encodes the amino acid sequence of SEQ ID NO: 16. The DNA of the present invention may be, for example, composed of the nucleotide sequence represented by any of these SEQ ID NOs.

The fucose-binding protein of the present invention can be produced, for example, by expression of the fucose-binding protein of the present invention in the transformant of the present invention. The transformant of the present invention can express the fucose-binding protein of the present invention based on the DNA of the present invention contained therein. Thus, the transformant of the present invention is, in other words, a transformant capable of expressing the fucose-binding protein of the present invention.

The transformant of the present invention can be obtained by, for example, transforming a host using the DNA of the present invention. Thus, the transformant of the present invention may be, for example, a host transformed with the DNA of the present invention. The host is not limited as long as its transformation with the DNA of the present invention enables expression of the fucose-binding protein of the present invention. Examples of the host include animal cells, insect cells, and microorganisms. Examples of the animal cells include COS cells, CHO cells, Hela cells, NIH3T3 cells, HEK293 cells, and so forth. Examples of the insect cells include Sf9, BTI-TN-5B1-4, and so forth. Examples of the microorganisms include yeasts and bacteria. Examples of the yeasts include yeasts belonging to the genus *Saccharomyces*, such as *Saccharomyces cerevisiae*; yeasts belonging to the genus *Pichia*, such as *Pichia pastoris*; and yeasts belonging to the genus *Schizosaccharomyces*, such as *Schizosaccharomyces pombe*; and so forth. Examples of the bacteria include bacteria belonging to the genus *Escherichia*, such as *Escherichia coli*; and so forth. Examples of the *Escherichia coli* include the JM109 strain, BL21 (DE3) strain, NiCo21 (DE3) strain, W3110 strain, and so forth. In particular, from the viewpoint of productivity of the fucose-binding protein of the present invention, *Escherichia coli* may preferably be used as the host.

The DNA of the present invention may be retained in the transformant of the present invention in a mode allowing its expression. More specifically, the DNA of the present invention may be retained such that it is expressed under the regulation of a promoter that functions in the host. In cases where *Escherichia coli* is used as the host, examples of the promoter that functions in the host include the trp promoter, tac promoter, trc promoter, lac promoter, T7 promoter, recA promoter, lpp promoter, APL promoter, and APR promoter.

In the transformant of the present invention, the DNA of the present invention may be present, for example, on a vector that self-replicates outside the genomic DNA. Thus, for example, the DNA of the present invention can be introduced to the host as an expression vector containing the DNA of the present invention. Thus, in one mode, the transformant of the present invention may be a transformant having an expression vector containing the DNA of the present invention. The expression vector containing the DNA of the present invention is also referred to as "expression vector of the present invention". The expression vector of the present invention can be obtained by, for example, inserting the DNA of the present invention into an appropriate position in an expression vector. The expression vector is not limited as long as it can be stably present and is capable of replication in the host to be transformed therewith. Examples of the expression vector include bacteriophages, cosmids, and plasmids. In cases where *Escherichia coli* is used as the host, examples of the expression vector include the pET vector, pUC vector, pTrc vector, pCDF vector, and pBBR vector. The expression vector may contain a selection marker such as an antibiotic resistance gene. The appropriate position means a position where the insertion does not destroy regions involved in the replication function, selection marker, and transferability of the expression vector. In the process of inserting the DNA of the present invention into the expression vector, the DNA is preferably inserted in a state where it is linked to a functional DNA such as a promoter required for its expression.

In the transformant of the present invention, the DNA of the present invention may be introduced, for example, in the genomic DNA. The introduction of the DNA of the present invention into the genomic DNA can be carried out by, for example, utilizing a gene transfer method based on homologous recombination. Examples of the gene transfer method based on homologous recombination include a method using linear DNA, such as the Red-driven integration method (Datsenko, K. A., and Wanner, B. L. Proc. Natl. Acad. Sci. USA. 97:6640-6645 (2000)); a method using a vector containing a temperature-sensitive origin of replication; a method using a vector not having an origin of replication that functions in the host; and a transduction method using a phage.

The transformation of the host using a polynucleotide such as the expression vector of the present invention can be carried out by, for example, a method commonly used by those skilled in the art. For example, in cases where *Escherichia coli* is selected as the host, the transformation can be carried out by the competent cell method, heat shock method, electroporation method, or the like. By performing screening by an appropriate method after the transformation, the transformant of the present invention can be obtained.

Detailed information on genetic engineering methods such as expression vectors and promoters available for various microorganisms is described in, for example, "Fundamental Microbiology 8: Genetic Engineering. Kyoritsu Shuppan Co., Ltd. (1987)". These methods may be used.

In cases where the transformant of the present invention has the expression vector of the present invention, the expression vector of the present invention can be prepared from the transformant of the present invention. For example, from a culture obtained by culturing the transformant of the present invention, the expression vector of the present invention can be prepared by the alkaline extraction method, or by using a commercially available extraction kit such as the QIAprep Spin Miniprep kit (trade name; manufactured by QIAGEN).

The method of producing the fucose-binding protein of the present invention (hereinafter also referred to as "production method of the present invention") is described below. The production method of the present invention may be a method of producing the fucose-binding protein of the present invention, the method comprising, for example, the steps of:

culturing the transformant of the present invention to allow expression of the fucose-binding protein of the present invention (hereinafter also referred to as "first step"); and collecting the expressed fucose-binding protein of the present invention (hereinafter also referred to as "second step").

In the first step, the transformant of the present invention is cultured to allow expression of the fucose-binding protein of the present invention. The medium composition and the culture conditions in the first step may be appropriately set depending on conditions such as the type of the host and properties of the fucose-binding protein of the present invention. For example, the medium composition and the culture conditions may be set such that the host can be grown and can express the fucose-binding protein of the present invention. Examples of media that can be used therefor include media containing, as appropriate, a carbon source, nitrogen source, inorganic salt, and/or other organic components and/or inorganic components. For example, in cases where *Escherichia coli* is used as the host, Terrific Broth (TB) medium, Luria-Bertani (LB) medium, or the like supplemented with necessary nutrient sources may preferably be used. For selective growth of the transformant of the present invention based on the presence or absence of the expression vector of the present invention introduced, the culture is preferably carried out with a medium supplemented with an antibiotic corresponding to an antibiotic resistance gene contained in the expression vector. For example, in cases where the expression vector contains a kanamycin resistance gene, the medium may be supplemented with kanamycin. The same applies to cases where the DNA of the present invention is introduced in the genomic DNA. The culture temperature may be a temperature commonly known for the host used. For example, in cases where the host is *Escherichia coli*, the culture temperature may be 10° C. to 40° C., preferably 20° C. to 37° C. The pH of the medium may be within a pH range commonly known for the host used. For example, in cases where the host is *Escherichia coli*, the pH of the medium may be within the range of pH 6.8 to pH 7.4, preferably about pH 7.0.

In cases where the fucose-binding protein of the present invention is expressed under the regulation of an inducible promoter, an inducer may be added to the medium so as to allow favorable expression of the fucose-binding protein of the present invention. Examples of the inducer include isopropyl-β-D-thiogalactopyranoside (IPTG) in cases where the tac promoter or lac promoter is used. The inducer may be added at a concentration within the range of, for example, 0.005 to 1.0 mM, preferably 0.01 to 0.5 mM. The induction of expression by addition of IPTG may be carried out under conditions commonly known for the host used. Even in cases where the fucose-binding protein of the present invention is expressed under the regulation of an inducible promoter, addition of the inducer is not necessary when the fucose-binding protein of the present invention can be appropriately expressed even without the inducer.

In the second step, the expressed fucose-binding protein of the present invention is collected. More specifically, the fucose-binding protein of the present invention may be collected from the culture obtained. The "culture" means the entire culture broth obtained by culturing, or part thereof. The part is not limited as long as it is a part containing the fucose-binding protein of the present invention. Examples of the part include cells of the transformant of the present invention, cell secretions of the transformant of the present invention, and the medium after the culture (that is, the culture supernatant). The collection of the fucose-binding protein of the present invention may be carried out by, for example, a commonly known collection method for proteins. For example, in cases where the fucose-binding protein is produced by secretion into the culture, the cells may be separated by centrifugation, and the fucose-binding protein of the present invention may be collected from the resulting culture supernatant. In cases where the fucose-binding protein of the present invention is produced in the cells (including the periplasm in the cases of prokaryotes), the cells may be collected by centrifugation, and may then be disrupted by adding an enzyme treatment agent, surfactant, and/or the like thereto, followed by recovering the fucose-binding protein of the present invention from the cell homogenate.

The fucose-binding protein of the present invention collected may be purified as appropriate so as to obtain a desired purity. The purification of the fucose-binding protein of the present invention may be carried out by, for example, a known method used for separation and purification of proteins. Examples of the method of purifying the protein include a separation/purification method using liquid chromatography.

Examples of the liquid chromatography include ion-exchange chromatography, hydrophobic interaction chromatography, gel filtration chromatography, and affinity chromatography. The purification is preferably carried out by a combination of these chromatography. The purity and the molecular weight of the fucose-binding protein of the present invention can be confirmed using, for example, a method known in the art. Examples of the method include SDS polyacrylamide gel electrophoresis (SDS-PAGE) and gel filtration chromatography.

For utilization of the fucose-binding protein of the present invention, the protein may be, for example, immobilized on an insoluble carrier. More specifically, the fucose-binding protein of the present invention can be used as an adsorbent by immobilizing the protein on an insoluble carrier. Thus, the present invention provides an adsorbent comprising: an insoluble carrier; and the fucose-binding protein of the present invention immobilized on the insoluble carrier. The adsorbent is also referred to as "adsorbent of the present invention".

The adsorbent of the present invention can be produced by, for example, immobilizing the fucose-binding protein of the present invention on an insoluble carrier. The insoluble carrier is not limited. Examples of the insoluble carrier include inorganic carriers, such as silica gel, and glass having a gold thin film deposited thereon; water-insoluble polysaccharide-based carriers prepared by using a polysaccharide such as agarose, cellulose, chitin, or chitosan as a raw material, and cross-linked polysaccharide-based carriers prepared by cross-linking these using a cross-linking agent; cross-linked polysaccharide-based carriers prepared by cross-linking a water-soluble polysaccharide such as dextran, pullulan, starch, alginate, or carrageenan using a cross-linking agent; and synthetic polymer-based carriers such as poly(meth)acrylate, polyvinyl alcohol, polyurethane, and polystyrene, and cross-linked synthetic polymer-based carriers prepared by cross-linking these using a cross-linking agent. In particular, from the viewpoint of the presence of a hydroxyl group, and of simply carrying out the later-mentioned modification with a hydrophilic polymer, preferred examples of the insoluble carrier include uncharged polysaccharide-based carriers such as agarose, cellulose, dextran, and pullulan, and cross-linked polysaccharide-based carriers prepared by cross-linking these using a cross-linking agent; and hydrophilic synthetic polymer-based carriers such as poly(meth)acrylate and polyurethane, and cross-linked hydrophilic synthetic polymer-based carriers prepared by cross-linking these using a cross-linking agent.

From the viewpoint of suppressing non-specific adsorption of substances, the insoluble carrier may preferably have a surface modified with a hydrophilic polymer, more preferably have a surface on which a hydrophilic polymer is covalently immobilized. Examples of the hydrophilic polymer include neutral polysaccharides such as agarose, cellulose, dextran, pullulan, and starch, and synthetic polymers containing a hydroxyl group, such as poly(2-hydroxyethyl methacrylate) and polyvinyl alcohol. In particular, from the viewpoint of high hydrophilicity, and of simply carrying out the covalent immobilization on the surface of the insoluble carrier, preferred examples of the hydrophilic polymer include neutral polysaccharides such as dextran, pullulan, and starch. More preferred examples of the hydrophilic polymer include dextran and pullulan. The molecular weight of the hydrophilic polymer such as dextran or pullulan is not limited. From the viewpoint of allowing sufficient hydrophilic modification of the surface of the insoluble carrier, the molecular weight of the hydrophilic polymer such as dextran or pullulan is preferably 10,000 to 1,000,000 in terms of the number average molecular weight.

The shape of the insoluble carrier is not limited. The shape of the insoluble carrier may be, for example, any of a particle shape, sponge shape, flat film shape, flat plate shape, hollow shape, and fiber shape. From the viewpoint of allowing efficient adsorption of cells to the adsorbent, the insoluble carrier may preferably be a particulate carrier, more preferably be a spherical particulate carrier.

In cases where a column is packed with an adsorbent produced from the insoluble carrier, the particle size of the carrier in the water-swollen state may be preferably 100 μm to 1000 μm, more preferably 100 μm to 500 μm, still more preferably 150 μm to 300 μm, from the viewpoint of allowing sufficient contact between the cells to be separated and the surface of the adsorbent while allowing the cells not bound to the adsorbent to pass through the gaps of the adsorbent. The "particle size" may mean the average particle size D50. The "average particle size D50" may mean the particle size at an integrated value of 50% on a volume basis in the result of measurement of the particle size distribution based on the Coulter principle. The particle size of the insoluble carrier can be measured using, for example, a precision particle size distribution measurement apparatus (trade name, "Multisizer 3") manufactured by Beckman Coulter, Inc. The particle size of the insoluble carrier can also be determined by, for example, taking an image of a graduated slide glass under an optical microscope; taking an image of a plurality of particles to be measured, at the same magnification; measuring, using a scale, the particle sizes of the plurality of carriers whose images were taken; and then calculating the average of the particle sizes.

The presence or absence of pores in the insoluble carrier is not limited. The insoluble carrier may be, for example, porous or nonporous. From the viewpoint of simply introducing an active functional group for immobilizing the protein used for the adsorbent of the present invention on the carrier, the insoluble carrier may preferably be a particulate carrier containing a hydroxyl group. As the insoluble carrier, for example, a commercially available product may be used. Examples of the commercially available product include Toyopearl (manufactured by Tosoh Corporation), which uses poly(meth)acrylate as a raw material; Sepharose (manufactured by GE Healthcare), which uses agarose as a raw material; and Celphere (manufactured by Asahi Kasei Corporation), which uses cellulose as a raw material.

The adsorbent of the present invention can be produced by, for example, immobilizing the fucose-binding protein of the present invention on an insoluble carrier. More specifically, the adsorbent of the present invention can be produced by, for example, a method comprising the steps of: producing a reactive insoluble carrier from an insoluble carrier (hereinafter also referred to as "Step X"); and immobilizing the fucose-binding protein of the present invention on the reactive insoluble carrier (hereinafter referred to as "Step Y").

Step X is a step of producing a reactive insoluble carrier from an insoluble carrier. The reactive insoluble carrier can be produced by, for example, introducing a reactive functional group to an insoluble carrier. The reactive functional group is not limited as long as it can be used for immobilization of the fucose-binding protein of the present invention on the insoluble carrier. Examples of the reactive functional group include common functional groups for immobilization of proteins. Specific examples of the reactive functional group include an epoxy group, a formyl group, a carboxyl group, an active ester group, an amino group, a maleimide group, and a haloacetyl group.

Examples of the method of introducing the reactive functional group to the insoluble carrier include common methods of introducing a functional group.

Examples of the method of introducing the epoxy group include a method in which a hydroxyl group of the insoluble carrier is reacted with an epoxy-containing compound. Examples of the epoxy-containing compound include halohydrins such as epichlorohydrin and epibromohydrin; diglycidyl ethers such as ethylene glycol diglycidyl ether, glycerol diglycidyl ether, 1,4-butanediol diglycidyl ether, 1,6-hexanediol diglycidyl ether, diethylene glycol diglycidyl ether, tetraethylene glycol diglycidyl ether, and resorcinol diglycidyl ether; triglycidyl ethers such as glycerol triglycidyl ether, erythritol triglycidyl ether, and diglycerol triglycidyl ether; and tetraglycidyl ethers such as erythritol tetraglycidyl ether and pentaerythritol tetraglycidyl ether. In cases where the hydroxyl group of the insoluble carrier is reacted with the epoxy-containing compound, the reaction may preferably be carried out under basic conditions from the viewpoint of increasing the reaction efficiency.

Examples of the method of introducing the formyl group include a method in which the hydroxyl group of the insoluble carrier is reacted with a bifunctional aldehyde such as glutaraldehyde, and a method in which the insoluble carrier is reacted with an oxidizing agent such as sodium periodate. Examples of the method of introducing the formyl group also include a method in which an insoluble carrier containing an epoxy group introduced therein is reacted with a compound such as D-glucamine, N-methyl-D-glucamine, or α-thioglycerol to introduce the adjacent hydroxyl group to the insoluble carrier, and then the resulting product is reacted with an oxidizing agent such as sodium periodate.

Examples of the method of introducing the carboxyl group include a method in which a hydroxyl group of the insoluble carrier is reacted with a haloacetic acid such as monochloroacetic acid or monobromoacetic acid under basic conditions. Examples of the method of introducing the carboxyl group also include a method in which an insoluble carrier containing an epoxy group introduced therein is reacted with an amino acid such as glycine, alanine, aspartic acid, or glutamic acid; an amino-containing carboxylic acid such as β-alanine, 4-aminobutyric acid, or 6-aminohexanoic acid; or a sulfur-containing carboxylic acid such as thioglycolic acid or thiomalic acid; under basic conditions. Examples of the method of introducing the carboxyl group also include a method in which a carboxyl group introduced in an insoluble carrier is reacted with N-hydroxysuccinimide in the presence of a condensing agent such as 1-(3-dimethylaminopropyl)-3-ethylcarbodiimide hydrochloride (hereinafter referred to as EDC), for induction into N-hydroxysuccinimide ester, which is an active ester group.

Examples of the method of introducing the amino group include a method in which an insoluble carrier containing an epoxy group introduced therein is reacted with a compound containing at least two amino groups, such as ethylenediamine, diethylenetriamine, or tris(2-aminoethyl)amine.

Examples of the method of introducing the maleimide group include a method in which an insoluble carrier containing a hydroxyl group and/or amino group is reacted with a carboxylic acid containing a maleimide group, such as 3-maleimidopropionic acid, 4-maleimidobutyric acid, 6-maleimidohexanoic acid, or 4-(N-maleimidomethyl)cyclohexanecarboxylic acid in the presence of a condensing agent such as EDC. Examples of the method of introducing the maleimide group also include a method in which an insoluble carrier is reacted with an N-hydroxysuccinimide ester or N-hydroxysulfosuccinimide ester of a carboxylic acid containing a maleimide group.

Examples of the method of introducing the haloacetyl group include a method in which an insoluble carrier containing a hydroxyl group or an insoluble carrier containing an amino group introduced therein is reacted with an acid halide such as chloroacetic acid chloride, bromoacetic acid chloride, or bromoacetic acid bromide, and a method in which the carrier is reacted with a halogenated acetic acid such as chloroacetic acid, bromoacetic acid, or iodoacetic acid in the presence of a condensing agent such as EDC. Examples of the method of introducing the haloacetyl group also include a method in which an insoluble carrier is reacted with an N-hydroxysuccinimide ester or N-hydroxysulfosuccinimide ester of a halogenated acetic acid.

Step Y is a step of immobilizing the fucose-binding protein of the present invention on the reactive insoluble carrier produced in Step X. Examples of the method of immobilizing the fucose-binding protein of the present invention on the reactive insoluble carrier obtained in Step X include common methods of immobilizing a protein on a carrier. Examples of the method of immobilizing the protein on the carrier include a method in which the protein is immobilized on the insoluble carrier by coordinate bonding or affinity bonding without forming a covalent bond, a method in which an active functional group for immobilization is introduced to the protein, and then the active functional group for immobilization is reacted with the insoluble carrier to immobilize the protein on the insoluble carrier, and a method in which an active functional group for immobilization introduced in the insoluble carrier is reacted with the protein to form a covalent bond, to immobilize the protein on the insoluble carrier.

Examples of the method of immobilizing the protein on the insoluble carrier without forming a covalent bond include a method in which an avidin-biotin affinity bond is used to immobilize a biotinylated protein on an insoluble carrier having an avidin such as Streptavidin Sepharose High Performance (manufactured by GE Healthcare) immobilized thereon. Examples of the method of introducing the biotin to the protein include a method in which a biotinylation reagent containing an active ester group such as 9-(biotinamido)-4,7-dioxanonanoic acid-N-succinimidyl is reacted with an amino group of the protein, and a method in which a biotinylation reagent containing a maleimide group, such as N-biotinyl-N'-[2-(N-maleimido)ethyl]piperazine hydrochloride, is reacted with a mercapto group of the protein.

Examples of the method of reacting the active functional group for immobilization introduced in the protein with the insoluble carrier to form a covalent bond, to immobilize the protein include a method in which the active ester group of a compound containing both a maleimide group and an active ester group, such as 4-(N-maleimidomethyl)cyclohexane-1-carboxylic acid 3-sulfo-N-hydroxysuccinimide ester sodium salt, is reacted with an amino group of the protein to introduce the maleimide group to the protein, and then the resulting product is reacted with an insoluble carrier containing a mercapto group introduced therein.

Examples of the method of reacting the active functional group for immobilization introduced in the insoluble carrier with the protein to immobilize the protein on the insoluble carrier include a method in which an epoxy group, a formyl group, a carboxyl group, or an active ester group such as N-hydroxysuccinimide ester introduced in the insoluble carrier is reacted with an amino group of the protein, a method in which an amino group introduced in the insoluble carrier is reacted with a carboxyl group of the protein, and a method in which an epoxy group, a maleimide group, a haloacetyl group, or a haloalkyl group introduced in the insoluble carrier is reacted with a mercapto group of the protein.

From the viewpoint of enabling the immobilization of the protein on the insoluble carrier in a short time with a high yield, preferred examples of the immobilization method include the method in which a formyl group or an active ester group introduced in the insoluble carrier is reacted with an amino group of the protein, and the method in which a maleimide group or a haloacetyl group introduced in the insoluble carrier is reacted with a mercapto group of the protein. From the viewpoint of enabling the immobilization reaction at a nearly neutral pH, and enabling suppression of protein denaturation, more preferred examples of the immobilization method include the method in which a maleimide group or a haloacetyl group introduced in the insoluble carrier is reacted with a mercapto group of the protein. From the viewpoint of increasing stability of the functional group, still more preferred examples of the immobilization method include the method in which a maleimide group introduced in the insoluble carrier is reacted with a mercapto group of the protein.

By reacting an insoluble carrier containing a functional group for immobilization with a fucose-binding protein of the present invention dissolved in a buffer, the fucose-binding protein of the present invention can be immobilized on the insoluble carrier, to produce the adsorbent of the present invention. The fucose-binding protein of the present invention may be used for the immobilization after, for example, dissolving the protein in an appropriate buffer. The buffer in which the fucose-binding protein of the present invention is dissolved is not limited. Examples of the buffer in which the fucose-binding protein of the present invention is dissolved include acetate buffer, phosphate buffer, 2-morpholinoethanesulfonic acid (MES) buffer, 4-(2-hydroxyethyl)-1-piperazineethanesulfonic acid (HEPES) buffer, and tris(hydroxymethyl)aminomethane (Tris) buffer; and commercially available buffers such as D-PBS(−) (manufactured by FUJIFILM Wako Pure Chemical Corporation). For the purpose of increasing the efficiency of the immobilization reaction, an appropriate additive such as an inorganic salt including sodium chloride; and/or a surfactant including polyoxyethylene sorbitan monolaurate (Tween 20); may be added to the buffer. The reaction temperature and the pH for the immobilization of the fucose-binding protein of the present invention on the insoluble carrier may be appropriately set depending on conditions such as reactivity of the active functional group and/or stability of the fucose-binding protein of the present invention. The reaction temperature may be, for example, 0° C. to 50° C. The pH may be, for example, pH 4 to pH 10. In particular, preferably, from the viewpoint of suppressing deactivation of the fucose-binding protein of the present invention, the reaction temperature may be 15° C. to 40° C., and the pH may be pH 5 to pH 9.

The amount of the fucose-binding protein of the present invention immobilized on the insoluble carrier may be appropriately set depending on conditions such as the binding capacity between the substance containing a fucose-containing sugar chain and the fucose-binding protein of the present invention. The amount of the fucose-binding protein of the present invention immobilized on the insoluble carrier may be preferably 0.01 mg to 50 mg, more preferably 0.05 mg to 30 mg per 1 mL of the insoluble carrier. The amount of the fucose-binding protein of the present invention immobilized on the insoluble carrier can be controlled by adjusting the amount of the fucose-binding protein of the present invention used for the immobilization reaction, and the amount of the active functional group introduced to the insoluble carrier. The amount of the fucose-binding protein of the present invention immobilized on the insoluble carrier can be calculated by collecting the immobilization reaction mixture and the washing solution after the reaction, determining the amount of unreacted fucose-binding protein of the present invention, and subtracting the amount of the unreacted fucose-binding protein of the present invention from the amount of the fucose-binding protein used for the immobilization reaction.

As described above, the insoluble carrier may preferably have a hydrophilic polymer covalently immobilized thereon from the viewpoint of suppressing non-specific adsorption of substances. Thus, in the production of the adsorbent of the present invention, before the introduction of the functional group for immobilization of the fucose-binding protein of the present invention in Step X, a hydrophilic polymer may be covalently immobilized on the insoluble carrier. Examples of the method of covalently immobilizing the hydrophilic polymer on the insoluble carrier include common methods for forming a covalent bond. Examples of the method for forming a covalent bond include a method in which a hydroxyl group on the surface of the insoluble carrier is reacted with an epoxy-containing compound such as epichlorohydrin, ethylene glycol diglycidyl ether, or 1,4-butanediol diglycidyl ether under basic conditions to introduce an epoxy group to the insoluble carrier, and then the epoxy group is reacted with a hydroxyl group of the hydrophilic polymer under basic conditions.

Since the adsorbent of the present invention comprises the fucose-binding protein of the present invention, the adsorbent is capable of adsorbing cells containing a fucose-containing sugar chain such as a sugar chain containing a structure composed of Fucα1-2Galβ1-3GlcNAc and/or Fucα1-2Galβ1-3GalNAc, and of adsorbing a sugar chain and/or glycoconjugates containing the structure.

The fucose-binding protein of the present invention can be used for, for example, adsorption of a substance containing a fucose-containing sugar chain. Thus, the method of the present invention may be a method of adsorbing a substance containing a fucose-containing sugar chain using the fucose-binding protein of the present invention. More specifically, the method of the present invention may be a method of adsorbing a substance containing a fucose-containing sugar chain, the method comprising a step of bringing the fucose-binding protein of the present invention into contact with the substance containing a fucose-containing sugar chain. This step is also referred to as "contacting step".

By the adsorption of the substance containing a fucose-containing sugar chain, for example, the substance containing a fucose-containing sugar chain can be separated. More specifically, by the adsorption of the substance containing a fucose-containing sugar chain, for example, the substance containing a fucose-containing sugar chain can be separated from another substance (that is, a substance other than the substance containing a fucose-containing sugar chain). Thus, one aspect of the method of the present invention may be, for example, a method of separating a substance containing a fucose-containing sugar chain. Further, one aspect of the contacting step may be, for example, a step of bringing the fucose-binding protein of the present invention into contact with a mixture comprising a substance containing a fucose-containing sugar chain and another substance.

By the adsorption of the substance containing a fucose-containing sugar chain, for example, the substance containing a fucose-containing sugar chain can be purified. More specifically, by the adsorption of the substance containing a fucose-containing sugar chain, for example, the substance containing a fucose-containing sugar chain can be collected from a mixture comprising the substance containing a fucose-containing sugar chain and another substance, to achieve purification of the substance containing a fucose-containing sugar chain. Thus, one aspect of the method of the present invention may be, for example, a method of purifying a substance containing a fucose-containing sugar chain. By the purification of the substance containing a fucose-containing sugar chain, the substance containing a fucose-containing sugar chain may be obtained. Thus, one aspect of the method of the present invention may be, for example, a method of producing a substance containing a fucose-containing sugar chain.

By the adsorption of the substance containing a fucose-containing sugar chain, for example, another substance can be purified. More specifically, by the adsorption of the substance containing a fucose-containing sugar chain, for example, the substance containing a fucose-containing sugar chain can be removed from a mixture comprising the substance containing a fucose-containing sugar chain and another substance, to achieve purification of the other substance. Thus, one aspect of the method of the present invention may be, for example, a method of purifying another substance. By the purification of the substance containing a fucose-containing sugar chain, another substance may be obtained. Thus, one aspect of the method of the present invention may be, for example, a method of producing another substance.

The substance containing a fucose-containing sugar chain and the other substance may be appropriately selected depending on, for example, the type of the fucose-containing sugar chain to which the fucose-binding protein of the present invention has binding affinity.

The substance containing a fucose-containing sugar chain is not limited as long as it contains a fucose-containing sugar chain to which the fucose-binding protein of the present invention has binding affinity. In other words, the fucose-containing sugar chain contained in the substance containing a fucose-containing sugar chain is not limited as long as the fucose-binding protein of the present invention has binding affinity thereto. Particular examples of the substance containing a fucose-containing sugar chain include substances containing a sugar chain containing an H type 1 sugar chain structure, an H type 3 sugar chain structure, a Lewis Y sugar chain structure, and/or a Lewis b sugar chain structure, such as substances containing H type 1 sugar chain, H type 3 sugar chain, Lewis Y sugar chain, and/or Lewis b sugar chain. More particular examples of the substance containing a fucose-containing sugar chain include substances containing a sugar chain containing a structure composed of $Fuc\alpha1$-$2Gal\beta1$-3GlcNAc and/or $Fuc\alpha1$-$2Gal\beta1$-3GalNAc, such as substances containing H type 1 sugar chain and/or H type 3 sugar chain. The substance containing a fucose-containing sugar chain may be either a fucose-containing sugar chain itself or a substance containing a fucose-containing sugar chain bound to another structure. Specific examples of the substance containing a fucose-containing sugar chain include cells containing a fucose-containing sugar chain. Specific examples of the substance containing a fucose-containing sugar chain also include fucose-containing sugar chains themselves, and glycoconjugates containing a fucose-containing sugar chain. Specific examples of the glycoconjugates containing a fucose-containing sugar chain include proteins bound to a fucose-containing sugar chain(s), and lipids bound to a fucose-containing sugar chain(s).

The other substance is not limited as long as its degree of binding to the fucose-binding protein of the present invention is sufficiently low. Examples of the other substance include substances not containing the fucose-containing sugar chain. The substances not containing the fucose-containing sugar chain are not limited as long as they contain no fucose-containing sugar chain to which the fucose-binding protein of the present invention has binding affinity. The substances not containing the fucose-containing sugar chain may or may not contain a fucose-containing sugar chain other than fucose-containing sugar chains to which the fucose-binding protein of the present invention has binding affinity. Particular examples of the substances not containing the fucose-containing sugar chain include substances containing no sugar chain containing a structure composed of $Fuc\alpha1$-$2Gal\beta1$-3GlcNAc and/or $Fuc\alpha1$-$2Gal\beta1$-3GalNAc. More particular examples of the substances not containing the fucose-containing sugar chain include substances containing none of sugar chains containing structures composed of $Fuc\alpha1$-$2Gal\beta1$-3GlcNAc and $Fuc\alpha1$-$2Gal\beta1$-3GalNAc, such as substances containing neither H type 1 sugar chain nor H type 3 sugar chain. More particular examples of the substances not containing the fucose-containing sugar chain include substances containing none of sugar chains containing an H type 1 sugar chain structure, an H type 3 sugar chain structure, a Lewis Y sugar chain structure, and a Lewis b sugar chain structure, such as substances containing none of H type 1 sugar chain, H type 3 sugar chain, Lewis Y sugar chain, and Lewis b sugar chain. Specific examples of the substances not containing the fucose-containing sugar chain include cells not containing a fucose-containing sugar chain.

The fucose-binding protein of the present invention can be used, for example, in the form of the adsorbent of the present invention for adsorption of a substance containing a fucose-containing sugar chain. Specific examples of the method of the present invention are described below with reference to cases where the fucose-binding protein of the present invention is used in the form of the adsorbent of the present invention. However, the description is applicable mutatis mutandis also to cases where the fucose-binding protein of the present invention is used in another form.

The adsorbent of the present invention can be used in a form in which the adsorbent is packed in a column, for adsorption of a substance containing a fucose-containing sugar chain. Thus, in the method of the present invention, for example, a column packed with the adsorbent of the present invention may be used.

The adsorbent of the present invention can be used for, for example, separation of cells. More specifically, the adsorbent of the present invention can be used for, for example, separation of cells contained in a cell mixture. The method of separating cells using the adsorbent of the present invention is also referred to as "cell separation method of the present invention".

The cell separation method of the present invention may be, for example, a method of separating cells, the method comprising the steps of: bringing the adsorbent of the present invention into contact with a cell mixture; and separating cells bound to the adsorbent from cells not bound to the adsorbent.

The cell mixture may be a mixture containing first cells and second cells.

The first cells are each a cell to be bound to the adsorbent. Examples of the first cells include cells corresponding to the above-described substance containing a fucose-containing sugar chain. Thus, examples of the first cells include cells containing a fucose-containing sugar chain. Particular examples of the cells containing a fucose-containing sugar chain include substances containing a sugar chain containing an H type 1 sugar chain structure, an H type 3 sugar chain structure, a Lewis Y sugar chain structure, and/or a Lewis b sugar chain structure. More particular examples of the cells containing a fucose-containing sugar chain include cells containing a sugar chain containing a structure composed of $Fuc\alpha1$-$2Gal\beta1$-3GlcNAc and/or $Fuc\alpha1$-$2Gal\beta1$-3GalNAc. Specific examples of the cells containing a fucose-containing sugar chain include undifferentiated cells and cancer cells. Examples of the undifferentiated cells include human iPS cells and human ES cells. Examples of the cancer cells include: human embryonal carcinoma cells such as 2102Ep and NT2/D1; human lung adenocarcinoma cells such as PC-9; human pancreatic cancer cells such as Capan-1; and human colon cancer cells such as HT29. Any of these cells may be, for example, a cell containing a sugar chain containing a structure composed of Fucα1-2Galβ1-3GlcNAc and/or Fucα1-2Galβ1-3GalNAc. The number of types of the first cells contained in the cell mixture is not limited. One type, or two or more types of first cells may be contained in the cell mixture.

The second cells are each a cell not to be bound to the adsorbent. Examples of the second cells include cells corresponding to the above-described other substance. Thus, examples of the second cells include cells not containing a fucose-containing sugar chain. Particular examples of the cells not containing the fucose-containing sugar chain include cells containing none of sugar chains containing structures composed of Fucα1-2Galβ1-3GlcNAc and Fucα1-2Galβ1-3GalNAc. More particular examples of the cells not containing the fucose-containing sugar chain include substances containing none of sugar chains containing an H type 1 sugar chain structure, an H type 3 sugar chain structure, a Lewis Y sugar chain structure, and a Lewis b sugar chain structure. Specific examples of the cells not containing the fucose-containing sugar chain include differentiated cells and non-cancerous cells. Examples of the differentiated cells include cells generated by differentiation from undifferentiated cells such as human iPS cells or human ES cells. Specific examples of the cells not containing the fucose-containing sugar chain also include cancer cells not containing a fucose-containing sugar chain. Specific examples of the cancer cells not containing the fucose-containing sugar chain include cancer cells other than those exemplified as the first cells, which cancer cells contain no fucose-containing sugar chain. Any of these cells may be, for example, a cell containing none of sugar chains containing structures composed of Fucα1-2Galβ1-3GlcNAc and Fucα1-2Galβ1-3GalNAc. Any of these cells may also be, for example, a cell containing none of sugar chains containing an H type 1 sugar chain structure, an H type 3 sugar chain structure, a Lewis Y sugar chain structure, and a Lewis b sugar chain structure. The number of types of the second cells contained in the cell mixture is not limited. One type, or two or more types of second cells may be contained in the cell mixture.

By bringing the adsorbent of the present invention into contact with the cell mixture, for example, the first cells may be selectively bound to the adsorbent, to separate the cells. Thus, for example, the cells bound to the adsorbent may be the first cells, and the cells not bound to the adsorbent may be the second cells.

In the cell separation method of the present invention, cells bind to the adsorbent. Therefore, the method enables more efficient separation of the cells compared to methods in which cells are separated using a fucose-binding protein of the present invention not immobilized on the adsorbent, such as a method in which a fluorescently labelled fucose-binding protein of the present invention is brought into contact with a cell mixture, followed by separating the cells by combination of a flow cytometer and a cell sorter.

The method of bringing the adsorbent of the present invention into contact with the cell mixture is not limited. Examples of the method of bringing the adsorbent of the present invention into contact with the cell mixture include a method in which the adsorbent is added to the cell mixture, and then the resulting mixture is shaken for a predetermined time, and a method in which the adsorbent is packed into a column and then brought into contact with the cells. In particular, preferably, in expectation of preventing re-release of the cells bound to the adsorbent, and avoiding damage of the cells due to excessive contact with the adsorbent, the adsorbent may be packed into a column, and may then be brought into contact with the cells. The separation of the cells bound to the adsorbent from the cells not bound to the adsorbent can be carried out by, for example, separating the adsorbent to which the cells are bound, from the non-adsorbed fraction containing the cells not bound to the adsorbent. For example, in cases where the adsorbent is added to the cell mixture, the adsorbent added can be separated from the cell mixture, to separate the adsorbent from the non-adsorbed fraction. Further, for example, in cases where the adsorbent is packed into a column and then brought into contact with the cells, the cell mixture may be passed through the column packed with the adsorbent, to separate the adsorbent from the non-adsorbed fraction. The cells bound to the adsorbent (for example, first cells) can be eluted as appropriate from the adsorbent, and collected as an eluted fraction. The cells not bound to the adsorbent (for example, second cells) can be collected as appropriate as a non-adsorbed fraction. By the cell separation method of the present invention, for example, the first cells may be purified, or the first cells may be obtained. Thus, for example, one aspect of the cell separation method of the present invention may be a method of purifying the first cells, or may be a method of producing the first cells. By the cell separation method of the present invention, for example, the second cells may be purified, or the second cells may be obtained. Thus, for example, one aspect of the cell separation method of the present invention may be a method of purifying the second cells, or may be a method of producing the second cells.

The cell mixture may be prepared as, for example, a cell suspension, and may be used for the cell separation method of the present invention. The solution for the preparation of the cell suspension may preferably be a solution in which a component(s) effective for preventing cell death and cell aggregation is/are added. Examples of the solution for the preparation of the cell suspension include a commercially available MACS buffer (PBS supplemented with 0.5% (w/v) bovine serum albumin (hereinafter simply referred to as BSA) and 2 mM ethylenediaminetetraacetic acid (hereinafter simply referred to as EDTA)). In this case, BSA is expected to produce an effect which reduces damage of the cells during separation of the cells, and which suppresses non-specific adsorption of the cells to the adsorbent, and EDTA is expected to produce an effect which prevents aggregation of the cells.

H type 1 sugar chain having the structure composed of "Fucα1-2Galβ1-3GlcNAc" and H type 3 sugar chain having the structure composed of "Fucα1-2Galβ1-3GalNAc" are sugar chains known as undifferentiation markers specifically present in undifferentiated cells such as human iPS cells and ES cells (Non-patent Document 3). Thus, by the cell separation method of the present invention, for example, undifferentiated cells can be selectively removed from a cell mixture containing the undifferentiated cells and differentiated cells, to purify the differentiated cells. Cancer cells, for example, human embryonal carcinoma cells such as 2102Ep and NT2/D1; human lung adenocarcinoma cells such as PC-9; human pancreatic cancer cells such as Capan-1; and human colon cancer cells such as HT29; are known to contain H type 1 sugar chain and/or H type 3 sugar chain (for example, J. Biomark. 2013:960862. doi:10.1155/2013/960862). Thus, by the cell separation method of the present invention, for example, these cancer cells can be separated by selective adsorption of these cancer cells to the adsorbent. By the separation of the cancer cells, for example, the cancer cells in the cell mixture can be detected. Examples of the detection of the cancer cells include identification of the presence or absence of the cancer cells, and identification of the degree of presence (that is, the abundance) of the cancer cells. Examples of the cell mixture used for the separation or detection of the cancer cells include samples containing cells obtained from a subject. Thus, by detecting cancer cells in a sample containing cells obtained from a subject, for example, whether or not the subject is suffering from cancer can be diagnosed.

In cases where the amount of the fucose-binding protein of the present invention immobilized on the adsorbent of the present invention is 0.05 mg to 30 mg per 1 mL of the adsorbent, the adsorbent is capable of binding not less than 1 million cells containing a fucose-containing sugar chain such as a sugar chain containing a structure composed of "Fucα1-2Galβ1-3GlcNAc and/or Fucα1-2Galβ1-3Gal-NAc". For example, in regenerative medicine using cardiomyocytes induced from human iPS cells, 1 billion clinical-grade cardiomyocytes per individual are required. Therefore, the regenerative medicine requires a technique that enables complete removal of 1 million undifferentiated stem cells when contamination with undifferentiated cells at 0.1% is assumed, or 10 million undifferentiated stem cells when contamination with undifferentiated cells at 1% is assumed. Even in cases where undifferentiated cells contained in such a large amount of cells are to be removed, the undifferentiated cells can be efficiently removed in a short time by using a small amount (for example, 1 mL in cases where 1 million undifferentiated cells are contained, or 10 mL in cases where 10 million undifferentiated cells are contained) of the adsorbent of the present invention. Further, for example, in cases of induction of blood cells from undifferentiated stem cells, 10 billion to 100 billion cells per patient are required. Even when contamination with undifferentiated stem cells at 1% is assumed, the undifferentiated cells remaining in the blood cells can be separated by using 100 mL to 1000 mL of the adsorbent of the present invention.

Further, even for purification of a large amount of desired differentiated cells, the cell separation method of the present invention is extremely effective compared to a method using combination of flow cytometry and a cell sorter, and a method using magnetic beads to which an antibody against a cell surface marker protein is bound, which are existing cell separation techniques; and a method using BC2LCN lectin fused with a toxin, which is a known technique for removing undifferentiated cells (JP 2014-126146 A), since the cell separation method of the present invention is capable of carrying out the process of removing undifferentiated cells in a very short time of about 5 minutes to 30 minutes.

The adsorbent of the present invention can be used for purification of a substance containing a fucose-containing sugar chain. The method of purifying a substance containing a fucose-containing sugar chain using the adsorbent of the present invention is also referred to as "purification method of the present invention".

The purification method of the present invention may be a method of purifying a substance containing a fucose-containing sugar chain, the method comprising the steps of: bringing the adsorbent of the present invention into contact with the substance containing a fucose-containing sugar chain; and eluting the substance bound to the adsorbent.

The substance containing a fucose-containing sugar chain is as described above. In particular, the substance containing a fucose-containing sugar chain may be a substance containing a sugar chain containing fucose, such as H type 1 sugar chain, H type 3 sugar chain, Lewis Y sugar chain, or Lewis b sugar chain. Further, in particular, the substance containing a fucose-containing sugar chain may be the fucose-containing sugar chain and/or glycoconjugates containing the fucose-containing sugar chain.

The method of bringing the adsorbent of the present invention into contact with the substance containing a fucose-containing sugar chain is not limited. Examples of the method of bringing the adsorbent of the present invention into contact with the substance containing a fucose-containing sugar chain include a method in which an adsorbent equilibrated with a buffer at pH 5 to pH 9, preferably pH 6 to pH 8, is brought into contact with a solution containing the substance containing a fucose-containing sugar chain that has not been separated or purified. In particular, from the viewpoint of enabling efficient purification, the adsorbent is preferably packed into a column, and then brought into contact with the substance containing a fucose-containing sugar chain. Examples of the buffer used for the adsorption of the substance containing a fucose-containing sugar chain to the adsorbent of the present invention (for example, a buffer used for equilibration of the adsorbent, used for preparation of a solution containing the substance containing a fucose-containing sugar chain, or used as the mobile phase for passing the solution through a column) include acetate buffer, phosphate buffer, 2-morpholinoethanesulfonic acid (MES) buffer, 4-(2-hydroxy-ethyl)-1-piperazineethanesulfonic acid (HEPES) buffer, and tris(hydroxymethyl)aminomethane (Tris) buffer. An appropriate additive(s), such as an inorganic salt including sodium chloride; and/or a surfactant including polyoxyethylene sorbitan monolaurate (Tween 20); may be added to the buffer.

The substance containing a fucose-containing sugar chain adsorbed on the adsorbent of the present invention can be eluted from the adsorbent by using, for example, a buffer containing L-fucose. Examples of the buffer containing L-fucose include buffers prepared by adding L-fucose to the above-described buffer used for the adsorption of the substance containing a fucose-containing sugar chain to the adsorbent of the present invention. The concentration of L-fucose in the buffer may be, for example, 0.1 mM to 1 M, preferably 1 mM to 100 mM.

By carrying out the purification method of the present invention as described above, a substance containing a fucose-containing sugar chain can be purified. Further, by the purification method of the present invention, for example, a substance containing a fucose-containing sugar chain may be obtained. Thus, one aspect of the purification method of the present invention may be, for example, a method of producing a substance containing a fucose-containing sugar chain.

In cases where a substance containing a fucose-containing sugar chain is to be removed from a solution containing the substance containing a fucose-containing sugar chain that has not been separated or purified, the step of bringing the adsorbent of the present invention into contact with the substance containing a fucose-containing sugar chain may be carried out. By this, a solution from which the substance containing a fucose-containing sugar chain has been removed can be obtained. The solution from which the substance containing a fucose-containing sugar chain has been removed can be collected as appropriate as a non-adsorbed fraction.

EXAMPLES

The present invention is described below more concretely with reference to non-limiting Examples.

Comparative Example 1 Production of Recombinant BC2LCN(155)cys and Evaluation of Productivity Comparative Example 1 is related to production of the recombinant BC2LCN(155)cys by addition of a polyhistidine sequence and a cysteine-containing oligopeptide sequence to the amino acid sequence of the recombinant BC2LCN of SEQ ID NO: 1, which is composed of 155 amino acid residues, and evaluation of the productivity thereof.

(1) Preparation of Expression Vector pET-BC2LCN(155)cys and Recombinant *E. coli* BL21 (DE3)/pET-BC2LCN(155) cys The expression vector pET-BC2LCN(155)cys is an expression vector for expression of the recombinant BC2LCN(155)cys. The amino acid sequence of the recombinant BC2LCN(155)cys is SEQ ID NO: 32, wherein the sequence from position 5 to position 10 corresponds to the polyhistidine sequence; the sequence from position 15 to position 169 corresponds to the amino acid sequence of SEQ ID NO: 1 (which is the same as the amino acid sequence of the region from position 2 to position 156 of GenPept accession number: WP_006490828); and the sequence from position 170 to position 174 corresponds to the oligopeptide sequence containing a cysteine residue. The expression vector pET-BC2LCN(155)cys has the same nucleotide sequence as the plasmid pET-BC2LCNcys disclosed in JP 2018-000038 A, and was prepared by the method disclosed in this publication. Subsequently, *E. coli* BL21 (DE3) was transformed using the expression vector pET-BC2LCN(155) cys, to prepare the recombinant *E. coli* BL21 (DE3)/pET-BC2LCN(155)cys.

(2) Production of Recombinant BC2LCN(155)cys Using Recombinant *E. coli*

The recombinant *E. coli* BL21 (DE3)/pET-BC2LCN(155) cys prepared in (1) of Comparative Example 1 was inoculated to 100 mL of TB medium supplemented with 50 g/mL kanamycin, and shake culture was aerobically carried out at 30° C. overnight to perform preculture. The composition of TB medium is shown in Table 1.

[Table 1]

TABLE 1

| Component | Concentration |
| --- | --- |
| Yeast extract | 24 g/L |
| Tryptone | 12 g/L |
| Glycerol | 8 mL/L |
| Dipotassium hydrogen phosphate | 9.4 g/L |
| Potassium dihydrogen phosphate | 2.2 g/L |

Thereafter, the preculture broth was inoculated at 0.5% (v/v) to 100 mL of TB medium supplemented with 50 μg/mL kanamycin, and shake culture was aerobically carried out at 30° C. for 2 hours. At the time when the turbidity (O. D. 600) of the culture broth became about 2 to 5, 20 μL of 0.5M IPTG was added to the culture broth, and the culture temperature was changed to 20° C. Thereafter, shake culture was aerobically carried out overnight to produce the recombinant BC2LCN(155)cys. Subsequently, bacterial cells were collected from the culture broth by centrifugation, and 10.8 mL of the extraction solution having the composition shown in Table 2 was added thereto, followed by stirring the resulting mixture with shaking at room temperature for 30 minutes. The additives shown in Table 3 were then added to the mixture, and the resulting mixture was stirred with shaking at room temperature for 30 minutes, and then at 4° C. overnight, followed by performing centrifugation and collecting the supernatant, to collect a soluble protein extract containing the recombinant BC2LCN(155)cys. The soluble protein extract containing the recombinant BC2LCN(155) cys collected was filtered through a 0.2-μm filter, and then used for the later-described purification by nickel chelate affinity chromatography.

[Table 2]

TABLE 2

| Component | Volume |
| --- | --- |
| 0.5M Tris buffer (pH 8.0) | 25 mL |
| Water | 162.5 mL |
| Sodium chloride | 5.85 g |
| 1M Aqueous magnesium sulfate solution | 1.5 mL |
| Benzonase (manufactured by Merck Millipore; purity, 90% or more) | 2.5 μL |
| 5% (w/v) Aqueous lysozyme solution | 250 μL |
| 20% (w/w) Aqueous Triton X-100 solution | 6.3 mL |

[Table 3]

TABLE 3

| Component | Volume |
| --- | --- |
| CTAB (cetyltrimethylammonium bromide) | 0.10 g |
| Sodium deoxycholate | 0.01 g |

(3) Purification of Recombinant BC2LCN(155)cys and Evaluation of Productivity

The recombinant BC2LCN(155)cys was purified from the soluble protein extract collected in (2) of Comparative Example 1 by nickel chelate affinity chromatography using His-Bind Resin (manufactured by Merck Millipore). More specifically, the recombinant BC2LCN(155)cys was purified by the methods described in the following (Comp. 1-1) to (Comp. 1-6).

(Comp. 1-1) A column (Poly-Prep Chromatography Column, manufactured by BioRad) was packed with 2 mL of His-Bind Resin, and then equilibrated with 10 mL of Buffer A (20 mM Tris buffer (pH 8.3) supplemented with 500 mM sodium chloride and 20 mM imidazole).

(Comp. 1-2) To the column equilibrated with Buffer A in (Comp. 1-1), 10 mL of the soluble protein extract containing the recombinant BC2LCN(155)cys was applied. (Comp. 1-3) To the column to which the soluble protein extract was applied in (Comp. 1-2), 10 mL of Buffer A was applied twice, to wash away substances not bound to the His-Bind Resin.

(Comp. 1-4) To the column washed with Buffer A in (Comp. 1-3), 10 mL of a mixed solution of Buffer A and Buffer B (20 mM Tris buffer (pH 9.0) supplemented with 500 mM sodium chloride and 250 mM imidazole) (Buffer A: Buffer B=80:20, v/v), was applied to wash the His-Bind Resin while collecting the washing solution. The washing solution collected was used as "20% B eluted fraction" in the later-described analysis by the SDS-PAGE method.

(Comp. 1-5) To the column washed with the mixed solution of Buffer A and Buffer B in (Comp. 1-4), 10 mL of a mixed solution of Buffer A and Buffer B (Buffer A: Buffer B=50:50, v/v) was applied to wash the His-Bind Resin while collecting the washing solution. The washing solution collected was used as "50% B eluted fraction" in the later-described analysis by the SDS-PAGE method.

(Comp. 1-6) To the column washed with the mixed solution of Buffer A and Buffer B in (Comp. 1-5), 10 mL of Buffer B was applied twice to wash the His-Bind Resin while collecting the washing solution. The washing solution collected was used as "100% B eluted fraction" in the later-described analysis by the SDS-PAGE method.

The "20% B eluted fraction", "50% B eluted fraction", and "100% B eluted fraction" obtained in (Comp. 1-4) to (Comp. 1-6) were analyzed by the SDS-PAGE method. The results are shown in FIG. 1. In FIG. 1, "M" represents molecular weight markers; "127" represents the later-described fucose-binding protein 127 produced in Example 2; "127G36C" represents the later-described fucose-binding protein 127G36C produced in Example 4; "129" represents the later-described fucose-binding protein 129 produced in Example 1; "129G36C" represents the later-described fucose-binding protein 129G36C produced in Example 3; and "155" represents the recombinant BC2LCN(155)cys produced in the present Comparative Example. "20% B", "50% B", and "100% B" represent the "20% B eluted fraction", "50% B eluted fraction", and "100% B eluted fraction", respectively, obtained in (3) of Comparative Example 1. In the analysis by the SDS-PAGE method, a commercially available 15% gel (manufactured by ATTO) was used, and a sample solution for SDS-PAGE analysis prepared from each eluted fraction by the method described below in (Comp. 1-7) was used.

(Comp. 1-7) To the eluted fraction, an aqueous solution of 100 mM tris(2-carboxyethyl) phosphine hydrochloride (TCEP, prepared from a product manufactured by FUJIFILM Wako Pure Chemical Corporation) was added to a final concentration of 0.48 μM, and the resulting mixture was allowed to react at room temperature for 2 hours. With 50 μL of the solution after the reaction, 50 μL of 2×SDS sample buffer (Table 4) was mixed, and the resulting mixture was heated at 94° C. for 5 minutes. To a lane for SDS-PAGE, 10 μL of the resulting solution was applied, and analysis by the SDS-PAGE method was carried out.

[Table 4]

TABLE 4

| Component | Volume |
| --- | --- |
| 0.5M Tris buffer (pH 6.8) | 25 mL |
| 10% (w/v) aqueous sodium dodecyl sulfate solution | 40 mL |
| Sucrose | 10 g |
| Bromophenol blue | 10 mL |
| Water | Required amount* |

*After mixing components, water was added to a final volume of 100 mL.

As shown in FIG. 1, each of the "50% B eluted fraction" and the "100% B eluted fraction" of the recombinant BC2LCN(155)cys showed bands near the molecular weight (about 17 kDa) of the monomer of the recombinant BC2LCN(155)cys and near a molecular weight (about 34 kDa) presumably corresponding to the dimer. Since the band near the molecular weight presumably corresponding to the dimer was confirmed to be the dimer of BC2LCN(155)cys in the later-described Example 6, it became clear that those eluted fractions contain the desired recombinant BC2LCN (155)cys. Since the recombinant BC2LCN(155)cys contains the cysteine-containing oligopeptide added to the C-terminus, it was thought that the cysteine contained in the oligopeptide interacted to form disulfide bonds to generate dimers.

Subsequently, the "50% B eluted fraction" and the "100% B eluted fraction" containing the recombinant BC2LCN (155)cys were combined to provide a purified BC2LCN (155) solution, and the absorbance of the purified BC2LCN (155) solution at 280 nm was measured using a quartz cell with a 1-cm pathlength. The protein concentration in the purified BC2LCN(155) solution was calculated based on the molar absorption coefficient of the recombinant BC2LCN (155)cys, which was taken as 1.0. As a result of calculating the productivity of the recombinant BC2LCN(155)cys per 1-L culture broth based on the calculated protein concentration, the productivity was found to be 162 mg/L-culture broth.

The purified BC2LCN(155) solution obtained was dialyzed against D-PBS(−) (manufactured by FUJIFILM Wako Pure Chemical Corporation), and then its concentration was adjusted to an appropriate concentration using D-PBS(−). The solution was then used in the later-described analysis by the SDS-PAGE method, evaluation of the sugar-chain binding affinity, and production of an adsorbent.

Example 1 Production of Fucose-Binding Protein 129 and Evaluation of Productivity Example 1 is related to production of a fucose-binding protein (hereinafter referred to as fucose-binding protein 129) by adding an oligopeptide containing a polyhistidine sequence to the N-terminus, and adding an oligopeptide containing a cysteine residue to the C-terminus, of the amino acid sequence of the fucose-binding protein of SEQ ID NO: 2, which is composed of 129 amino acid residues, and evaluation of the productivity thereof.

(1) Preparation of Expression Vector pET-BC2LCN(129)cys and Recombinant *E. coli* BL21 (DE3)/pET-BC2LCN(129) cys The expression vector pET-BC2LCN(129)cys is an expression vector for expression of the fucose-binding protein 129. The amino acid sequence of the fucose-binding protein 129 is SEQ ID NO: 33, wherein the sequence from position 5 to position 10 corresponds to the polyhistidine sequence; the sequence from position 15 to position 143 corresponds to the amino acid sequence of SEQ ID NO: 2; and the sequence from position 144 to position 150 corresponds to the oligopeptide sequence containing a cysteine residue.

Preparation of the expression vector pET-BC2LCN(129) cys was carried out as follows based on the expression vector pET-BC2LCN(155)cys described in (1) of Comparative Example 1. First, using the expression vector pET-BC2LCN(155)cys described in (1) of Comparative Example 1 as a template, and using oligonucleotides having the sequences of SEQ ID NO: 48 and SEQ ID NO: 49 as PCR primers, PCR was carried out by the method disclosed in JP 2018-000038 A. Subsequently, using the PCR product as a template, and using oligonucleotides having the sequences of SEQ ID NO: 48 and SEQ ID NO: 50 as PCR primers, PCR was carried out by the same method. The resulting PCR product was digested with the restriction enzymes NcoI and XhoI, and then subjected to ligation reaction with the expression vector pET28a(+) (manufactured by Merck Mil-lipore) that had been similarly treated with the restriction enzymes. *E. coli* BL21 (DE3) was transformed using the ligation product, to obtain the recombinant *E. coli* BL21 (DE3)/pET-BC2LCN(129)cys. By the method disclosed in JP 2018-000038 A, the recombinant *E. coli* BL21 (DE3)/ pET-BC2LCN(129)cys obtained was cultured, and then the expression vector pET-BC2LCN(129)cys was obtained by extraction from the bacterial cells. As a result of confirma-tion of the nucleotide sequence by sequence analysis, it was confirmed that the expression vector pET-BC2LCN(129)cys contains the nucleotide sequence of SEQ ID NO: 17, which encodes the amino acid sequence of SEQ ID NO: 2.

(2) Production of Fucose-Binding Protein 129 Using Recombinant *E. coli*

Production of the fucose-binding protein 129 using the recombinant *E. coli* BL21 (DE3)/pET-BC2LCN(129)cys, and collection of the soluble protein extract, were carried out by the same method as in (2) of Comparative Example 1.

(3) Purification of Fucose-Binding Protein 129 and Evalu-ation of Productivity

Purification of the fucose-binding protein 129 from the soluble protein extract collected in (2) of Example 1 was carried out by the same method as in (3) of Comparative Example 1, to obtain "20% B eluted fraction", "50% B eluted fraction", and "100% B eluted fraction". The "20% B eluted fraction", "50% B eluted fraction", and "100% B eluted fraction" obtained were analyzed by the SDS-PAGE method according to the method described in (3) of Com-parative Example 1. The results are shown in FIG. 1. As shown in FIG. 1, each of the "50% B eluted fraction" and the "100% B eluted fraction" of "129" showed bands near the molecular weight (about 14 kDa) of the monomer of the fucose-binding protein 129 and near a molecular weight (about 28 kDa) presumably corresponding to the dimer. Since the band near the molecular weight presumably cor-responding to the dimer was confirmed to be the dimer of the fucose-binding protein 129 in the later-described Example 6, it became clear that those eluted fractions contain the desired fucose-binding protein 129. Since the fucose-binding pro-tein 129 contains the cysteine-containing oligopeptide added to the C-terminus, it was thought that the cysteine contained in the oligopeptide interacted to form disulfide bonds to generate dimers.

Subsequently, the "50% B eluted fraction" and the "100% B eluted fraction" containing the fucose-binding protein 129 were combined to provide a purified 129 solution, and the productivity of the fucose-binding protein 129 per 1-L culture broth was calculated according to the method described in (4) of Comparative Example 1. As a result, the productivity was found to be 475 mg/L-culture broth. The purified 129 solution obtained was dialyzed against D-PBS (−) (manufactured by FUJIFILM Wako Pure Chemical Cor-poration), and then its concentration was adjusted to an appropriate concentration using D-PBS(−). The solution was then used in the later-described analysis by the SDS-PAGE method, evaluation of the sugar-chain binding affinity, and production of an adsorbent.

Example 2 Production of Fucose-Binding Protein 127 and Evaluation of Productivity Example 2 is related to production of a fucose-binding protein (hereinafter referred to as fucose-binding protein 127) by adding an oligopeptide containing a polyhistidine sequence to the N-terminus, and adding an oligopeptide containing a cysteine residue to the C-terminus, of the amino acid sequence of the fucose-binding protein of SEQ ID NO: 3, which is composed of 127 amino acid residues, and evaluation of the productivity thereof.

(1) Preparation of Expression Vector pET-BC2LCN(127)cys and Recombinant *E. coli* BL21 (DE3)/pET-BC2LCN(127) cys The expression vector pET-BC2LCN(127)cys is an expression vector for expression of the fucose-binding pro-tein 127. The amino acid sequence of the fucose-binding protein 127 is SEQ ID NO: 34, wherein the sequence from position 5 to position 10 corresponds to the polyhistidine sequence; the sequence from position 15 to position 141 corresponds to the amino acid sequence of SEQ ID NO: 3; and the sequence from position 142 to position 148 corre-sponds to the oligopeptide sequence containing a cysteine residue.

The same method as described in (1) of Example 1 was carried out except that each oligonucleotide having the sequence of SEQ ID NO: 51 was used instead of each oligonucleotide having the sequence of SEQ ID NO: 49 described in (1) of Example 1, to prepare the desired expression vector pET-BC2LCN(127)cys, and to prepare the recombinant *E. coli* BL21 (DE3)/pET-BC2LCN(127)cys by transformation of *E. coli* BL21 (DE3) using the expression vector pET-BC2LCN(127)cys. As a result of confirmation of the nucleotide sequence by sequence analysis, it was con-firmed that the expression vector pET-BC2LCN(127)cys contains the nucleotide sequence of SEQ ID NO: 18, which encodes the amino acid sequence of SEQ ID NO: 3.

(2) Production of Fucose-Binding Protein 127 Using Recombinant *E. coli*

Production of the fucose-binding protein 127 using the recombinant *E. coli* BL21 (DE3)/pET-BC2LCN(127)cys, and collection of the soluble protein extract, were carried out by the same method as in (2) of Comparative Example 1.

(3) Purification of Fucose-Binding Protein 127 and Evalu-ation of Productivity

Purification of the fucose-binding protein 127 from the soluble protein extract collected in (2) of Example 2 was carried out by the same method as in (3) of Comparative Example 1, to obtain "20% B eluted fraction", "50% B eluted fraction", and "100% B eluted fraction". The "20% B eluted fraction", "50% B eluted fraction", and "100% B eluted fraction" obtained were analyzed by the SDS-PAGE method according to the method described in (3) of Com-parative Example 1. The results are shown in FIG. 1. As shown in FIG. 1, each of the "50% B eluted fraction" and the "100% B eluted fraction" of "127" showed bands near the molecular weight (about 14 kDa) of the monomer of the fucose-binding protein 127 and near a molecular weight (about 28 kDa) presumably corresponding to the dimer. Since the band near the molecular weight presumably cor-responding to the dimer was confirmed to be the dimer of the fucose-binding protein 127 in the later-described Example 6, it became clear that those eluted fractions contain the desired fucose-binding protein 127. Since the fucose-binding pro-tein 127 contains the cysteine-containing oligopeptide added to the C-terminus, it was thought that the cysteine contained in the oligopeptide interacted to form disulfide bonds to generate dimers.

Subsequently, the "50% B eluted fraction" and the "100% B eluted fraction" containing the fucose-binding protein 127 were combined to provide a purified 127 solution, and the productivity of the fucose-binding protein 127 per 1-L culture broth was calculated according to the method described in (3) of Comparative Example 1. As a result, the productivity was found to be 560 mg/L-culture broth. The purified 127 solution obtained was dialyzed against D-PBS (−), and then its concentration was adjusted to an appropriate concentration using D-PBS(−). The solution was then used in the later-described analysis by the SDS-PAGE method and production of an adsorbent.

Example 3 Production of Fucose-Binding Protein 129G36C and Evaluation of Productivity Example 3 is related to production of a fucose-binding protein (hereinafter referred to as fucose-binding protein 129G36C) by adding an oligopeptide containing a polyhistidine sequence to the N-terminus, and adding an oligopeptide containing a cysteine residue to the C-terminus, of the amino acid sequence of the fucose-binding protein of SEQ ID NO: 4 (amino acid sequence which is the same as SEQ ID NO: 2 except that the glycine residue at position 36 is substituted with a cysteine residue), which is composed of 129 amino acid residues, and evaluation of the productivity thereof.

(1) Preparation of Expression Vector pET-BC2LCN (129G36C)cys and Recombinant *E. coli* BL21 (DE3)/pET-BC2LCN(129G36C)cys The expression vector pET-BC2LCN(129G36C)cys is an expression vector for expression of the fucose-binding protein 129G36C. The amino acid sequence of the fucose-binding protein 129G36C is SEQ ID NO: 35, wherein the sequence from position 5 to position 10 corresponds to the polyhistidine sequence; the sequence from position 15 to position 143 corresponds to the amino acid sequence of SEQ ID NO: 4; and the sequence from position 144 to position 150 corresponds to the oligopeptide sequence containing a cysteine residue.

For preparation of the expression vector pET-BC2LCN (129G36C)cys, PCR was carried out by the method disclosed in JP 2018-000038 A using the expression vector pET-BC2LCN(129)cys in (1) of Example 1 as a template, and using oligonucleotides having the sequences of SEQ ID NO: 48 and SEQ ID NO: 52 as PCR primers. The resulting PCR product was digested with the restriction enzymes NcoI and PstI, and then subjected to ligation reaction with the expression vector pET-BC2LCN(129)cys described in (1) of Example 1 that had been similarly treated with the restriction enzymes. *E. coli* BL21 (DE3) was transformed using the ligation product, to obtain the recombinant *E. coli* BL21 (DE3)/pET-BC2LCN(129G36C)cys. By the method disclosed in JP 2018-000038 A, the recombinant *E. coli* BL21 (DE3)/pET-BC2LCN(129G36C)cys obtained was cultured, and then the expression vector pET-BC2LCN(129G36C)cys was obtained by extraction from the bacterial cells. As a result of confirmation of the nucleotide sequence by sequence analysis, it was confirmed that the expression vector pET-BC2LCN(129G36C)cys contains the nucleotide sequence of SEQ ID NO: 19, which encodes the amino acid sequence of SEQ ID NO: 4.

(2) Production of Fucose-Binding Protein 129G36C Using Recombinant *E. coli*

Production of the fucose-binding protein 129G36C using the recombinant *E. coli* BL21 (DE3)/pET-BC2LCN (129G36C)cys, and collection of the soluble protein extract, were carried out by the same method as in (2) of Comparative Example 1.

(3) Purification of Fucose-Binding Protein 129G36C and Evaluation of Productivity Purification of the fucose-binding protein 129G36C from the soluble protein extract collected in (2) of Example 3 was carried out by the same method as in (3) of Comparative Example 1, to obtain "20% B eluted fraction", "50% B eluted fraction", and "100% B eluted fraction". The "20% B eluted fraction", "50% B eluted fraction", and "100% B eluted fraction" obtained were analyzed by the SDS-PAGE method according to the method described in (3) of Comparative Example 1. The results are shown in FIG. 1. As shown in FIG. 1, each of the "50% B eluted fraction" and the "100% B eluted fraction" of "129G36C" showed bands near the molecular weight (about 14 kDa) of the monomer of the fucose-binding protein 129G36C and near a molecular weight (about 28 kDa) presumably corresponding to the dimer. Since the band near the molecular weight presumably corresponding to the dimer was confirmed to be the dimer of the fucose-binding protein 129G36C in the later-described Example 6, it became clear that those eluted fractions contain the desired fucose-binding protein 129G36C. Since the fucose-binding protein 129G36C contains the cysteine-containing oligopeptide added to the C-terminus, it was thought that the cysteine contained in the oligopeptide interacted to form disulfide bonds to generate dimers.

Subsequently, the "50% B eluted fraction" and the "100% B eluted fraction" containing the fucose-binding protein 129G36C were combined to provide a purified 129G36C solution, and the productivity of the fucose-binding protein 129G36C per 1-L culture broth was calculated according to the method described in (4) of Comparative Example 1. As a result, the productivity was found to be 428 mg/L-culture broth. The purified 129G36C solution obtained was dialyzed against D-PBS(−), and then its concentration was adjusted to an appropriate concentration using D-PBS(−). The solution was then used in the later-described analysis by the SDS-PAGE method and production of an adsorbent.

Example 4 Production of Fucose-Binding Protein 127G36C and Evaluation of Productivity Example 4 is related to production of a fucose-binding protein (hereinafter referred to as fucose-binding protein 127G36C) by adding an oligopeptide containing a polyhistidine sequence to the N-terminus, and adding an oligopeptide containing a cysteine residue to the C-terminus, of the amino acid sequence of the fucose-binding protein of SEQ ID NO: 5 (amino acid sequence which is the same as SEQ ID NO: 3 except that the glycine residue at position 36 is substituted with a cysteine residue), which is composed of 127 amino acid residues, and evaluation of the productivity thereof.

(1) Preparation of Expression Vector pET-BC2LCN (127G36C)cys and Recombinant *E. coli* BL21 (DE3)/pET-BC2LCN(127G36C)cys The expression vector pET-BC2LCN(127G36C)cys is an expression vector for expression of the fucose-binding protein 127G36C. The amino acid sequence of the fucose-binding protein 127G36C is SEQ ID NO: 36, wherein the sequence from position 5 to position 10 corresponds to the polyhistidine sequence; the sequence from position 15 to position 141 corresponds to the amino acid sequence of SEQ ID NO: 5; and the sequence from position 142 to position 148 corresponds to the oligopeptide sequence containing a cysteine residue.

The method described in (1) of Example 3 was carried out using oligonucleotides having the sequences of SEQ ID NO: 48 and SEQ ID NO: 52, to prepare the desired expression vector pET-BC2LCN(127G36C)cys, and to prepare the recombinant *E. coli* BL21 (DE3)/pET-BC2LCN(127)cys by transformation of *E. coli* BL21 (DE3) using the expression vector pET-BC2LCN(127G36C)cys. As a result of confirmation of the nucleotide sequence by sequence analysis, it was confirmed that the expression vector pET-BC2LCN (127G36C)cys contains the nucleotide sequence of SEQ ID NO: 20, which encodes the amino acid sequence of SEQ ID NO: 5.

(2) Production of Fucose-Binding Protein 127G36C Using Recombinant E. coli

Production of the fucose-binding protein 127G36C using the recombinant E. coli BL21 (DE3)/pET-BC2LCN (127G36C)cys, and collection of the soluble protein extract, were carried out by the same method as in (2) of Comparative Example 1.

(3) Purification of Fucose-Binding Protein 127G36C and Evaluation of Productivity Purification of the fucose-binding protein 127G36C from the soluble protein extract collected in (2) of Example 4 was carried out by the same method as in (3) of Comparative Example 1, to obtain "20% B eluted fraction", "50% B eluted fraction", and "100% B eluted fraction". The "20% B eluted fraction", "50% B eluted fraction", and "100% B eluted fraction" obtained were analyzed by the SDS-PAGE method according to the method described in (3) of Comparative Example 1. The results are shown in FIG. 1. As shown in FIG. 1, each of the "50% B eluted fraction" and the "100% B eluted fraction" of "127G36C" showed bands near the molecular weight (about 14 kDa) of the monomer of the fucose-binding protein 127G36C and near a molecular weight (about 28 kDa) presumably corresponding to the dimer. Since the band near the molecular weight presumably corresponding to the dimer was confirmed to be the dimer of the fucose-binding protein 127G36C in the later-described Example 6, it became clear that those eluted fractions contain the desired fucose-binding protein 127G36C. Since the fucose-binding protein 127G36C contains the cysteine-containing oligopeptide added to the C-terminus, it was thought that the cysteine contained in the oligopeptide interacted to form disulfide bonds to generate dimers.

Subsequently, the "50% B eluted fraction" and the "100% B eluted fraction" containing the fucose-binding protein 127G36C were combined to provide a purified 127G36C solution, and the productivity of the fucose-binding protein 127G36C per 1-L culture broth was calculated according to the method described in (4) of Comparative Example 1. As a result, the productivity was found to be 465 mg/L-culture broth. The purified 127G36C solution obtained was dialyzed against D-PBS(−), and then its concentration was adjusted to an appropriate concentration using D-PBS(−). The solution was then used in the later-described analysis by the SDS-PAGE method and production of an adsorbent.

Example 5 Production of Fucose-Binding Protein 126 and Evaluation of Productivity Example 5 is related to production of a fucose-binding protein (hereinafter referred to as fucose-binding protein 126) by adding an oligopeptide containing a polyhistidine sequence to the N-terminus of the amino acid sequence of the fucose-binding protein of SEQ ID NO: 6, which is composed of 126 amino acid residues, and evaluation of the productivity thereof.

(1) Preparation of Expression Vector pET-BC2LCN(126) and Recombinant E. coli BL21 (DE3)/pET-BC2LCN(126)

The expression vector pET-BC2LCN(126) is an expression vector for expression of the fucose-binding protein 126. The amino acid sequence of the fucose-binding protein 126 is SEQ ID NO: 37, wherein the sequence from position 5 to position 10 corresponds to the polyhistidine sequence, and the sequence from position 15 to position 140 corresponds to the amino acid sequence of SEQ ID NO: 6.

Preparation of the expression vector pET-BC2LCN(126) was carried out as follows based on the expression vector pET-BC2LCN(155)cys described in (1) of Comparative Example 1. Using the expression vector pET-BC2LCN(155) cys described in (1) of Comparative Example 1 as a template, and using oligonucleotides having the sequences of SEQ ID NO: 48 and SEQ ID NO: 53 as PCR primers, PCR was carried out by the method disclosed in JP 2018-000038 A. The resulting PCR product was digested with the restriction enzymes PstI and XhoI, and then subjected to ligation reaction with the expression vector pET-BC2LCN(155)cys of Comparative Example 1 that had been similarly treated with the restriction enzymes, to prepare the expression vector pET-BC2LCN(126). E. coli BL21 (DE3) was transformed using the expression vector pET-BC2LCN(126), to obtain the recombinant E. coli BL21 (DE3)/pET-BC2LCN (126). As a result of confirmation of the nucleotide sequence by sequence analysis, it was confirmed that the expression vector pET-BC2LCN(126) contains the nucleotide sequence of SEQ ID NO: 21, which encodes the amino acid sequence of SEQ ID NO: 6.

(2) Production of Fucose-Binding Protein 126 Using Recombinant E. coli

Production of the fucose-binding protein 126 using the recombinant E. coli BL21 (DE3)/pET-BC2LCN(126), and collection of the soluble protein extract, were carried out by the same method as in (2) of Comparative Example 1.

(3) Purification of Fucose-Binding Protein 126 and Evaluation of Productivity

Purification of the fucose-binding protein 126 from the soluble protein extract collected in (2) of Example 5 was carried out by the same method as in (3) of Comparative Example 1, to obtain "20% B eluted fraction", "50% B eluted fraction", and "100% B eluted fraction". Subsequently, the "50% B eluted fraction" and the "100% B eluted fraction" containing the fucose-binding protein 126 were combined to provide a purified 126 solution, and the productivity of the fucose-binding protein 126 per 1-L culture broth was calculated according to the method described in (4) of Comparative Example 1. As a result, the productivity was found to be 550 mg/L-culture broth.

Table 5 shows the productivities of the recombinant BC2LCN(155)cys, fucose-binding protein 129, fucose-binding protein 127, fucose-binding protein 129G36C, fucose-binding protein 127G36C, and fucose-binding protein 126, produced in Comparative Example 1 and Example 1 to Example 5, per 1-L culture broth. As is evident from Table 5, the productivities of the fucose-binding proteins produced in Example 1 to Example 5 are 2.5 times to 3.5 times higher than that productivity of the recombinant BC2LCN(155)cys, which was produced in Comparative Example 1.

[Table 5]

TABLE 5

| Example/ Comparative Example | Recombinant protein | Productivity (mg/L- culture broth) |
| --- | --- | --- |
| Comparative Example 1 | Recombinant BC2LCN(155)cys | 162 |
| Example 1 | Fucose-binding protein 129 | 475 |
| Example 2 | Fucose-binding protein 127 | 560 |
| Example 3 | Fucose-binding protein 129G36C | 428 |

TABLE 5-continued

| Example/ Comparative Example | Recombinant protein | Productivity (mg/L- culture broth) |
| --- | --- | --- |
| Example 4 | Fucose-binding protein 127G36C | 465 |
| Example 5 | Fucose-binding protein 126 | 550 |

Example 6 Analysis of Recombinant
BC2LCN(155)cys and Fucose-Binding Proteins by
SDS-PAGE Method Example 5 is related to analysis of the purified 129 solution containing the fucose-binding protein 129, the purified 127 solution containing the fucose-binding protein 127, the purified 129G36C solution containing the fucose-binding protein 129G36C, the purified 127G36C solution containing the fucose-binding protein 127G36C, and the purified BC2LCN(155) solution containing the recombinant BC2LCN(155)cys, obtained in Examples 1 to 4 and Comparative Example 1, by the SDS-PAGE method under non-reducing conditions and reducing conditions.

(1) Preparation of Samples for SDS-PAGE Analysis

Using the purified 129 solution, the purified 127 solution, the purified 129G36C solution, the purified 127G36C solution, and the purified BC2LCN(155) solution as sample solutions, samples for SDS-PAGE analysis were prepared by the methods described in the following (Ex. 5-1) to (Ex. 5-3).

(Ex. 5-1) The protein concentration of each sample solution was adjusted to 0.25 mg/mL using D-PBS(−), and 50 μL of the resulting solution was mixed with 50 μL of the 2×SDS sample buffer, followed by heating the resulting mixture at 94° C. for 5 minutes. To a lane for SDS-PAGE, 10 μL of the solution obtained (hereinafter referred to as non-reduced sample solution) was applied, and analysis by the SDS-PAGE method was carried out (amount of protein applied: 1.3 μg/lane).

(Ex. 5-2): The protein concentration of each sample solution was adjusted to 0.25 mg/mL using D-PBS(−), and 100 mM aqueous TCEP solution was added thereto to a final concentration of 0.48 μM, followed by allowing the reaction to proceed at room temperature for 2 hours. With 50 μL of the solution after the reaction, 50 μL of the 2×SDS sample buffer was mixed, and the resulting mixture was heated at 94° C. for 5 minutes. To a lane for SDS-PAGE, 10 μL of the solution obtained (hereinafter referred to as TCEP-reduced sample solution) was applied, and analysis by the SDS-PAGE method was carried out (amount of protein applied: 1.3 μg/lane).

(Ex. 5-3): Dithiothreitol (DTT, manufactured by FUJIFILM Wako Pure Chemical Corporation) was added to the 2×SDS sample buffer to a final concentration of 100 mM, and dissolved therein. The protein concentration of each sample solution was adjusted to 0.25 mg/mL using D-PBS(−), and 50 μL of the resulting solution was mixed with 50 μL of the 2×SDS sample buffer containing DTT dissolved therein, followed by heating the resulting mixture at 94° C. for 5 minutes. To a lane for SDS-PAGE, 10 μL of the solution obtained (hereinafter referred to as DTT-reduced sample solution) was applied, and analysis by the SDS-PAGE method was carried out (amount of protein applied: 1.3 μg/lane).

(2) Analysis by SDS-PAGE Method

The 15 kinds of samples for SDS-PAGE analysis prepared in (Ex. 5-1) to (Ex. 5-3) (the five kinds of non-reduced sample solutions, the five kinds of TCEP-reduced sample solutions, and the five kinds of DTT-reduced sample solutions) were analyzed by the SDS-PAGE method using a commercially available 15% gel (manufactured by ATTO). The results are shown in FIG. 2. In FIG. 2, "M" represents molecular weight markers; "Non-reduced" represents the non-reduced sample solutions; "TCEP-reduced" represents the TCEP-reduced sample solutions; and "DTT-reduced" represents the DTT-reduced sample solutions. "129" represents the fucose-binding protein 129 produced in Example 1; "127" represents the fucose-binding protein 127 produced in Example 2; "129G36C" represents the fucose-binding protein 129G36C produced in Example 3; "127G36C" represents the fucose-binding protein 127G36C produced in Example 4; and "155" represents the recombinant BC2LCN (155)cys produced in Comparative Example 1.

Regarding the non-reduced sample solutions in FIG. 2, each of the fucose-binding protein 127, the fucose-binding protein 127G36C, the fucose-binding protein 129, and the fucose-binding protein 129G36C showed bands near the molecular weight (about 14 kDa) of the monomer and near a molecular weight (about 28 kDa) presumably corresponding to the dimer. The recombinant BC2LCN(155)cys also showed bands near the molecular weight (about 17 kDa) of the monomer and near a molecular weight (about 34 kDa) presumably corresponding to the dimer.

On the other hand, regarding the TCEP-reduced sample solutions and the DTT-reduced sample solutions in FIG. 2, none of the five kinds of sample solutions showed the band near the molecular weight presumably corresponding to the dimer, but they showed a single band near the molecular weight of the monomer. Thus, it became clear that the band found near the molecular weight presumably corresponding to the dimer for each non-reduced sample solution is the dimer of each evaluation sample. When the results for the non-reduced sample solutions were compared between the fucose-binding protein 127cys and the fucose-binding protein 127G36C, and between the fucose-binding protein 129 and the fucose-binding protein 129G36C, each of the fucose-binding protein 127G36C and the fucose-binding protein 129G36C, wherein the glycine residue identified as the glycine residue at position 36 in SEQ ID NO: 1 is substituted with a cysteine residue, was found to show a weaker band near the molecular weight of the dimer relative to the fucose-binding protein 127 and the fucose-binding protein 129, which do not have this amino acid substitution. Thus, it became clear that the amino acid substitution suppressed generation of the dimers which is assumed to be due to formation of disulfide bonds.

Example 7 Production of Fucose-Binding Protein
129E81C and Evaluation of Binding Affinities to
Sugar Chains Example 7 is related to production of a fucose-binding protein (hereinafter referred to as fucose-binding protein 129E81C) by adding an oligopeptide containing a polyhistidine sequence to the N-terminus, and adding an oligopeptide containing a cysteine residue to the C-terminus, of the amino acid sequence of the fucose-binding protein of SEQ ID NO: 7 (amino acid sequence which is the same as SEQ ID NO: 2 except that the glutamic acid residue at position 81 is substituted with a cysteine residue), which is composed of 129 amino acid residues, and evaluation of the binding affinities thereof to sugar chains.

(1) Production of Fucose-Binding Protein 129E81C

A mutation was introduced to the fucose-binding protein 129 described in Example 1, such that the glutamic acid residue identified as the glutamic acid residue at position 81 in SEQ ID NO: 1 was substituted with a cysteine residue, to produce the fucose-binding protein 129E81C. The amino acid sequence of the fucose-binding protein 129E81C is SEQ ID NO: 38, wherein the sequence from position 15 to position 143 corresponds to the amino acid sequence of SEQ ID NO: 7 (amino acid sequence which is the same as SEQ ID NO: 1 except that the glutamic acid residue at position 81 is substituted with a cysteine residue), and the sequence from position 144 to position 150 corresponds to the oligo-peptide sequence containing a cysteine residue.

Using the expression vector pET-BC2LCN(129)cys in (1) of Example 1 as a template, and using oligonucleotides having the sequences of SEQ ID NO: 54 and SEQ ID NO: 55 as PCR primers, PCR was carried out by the method disclosed in JP 2018-000038 A. The resulting PCR product was digested with the restriction enzymes KpnI and XhoI, and then subjected to ligation reaction with the expression vector pET-BC2LCN(129)cys described in (1) of Example 1 that had been similarly treated with the restriction enzymes. *E. coli* BL21 (DE3) was transformed using the ligation product, to obtain the recombinant *E. coli* BL21 (DE3)/pET-BC2LCN(129E81C)cys. By the method disclosed in JP 2018-000038 A, the recombinant *E. coli* BL21 (DE3)/pET-BC2LCN(129E81C)cys obtained was cultured, and then the expression vector pET-BC2LCN(129E81C)cys was obtained by extraction from the bacterial cells. As a result of confirmation of the nucleotide sequence by sequence analy-sis, it was confirmed that the expression vector pET-BC2LCN(129E81C)cys contains the nucleotide sequence of SEQ ID NO: 22, which encodes the amino acid sequence of SEQ ID NO: 7.

Production of the fucose-binding protein 129E81C using the recombinant *E. coli* BL21 (DE3)/pET-BC2LCN (129E81C)cys, collection of the soluble protein extract, and purification of the fucose-binding protein 129E81C from the soluble protein extract by nickel chelate affinity chromatog-raphy were carried out by the methods described in (2) of Comparative Example 1 and (3) of Comparative Example 1, to produce the desired fucose-binding protein 129E81C. The solution containing the fucose-binding protein 129E81C produced was dialyzed against D-PBS(−), and then its concentration was adjusted to an appropriate concentration using D-PBS(−). The solution was then used in the later-described evaluation of the binding affinities to sugar chains.

(2) Evaluation of Binding Affinities of Fucose-Binding Protein 129E81C to Sugar Chains By the surface plasmon resonance method, the binding affinities of the fucose-binding protein 129E81C to H type 1 sugar chain and H type 3 sugar chain were evaluated. More specifically, a Biacore T100 (T200 Sensitivity Enhanced) apparatus (manufactured by GE Healthcare) was used to carry out kinetics analysis using the recombinant protein as an analyte, and H type 1 sugar chain or H type 3 sugar chain as a solid phase. As a sensor chip, a Sensor Chip CM5 (manufactured by GE Healthcare) coated with dextran was used. After immobilizing streptavidin (manufactured by FUJIFILM Wako Pure Chemical Corporation) to the dextran by the amine coupling method, biotin-labeled H type 1 sugar chain or H type 3 sugar chain (manufactured by Glycotech) was added thereto to allow immobilization of the sugar chain on the sensor chip by the biotin-streptavidin reaction, to prepare sensor chips on which H type 1 sugar chain or H type 3 sugar chain is immobilized. Measurement of the sugar-chain binding affinity was carried out using HBS-EP+ (manufactured by GE Healthcare) as a buffer, under the following measurement conditions: flow rate, 30 μL/minute; binding time, 6 minutes; dissociation time, 3 minutes or 6 minutes. Regeneration of the sensor chip was carried out using 25 mM sodium hydroxide at a flow rate of 30 μL/minute for a regeneration time of 30 seconds. The analysis was carried out using the analysis software (Biacore T100 Evaluation Software, version or Biacore T200 Evalu-ation Software, version) attached to the Biacore T100 (T200 Sensitivity Enhanced) apparatus, and the dissociation con-stant ($K_D$) was calculated by fitting of 1:1 binding.

As a result of the calculation of the dissociation constant of the fucose-binding protein 129E81C for each of H type 1 sugar chain and H type 3 sugar chain, the dissociation constant for H type 1 sugar chain was found to be 2.3 nM, and the dissociation constant for H type 3 sugar chain was found to be 3.1 nM.

Example 8 Production of Fucose-Binding Protein 129E81Q and Evaluation of Binding Affinities to Sugar Chains Example 8 is related to production of a fucose-binding protein (hereinafter referred to as fucose-binding protein 129E81Q) by adding an oligopeptide containing a polyhis-tidine sequence to the N-terminus, and adding an oligopep-tide containing a cysteine residue to the C-terminus, of the amino acid sequence of the fucose-binding protein of SEQ ID NO: 8 (amino acid sequence which is the same as SEQ ID NO: 2 except that the glutamic acid residue at position 81 is substituted with a glutamine residue), which is composed of 129 amino acid residues, and evaluation of the binding affinities thereof to sugar chains.

(1) Production of Fucose-Binding Protein 129E81Q

A mutation was introduced to the fucose-binding protein 129 described in Example 1, such that the glutamic acid residue identified as the glutamic acid residue at position 81 in SEQ ID NO: 1 was substituted with a glutamine residue, to produce the fucose-binding protein 129E81Q. The amino acid sequence of the fucose-binding protein 129E81Q is SEQ ID NO: 39, wherein the sequence from position 15 to position 143 corresponds to the amino acid sequence of SEQ ID NO: 8 (amino acid sequence which is the same as SEQ ID NO: 1 except that the glutamic acid residue at position 81 is substituted with a glutamine residue), and the sequence from position 144 to position 150 corresponds to the oligo-peptide sequence containing a cysteine residue.

Using the expression vector pET-BC2LCN(129)cys in (1) of Example 1 as a template, and using oligonucleotides having the sequences of SEQ ID NO: 54 and SEQ ID NO: 56 as PCR primers, PCR was carried out by the method disclosed in JP 2018-000038 A. The resulting PCR product was digested with the restriction enzymes KpnI and XhoI, and then subjected to ligation reaction with the expression vector pET-BC2LCN(129)cys described in (1) of Example 1 that had been similarly treated with the restriction enzymes. *E. coli* BL21 (DE3) was transformed using the ligation product, to obtain the recombinant *E. coli* BL21 (DE3)/pET-BC2LCN(129E81Q)cys. By the method disclosed in JP 2018-000038 A, the recombinant *E. coli* BL21 (DE3)/pET-BC2LCN(129E81Q)cys obtained was cultured, and then the expression vector pET-BC2LCN(129E81Q)cys was obtained by extraction from the bacterial cells. As a result of confirmation of the nucleotide sequence by sequence analy-sis, it was confirmed that the expression vector pET- BC2LCN(129E81Q)cys contains the nucleotide sequence of SEQ ID NO: 23, which encodes the amino acid sequence of SEQ ID NO: 8.

Production of the fucose-binding protein 129E81Q using the recombinant *E. coli* BL21 (DE3)/pET-BC2LCN (129E81Q)cys, collection of the soluble protein extract, and purification of the fucose-binding protein 129E81Q from the soluble protein extract by nickel chelate affinity chromatography were carried out by the methods described in (2) of Comparative Example 1 and (3) of Comparative Example 1, to produce the desired fucose-binding protein 129E81Q. The solution containing the fucose-binding protein 129E81Q produced was dialyzed against D-PBS(–), and then its concentration was adjusted to an appropriate concentration using D-PBS(–). The solution was then used in the later-described evaluation of the binding affinities to sugar chains.
(2) Evaluation of Binding Affinities of Fucose-Binding Protein 129E81Q to Sugar Chains As a result of evaluation of the binding affinities of the fucose-binding protein 129E81Q to H type 1 sugar chain and H type 3 sugar chain by the method described in (2) of Example 7, the dissociation constant for H type 1 sugar chain was found to be 3.7 nM, and the dissociation constant for H type 3 sugar chain was found to be 3.6 nM.

Example 9 Production of Fucose-Binding Protein 129E81H and Evaluation of Productivity and Binding Affinities to Sugar Chains Example 9 is related to production of a fucose-binding protein (hereinafter referred to as fucose-binding protein 129E81H) by adding an oligopeptide containing a polyhistidine sequence to the N-terminus, and adding an oligopeptide sequence containing a cysteine residue to the C-terminus, of the amino acid sequence of the fucose-binding protein of SEQ ID NO: 9 (amino acid sequence which is the same as SEQ ID NO: 2 except that the glutamic acid residue at position 81 is substituted with a histidine residue), which is composed of 129 amino acid residues, and evaluation of the productivity thereof and the binding affinities thereof to sugar chains.
(1) Production of Fucose-Binding Protein 129E81H and Evaluation of Productivity A mutation was introduced to the fucose-binding protein 129 described in Example 1, such that the glutamic acid residue identified as the glutamic acid residue at position 81 in SEQ ID NO: 1 was substituted with a histidine residue, to produce the fucose-binding protein 129E81H. The amino acid sequence of the fucose-binding protein 129E81H is SEQ ID NO: 40, wherein the sequence from position 15 to position 143 corresponds to the amino acid sequence of SEQ ID NO: 9 (amino acid sequence which is the same as SEQ ID NO: 1 except that the glutamic acid residue at position 81 is substituted with a histidine residue), and the sequence from position 144 to position 150 corresponds to the oligopeptide sequence containing a cysteine residue.

Using the expression vector pET-BC2LCN(129)cys in (1) of Example 1 as a template, and using oligonucleotides having the sequences of SEQ ID NO: 54 and SEQ ID NO: 57 as PCR primers, PCR was carried out by the method disclosed in JP 2018-000038 A. The resulting PCR product was digested with the restriction enzymes KpnI and XhoI, and then subjected to ligation reaction with the expression vector pET-BC2LCN(129)cys described in (1) of Example 1 that had been similarly treated with the restriction enzymes. *E. coli* BL21 (DE3) was transformed using the ligation product, to obtain the recombinant *E. coli* BL21 (DE3)/pET- BC2LCN(129E81H)cys. By the method disclosed in JP 2018-000038 A, the recombinant *E. coli* BL21 (DE3)/pET-BC2LCN(129E81H)cys obtained was cultured, and then the expression vector pET-BC2LCN(129E81H)cys was obtained by extraction from the bacterial cells. As a result of confirmation of the nucleotide sequence by sequence analysis, it was confirmed that the expression vector pET-BC2LCN(129E81H)cys contains the nucleotide sequence of SEQ ID NO: 24, which encodes the amino acid sequence of SEQ ID NO: 9.

Production of the fucose-binding protein 129E81H using the recombinant *E. coli* BL21 (DE3)/pET-BC2LCN (129E81H)cys, collection of the soluble protein extract, and purification of the fucose-binding protein 129E81H from the soluble protein extract by nickel chelate affinity chromatography were carried out by the methods described in (2) of Comparative Example 1 and (3) of Comparative Example 1, to produce the desired fucose-binding protein 129E81H. The productivity of the fucose-binding protein 129E81H per 1-L culture broth was calculated according to the method described in (4) of Comparative Example 1. As a result, the productivity was found to be 350 mg/L-culture broth. The solution containing the fucose-binding protein 129E81H produced was dialyzed against D-PBS(–), and then its concentration was adjusted to an appropriate concentration using D-PBS(–). The solution was then used in the later-described evaluation of the binding affinities to sugar chains.
(2) Evaluation of Binding Affinities of Fucose-Binding Protein 129E81H to Sugar Chains As a result of evaluation of the binding affinities of the fucose-binding protein 129E81H to H type 1 sugar chain and H type 3 sugar chain by the method described in (2) of Example 7, the dissociation constant for H type 1 sugar chain was found to be 1.0 nM, and the dissociation constant for H type 3 sugar chain was found to be 0.8 nM.

Example 10 Production of Fucose-Binding Protein 129E81M and Evaluation of Binding Affinities to Sugar Chains Example 10 is related to production of a fucose-binding protein (hereinafter referred to as fucose-binding protein 129E81M) by adding an oligopeptide containing a polyhistidine sequence to the N-terminus, and adding an oligopeptide containing a cysteine residue to the C-terminus, of the amino acid sequence of the fucose-binding protein of SEQ ID NO: 10 (amino acid sequence which is the same as SEQ ID NO: 2 except that the glutamic acid residue at position 81 is substituted with a methionine residue), which is composed of 129 amino acid residues, and evaluation of the binding affinities thereof to sugar chains.
(1) Production of Fucose-Binding Protein 129E81M A mutation was introduced to the fucose-binding protein 129 described in Example 1, such that the glutamic acid residue identified as the glutamic acid residue at position 81 in SEQ ID NO: 1 was substituted with a methionine residue, to produce the fucose-binding protein 129E81M. The amino acid sequence of the fucose-binding protein 129E81M is SEQ ID NO: 41, wherein the sequence from position 15 to position 143 corresponds to the amino acid sequence of SEQ ID NO: 10 (amino acid sequence which is the same as SEQ ID NO: 1 except that the glutamic acid residue at position 81 is substituted with a methionine residue), and the sequence from position 144 to position 150 corresponds to the oligopeptide sequence containing a cysteine residue.

Using the expression vector pET-BC2LCN(129)cys in (1) of Example 1 as a template, and using oligonucleotides having the sequences of SEQ ID NO: 54 and SEQ ID NO: 58 as PCR primers, PCR was carried out by the method disclosed in JP 2018-000038 A. The resulting PCR product was digested with the restriction enzymes KpnI and XhoI, and then subjected to ligation reaction with the expression vector pET-BC2LCN(129)cys described in (1) of Example 1 that had been similarly treated with the restriction enzymes. *E. coli* BL21 (DE3) was transformed using the ligation product, to obtain the recombinant *E. coli* BL21 (DE3)/pET-BC2LCN(129E81M)cys. By the method disclosed in JP 2018-000038 A, the recombinant *E. coli* BL21 (DE3)/pET-BC2LCN(129E81M)cys obtained was cultured, and then the expression vector pET-BC2LCN(129E81M)cys was obtained by extraction from the bacterial cells. As a result of confirmation of the nucleotide sequence by sequence analysis, it was confirmed that the expression vector pET-BC2LCN(129E81M)cys contains the nucleotide sequence of SEQ ID NO: 25, which encodes the amino acid sequence of SEQ ID NO: 10.

Production of the fucose-binding protein 129E81M using the recombinant *E. coli* BL21 (DE3)/pET-BC2LCN (129E81M)cys, collection of the soluble protein extract, and purification of the fucose-binding protein 129E81M from the soluble protein extract by nickel chelate affinity chromatography were carried out by the methods described in (2) of Comparative Example 1 and (3) of Comparative Example 1, to produce the desired fucose-binding protein 129E81M. The solution containing the fucose-binding protein 129E81M produced was dialyzed against D-PBS(−), and then its concentration was adjusted to an appropriate concentration using D-PBS(−). The solution was then used in the later-described evaluation of the binding affinities to sugar chains.

(2) Evaluation of Binding Affinities of Fucose-Binding Protein 129E81M to Sugar Chains As a result of evaluation of the binding affinities of the fucose-binding protein 129E81M to H type 1 sugar chain and H type 3 sugar chain by the method described in (2) of Example 7, the dissociation constant for H type 1 sugar chain was found to be 3.1 nM, and the dissociation constant for H type 3 sugar chain was found to be 3.1 nM.

Example 11 Evaluation of Binding Affinities of Fucose-Binding Protein 129 to Sugar Chains Example 11 is related to evaluation of the binding affinities of the fucose-binding protein 129 produced in Example 1 to sugar chains. As a result of evaluation of the binding affinities of the fucose-binding protein 129 to H type 1 sugar chain and H type 3 sugar chain by the method described in (2) of Example 7, the dissociation constant for H type 1 sugar chain was found to be 2.7 nM, and the dissociation constant for H type 3 sugar chain was found to be 11 nM.

Comparative Example 2 Evaluation of Binding Affinities of Recombinant BC2LCN(155)cys to Sugar Chains Comparative Example 2 is related to evaluation of the binding affinities of the recombinant BC2LCN(155)cys produced in Comparative Example 1 to sugar chains. As a result of evaluation of the binding affinities of the recombinant BC2LCN(155)cys produced in Comparative Example 1 to H type 1 sugar chain and H type 3 sugar chain by the method described in (2) of Example 7, the dissociation constant for H type 1 sugar chain was found to be 3.9 nM, and the dissociation constant for H type 3 sugar chain was found to be 11 nM.

The dissociation constants of the fucose-binding proteins evaluated in Examples 6 to 10 and the recombinant BC2LCN(155)cys evaluated in Comparative Example 2, for H type 1 sugar chain and H type 3 sugar chain are shown in Table 6. The lower the dissociation constant, the higher the binding affinity. It can be seen, as shown in Table 6, that the fucose-binding protein 129E81C evaluated in Example 7 (wherein the glutamic acid residue identified as the glutamic acid residue at position 81 in SEQ ID NO: 1 is substituted with a cysteine residue), the fucose-binding protein 129E81Q evaluated in Example 8 (wherein the glutamic acid residue identified as the glutamic acid residue at position 81 in SEQ ID NO: 1 is substituted with a glutamine residue), the fucose-binding protein 129E81H evaluated in Example 9 (wherein the glutamic acid residue identified as the glutamic acid residue at position 81 in SEQ ID NO: 1 is substituted with a histidine residue), and the fucose-binding protein 129E81M evaluated in Example 10 (wherein the glutamic acid residue identified as the glutamic acid residue at position 81 in SEQ ID NO: 1 is substituted with a methionine residue) have higher binding affinities to H type 1 sugar chain and H type 3 sugar chain than the recombinant BC2LCN(155)cys evaluated in Comparative Example 2 (wherein the glutamic acid residue identified as the glutamic acid residue at position 81 in SEQ ID NO: 1 is not substituted). Further, it can be seen that the fucose-binding protein 129 evaluated in Example 11 (wherein the glutamic acid residue identified as the glutamic acid residue at position 81 in SEQ ID NO: 1 is not substituted) has a higher binding affinity to H type 1 sugar chain than the recombinant BC2LCN(155)cys evaluated in Comparative Example 2.

[Table 6]

TABLE 6

| Example/ Comparative Example | Recombinant protein | Dissociation constant (nM) | |
|---|---|---|---|
| | | H type 1 sugar chain | H type 3 sugar chain |
| Example 7 | Fucose-binding protein 129E81C | 2.3 | 3.1 |
| Example 8 | Fucose-binding protein 129E81Q | 3.7 | 3.6 |
| Example 9 | Fucose-binding protein 129E81H | 1.0 | 0.8 |
| Example 10 | Fucose-binding protein 129E81M | 3.1 | 3.1 |
| Example 11 | Fucose-binding protein 129 | 2.7 | 11 |
| Comparative Example 2 | Recombinant BC2LCN(155)cys | 3.9 | 11 |

Reference Example 1 Production and Functional Evaluation of Amino Acid Substitution Products of Recombinant BC2LCN-1

In Reference Example 1, mutations were introduced to the recombinant BC2LCN described in Comparative Example 1 at the glutamic acid residue identified as the glutamic acid residue at position 81 in SEQ ID NO: 1, that is, mutations were introduced such that the glutamic acid residue at position 95 in the amino acid sequence of the recombinant BC2LCN(155)cys (SEQ ID NO: 32) is substituted with other amino acid residues. The recombinant proteins were produced using transformants, and evaluated for their thermal stabilities and for their binding affinities to H type 1 sugar chain and H type 3 sugar chain.

(1) Introduction of Mutations to Cysteine Residue Identified as Cysteine Residue at Position 72 in SEQ ID NO: 1

Using the expression vector pET-BC2LCN(155)cys described in (1) of Comparative Example 1 as a template, and using oligonucleotides having the sequences of SEQ ID NO: 54 and SEQ ID NO: 61 as PCR primers, PCR was carried out by the method disclosed in JP 2018-000038 A. The PCR primer having the sequence of SEQ ID NO: 61 was designed to have the degenerate sequence NNB (N=A, C, G, or T; B=C, G, or T) such that the glutamic acid residue at position 95 in SEQ ID NO: 32 (which corresponds to the glutamic acid residue at position 81 in SEQ ID NO: 1) is randomly substituted with another amino acid residue. The resulting PCR product was digested with the restriction enzymes KpnI and XhoI, and then subjected to ligation reaction with the expression vector pET-BC2LCNcys described in (1) that had been similarly treated with the restriction enzymes. *E. coli* BL21 (DE3) was transformed using the ligation product, to obtain a plurality of transformants. An expression vector was extracted from each transformant, and its nucleotide sequence was analyzed. As a result, the 19 kinds of expression vectors shown in Table 7 and transformants having these expression vectors were prepared.

[Table 7]

TABLE 7

| Expression vector | Trans-formant | Recombinant protein | Amino acid substitution* |
|---|---|---|---|
| pET-L1a | L1a | Fucose-binding protein E81C | Cysteine residue |
| pET-L2a | L2a | Fucose-binding protein E81Q | Glutamine residue |
| pET-L3a | L3a | Fucose-binding protein E81H | Histidine residue |
| pET-L4a | LAa | Fucose-binding protein E81M | Methionine residue |
| pET-L5a | L5a | Fucose-binding protein E81V | Valine residue |
| pET-L6a | L6a | Fucose-binding protein E81K | Lysine residue |
| pET-L7a | L7a | Fucose-binding protein E81S | Serine residue |
| pET-L8a | L8a | Fucose-binding protein E81I | Isoleucine residue |
| pET-L9a | L9a | Fucose-binding protein E81Y | Tyrosine residue |
| pET-L10a | L10a | Fucose-binding protein E81G | Glycine residue |
| pET-L11a | L11a | Fucose-binding protein E81P | Proline residue |
| pET-L12a | L12a | Fucose-binding protein E81L | Leucine residue |
| pET-L13a | L13a | Fucose-binding protein E81N | Asparagine residue |
| pET-L14a | L14a | Fucose-binding protein E81F | Phenylalanine residue |
| pET-L15a | L15a | Fucose-binding protein E81D | Aspartic acid residue |
| pET-L16a | L16a | Fucose-binding protein E81A | Alanine residue |
| pET-L17a | L17a | Fucose-binding protein E81W | Tryptophan residue |
| pET-L18a | L18a | Fucose-binding protein E81T | Threonine residue |
| pET-L19a | L19a | Fucose-binding protein E81R | Arginine residue |

*Amino acid substitution of the glutamic acid residue at position 95 in the amino acid sequence of recombinant BC2LCNcys (SEQ ID NO: 32)

(2) Production of Recombinant Proteins

Using the transformants L1a to L19a (Table 7) prepared in (1), production of recombinant proteins, collection of soluble protein extracts, and purification of fucose-binding proteins from the soluble protein extracts by nickel chelate affinity chromatography were carried out by the method described in Comparative Example 1, to produce the 19 kinds of recombinant proteins described in Table 7. The solutions containing the 19 kinds of fucose-binding proteins were dialyzed against D-PBS(−), and then their concentrations were appropriately adjusted using D-PBS(−). The solutions were then used in the later-described evaluation of the binding affinities to sugar chains.

(3) Evaluation of Sugar-Chain Binding Affinities of Recombinant Proteins

In order to investigate the binding affinities of the recombinant proteins produced in (2) to sugar chains, the binding affinities of the recombinant proteins to H type 1 sugar chain and H type 3 sugar chain were evaluated by the method described in (2) of Example 7. Table 8 shows the dissociation constants of the recombinant proteins produced in (3) and the recombinant BC2LCN(155)cys, for H type 1 sugar chain and H type 3 sugar chain. It can be seen, as shown in Table 8, that the fucose-binding protein E81C (A1: the glutamic acid residue identified as the glutamic acid residue at position 81 in SEQ ID NO: 1 is substituted with a cysteine residue), the fucose-binding protein E81Q (A2: the glutamic acid residue identified as the glutamic acid residue at position 81 in SEQ ID NO: 1 is substituted with a glutamine residue), the fucose-binding protein E81H (A3: the glutamic acid residue identified as the glutamic acid residue at position 81 in SEQ ID NO: 1 is substituted with a histidine residue), and the fucose-binding protein E81M (A4: the glutamic acid residue identified as the glutamic acid residue at position 81 in SEQ ID NO: 1 is substituted with methionine) have higher binding affinities to H type 1 sugar chain and H type 3 sugar chain than the recombinant BC2LCN(155)cys (C0: the glutamic acid residue identified as the glutamic acid residue at position 81 in SEQ ID NO: 1 is not substituted).

It can also be seen that the fucose-binding protein E81V (B1: the glutamic acid residue identified as the glutamic acid residue at position 81 in SEQ ID NO: 1 is substituted with a valine residue), the fucose-binding protein E81K (B2: the glutamic acid residue identified as the glutamic acid residue at position 81 in SEQ ID NO: 1 is substituted with a lysine residue), the fucose-binding protein E81S (B3: the glutamic acid residue identified as the glutamic acid residue at position 81 in SEQ ID NO: 1 is substituted with a serine residue), the fucose-binding protein E81I (B4: the glutamic acid residue identified as the glutamic acid residue at position 81 in SEQ ID NO: 1 is substituted with a isoleucine residue), the fucose-binding protein E81Y (B5: the glutamic acid residue identified as the glutamic acid residue at position 81 in SEQ ID NO: 1 is substituted with a tyrosine residue), the fucose-binding protein E81G (B6: the glutamic acid residue identified as the glutamic acid residue at position 81 in SEQ ID NO: 1 is substituted with a glycine residue), the fucose-binding protein E81P (B7: the glutamic acid residue identified as the glutamic acid residue at position 81 in SEQ ID NO: 1 is substituted with a proline residue), the fucose-binding protein E81L (B8: the glutamic acid residue identified as the glutamic acid residue at position 81 in SEQ ID NO: 1 is substituted with a leucine residue), and the fucose-binding protein E81N (B9: the glutamic acid residue identified as the glutamic acid residue at position 81 in SEQ ID NO: 1 is substituted with asparagine) have higher binding affinities to H type 3 sugar chain than the recombinant BC2LCN(155)cys.

On the other hand, it can be seen that the fucose-binding protein E81F (C1), the fucose-binding protein E81D (C2), the fucose-binding protein E81A (C3), the fucose-binding protein E81W (C4), the fucose-binding protein E81T (C5), and the fucose-binding protein E81R (C6) have lower binding affinities to H type 1 sugar chain and H type 3 sugar chain than the recombinant BC2LCN(155)cys.

[Table 8]

TABLE 8

| | | Dissociation constant (nM) | |
|---|---|---|---|
| No. | Recombinant protein | H type 1 sugar chain | H type 3 sugar chain |
| C0 | Recombinant BC2LCN(155)cys | 3.9 | 11 |
| A1 | Fucose-binding protein E81C | 0.024 | 9.7 |
| A2 | Fucose-binding protein E81Q | 3.0 | 4.0 |
| A3 | Fucose-binding protein E81H | 3.0 | 7.8 |
| A4 | Fucose-binding protein E81M | 3.1 | 3.9 |
| B1 | Fucose-binding protein E81V | 8.3 | 4.4 |
| B2 | Fucose-binding protein E81K | 4.2 | 5.8 |
| B3 | Fucose-binding protein E81S | 5.0 | 6.1 |
| B4 | Fucose-binding protein E81I | 5.1 | 6.1 |
| B5 | Fucose-binding protein E81Y | 6.1 | 6.1 |
| B6 | Fucose-binding protein E81G | 12 | 9.4 |
| B7 | Fucose-binding protein E81P | 13 | 9.3 |
| B8 | Fucose-binding protein E81L | 7.0 | 9.4 |
| B9 | Fucose-binding protein E81N | 9.7 | 9.7 |
| C1 | Fucose-binding protein E81F | 7.1 | 11 |
| C2 | Fucose-binding protein E81D | 8.9 | 11 |
| C3 | Fucose-binding protein E81A | 12 | 12 |
| C4 | Fucose-binding protein E81W | 18 | 28 |
| C5 | Fucose-binding protein E81T | 14 | 31 |
| C6 | Fucose-binding protein E81R | 29 | 31 |

Example 12 Production and Functional Evaluation of Fucose-Binding Protein 127C72G Example 12 is related to production of a fucose-binding protein (hereinafter referred to as fucose-binding protein 127C72G) by adding an oligopeptide containing a polyhistidine sequence to the N-terminus, and adding an oligopeptide containing a cysteine residue to the C-terminus, of the amino acid sequence of the fucose-binding protein of SEQ ID NO: 11 (amino acid sequence which is the same as SEQ ID NO: 3 except that the cysteine residue at position 72 is substituted with a glycine residue), which is composed of 127 amino acid residues, and evaluation of the thermal stability thereof and the binding affinities thereof to sugar chains.

(1) Production of Fucose-Binding Protein 127C72G

The expression vector pET-BC2LCN(127C72G)cys is an expression vector for expression of the fucose-binding protein 127C72G. The amino acid sequence of the fucose-binding protein 127C72G is SEQ ID NO: 42, wherein the sequence from position 5 to position 10 corresponds to the polyhistidine sequence; the sequence from position 15 to position 141 corresponds to the amino acid sequence of SEQ ID NO: 11; and the sequence from position 142 to position 148 corresponds to the oligopeptide sequence containing a cysteine residue.

Using the expression vector pET-BC2LCN(127)cys in (1) of Example 2 as a template, and using oligonucleotides having the sequences of SEQ ID NO: 48 and SEQ ID NO: 59 as PCR primers, PCR was carried out by the method disclosed in JP 2018-000038 A. The resulting PCR product was digested with the restriction enzymes NcoI and KpnI, and then subjected to ligation reaction with the expression vector pET-BC2LCN(127)cys described in (1) of Example 2 that had been similarly treated with the restriction enzymes. *E. coli* BL21 (DE3) was transformed using the ligation product, to obtain the recombinant *E. coli* BL21 (DE3)/pET-BC2LCN(127C72G)cys. By the method disclosed in JP 2018-000038 A, the recombinant *E. coli* BL21 (DE3)/pET-BC2LCN(127C72G)cys obtained was cultured, and then the expression vector pET-BC2LCN(127C72G)cys was obtained by extraction from the bacterial cells. As a result of confirmation of the nucleotide sequence by sequence analysis, it was confirmed that the expression vector pET-BC2LCN(127C72G)cys contains the nucleotide sequence of SEQ ID NO: 26, which encodes the amino acid sequence of SEQ ID NO: 11.

Production of the fucose-binding protein 127C72G using the recombinant *E. coli* BL21 (DE3)/pET-BC2LCN (127C72G)cys, collection of the soluble protein extract, and purification of the fucose-binding protein 127C72G from the soluble protein extract by nickel chelate affinity chromatography were carried out by the methods described in (2) of Comparative Example 1 and (3) of Comparative Example 1, to produce the desired fucose-binding protein 127C72G. The productivity of the fucose-binding protein 127C72G per 1-L culture broth was calculated according to the method described in (4) of Comparative Example 1. As a result, the productivity was found to be 492 mg/L-culture broth. The solution containing the fucose-binding protein 127C72G produced was dialyzed against D-PBS(−), and then its concentration was adjusted to an appropriate concentration using D-PBS(−). The solution was then used in the later-described measurement of the denaturation midpoint temperature, evaluation of the sugar-chain binding affinities, and production of an adsorbent.

(2) Measurement of Denaturation Midpoint Temperature

The denaturation midpoint temperature of the fucose-binding protein 127C72G was measured. More specifically, the solution of the fucose-binding protein 127C72G in D-PBS(−) was subjected to buffer exchange using a regenerated cellulose membrane (manufactured by Thermo Fisher Scientific Inc.; molecular weight cutoff, 3500) in a dialysis buffer (50 mM sodium acetate, 150 mM sodium chloride; pH 5.5). The concentration of the recombinant protein in the inner dialysate was measured by the ultraviolet absorption method, and the recombinant protein was diluted to 500 μg/mL using the dialysis buffer, followed by measurement of the denaturation midpoint temperature using a differential scanning calorimeter (MicroCal VP-Capillary DSC, manufactured by Malvern Panalytical Ltd.). The denaturation midpoint temperature may be the temperature at which denaturation of half of the protein occurs. The higher the denaturation midpoint temperature, the higher the thermal stability. The following conditions were used for the measurement of the denaturation midpoint temperature: the amount of the solution of the fucose-binding protein 127C72G after the dialysis, 400 μL; heating rate, 60° C./h; heating temperature, 40° C. to 110° C. As a result of the measurement, the denaturation midpoint temperature of the fucose-binding protein 127C72G was found to be 88.3±0.5° C.

(3) Evaluation of Binding Affinities to Sugar Chains

As a result of evaluation of the binding affinities of the fucose-binding protein 127C72G to H type 1 sugar chain and H type 3 sugar chain by the method described in (2) of Example 7, the dissociation constant for H type 1 sugar chain was found to be 1.2 nM, and the dissociation constant for H type 3 sugar chain was found to be 1.1 nM.

Example 13 Production and Functional Evaluation of Fucose-Binding Protein 127C72A Example 13 is related to production of a fucose-binding protein (hereinafter referred to as fucose-binding protein 127C72A) by adding an oligopeptide containing a polyhistidine sequence to the N-terminus, and adding an oligopeptide containing a cysteine residue to the C-terminus, of the amino acid sequence of the fucose-binding protein of SEQ ID NO: 12 (amino acid sequence which is the same as SEQ ID NO: 3 except that the cysteine residue at position 72 is substituted with an alanine residue), which is composed of 127 amino acid residues, and evaluation of the thermal stability thereof and the binding affinities thereof to sugar chains.

(1) Production of Fucose-Binding Protein 127C72A

The expression vector pET-BC2LCN(127C72A)cys is an expression vector for expression of the fucose-binding protein 127C72A. The amino acid sequence of the fucose-binding protein 127C72A is SEQ ID NO: 43, wherein the sequence from position 5 to position 10 corresponds to the polyhistidine sequence; the sequence from position 15 to position 141 corresponds to the amino acid sequence of SEQ ID NO: 12; and the sequence from position 142 to position 148 corresponds to the oligopeptide sequence containing a cysteine residue.

Using the expression vector pET-BC2LCN(127)cys in (1) of Example 2 as a template, and using oligonucleotides having the sequences of SEQ ID NO: 48 and SEQ ID NO: 60 as PCR primers, PCR was carried out by the method disclosed in JP 2018-000038 A. The resulting PCR product was digested with the restriction enzymes NcoI and KpnI, and then subjected to ligation reaction with the expression vector pET-BC2LCN(127)cys described in (1) of Example 2 that had been similarly treated with the restriction enzymes. *E. coli* BL21 (DE3) was transformed using the ligation product, to obtain the recombinant *E. coli* BL21 (DE3)/pET-BC2LCN(127C72A)cys. By the method disclosed in JP 2018-000038 A, the recombinant *E. coli* BL21 (DE3)/pET-BC2LCN(127C72A)cys obtained was cultured, and then the expression vector pET-BC2LCN(127C72A)cys was obtained by extraction from the bacterial cells. As a result of confirmation of the nucleotide sequence by sequence analysis, it was confirmed that the expression vector pET-BC2LCN(127C72A)cys contains the nucleotide sequence of SEQ ID NO: 27, which encodes the amino acid sequence of SEQ ID NO: 12.

Production of the fucose-binding protein 127C72A using the recombinant *E. coli* BL21 (DE3)/pET-BC2LCN (127C72A)cys, collection of the soluble protein extract, and purification of the fucose-binding protein 127C72A from the soluble protein extract by nickel chelate affinity chromatography were carried out by the methods described in (2) of Comparative Example 1 and (3) of Comparative Example 1, to produce the desired fucose-binding protein 127C72A. The solution containing the fucose-binding protein 127C72A produced was dialyzed against D-PBS(−), and then its concentration was adjusted to an appropriate concentration using D-PBS(−). The solution was then used in the later-described measurement of the denaturation midpoint temperature and evaluation of the binding affinities to sugar chains.

(2) Measurement of Denaturation Midpoint Temperature

As a result of measurement of the denaturation midpoint temperature of the fucose-binding protein 127C72A by the method described in (2) of Example 12, the denaturation midpoint temperature of the fucose-binding protein 127C72A was found to be 83.4±0.5° C.

(3) Evaluation of Binding Affinities to Sugar Chains

As a result of evaluation of the binding affinities of the fucose-binding protein 127C72G to H type 1 sugar chain and H type 3 sugar chain by the method described in (2) of Example 7, the dissociation constant for H type 1 sugar chain was found to be 0.7 nM, and the dissociation constant for H type 3 sugar chain was found to be 2.0 nM.

Comparative Example 3 Evaluation of Thermal Stability of Recombinant BC2LCN(155)cys Comparative Example 3 is related to evaluation of the thermal stability of the recombinant BC2LCN(155)cys produced in Comparative Example 1. As a result of measurement of the denaturation midpoint temperature of the recombinant BC2LCN(155)cys produced in Comparative Example 1, by the method described in (2) of Example 12, the denaturation midpoint temperature of the recombinant BC2LCN(155)cys was found to be 82.3±0.5° C.

Table 9 shows the denaturation midpoint temperatures, and the dissociation constants for H type 1 sugar chain and H type 3 sugar chain, of the fucose-binding protein 127C72G (Example 12), the fucose-binding protein127C72A (Example 13), and the recombinant BC2LCN(155)cys (Comparative Example 3), measured in Examples 12 and 13, and Comparative Example 3. As shown in Table 9, it can be seen that the fucose-binding protein 127C72G (wherein the cysteine residue identified as the cysteine residue at position 72 in SEQ ID NO: 1 is substituted with a glycine residue) and the fucose-binding protein C72A (wherein the cysteine residue identified as the cysteine residue at position 72 in SEQ ID NO: 1 is substituted with an alanine residue) have higher denaturation midpoint temperatures, that is, improved thermal stabilities, compared to the recombinant BC2LCNcys (wherein the cysteine residue identified as the cysteine residue at position 72 in SEQ ID NO: 1 is not substituted). Similarly, it can be seen that the fucose-binding protein 127C72G and the fucose-binding protein C72A have higher binding affinities to H type 1 sugar chain and H type 3 sugar chain than the recombinant BC2LCNcys.

[Table 9]

TABLE 9

| Example/ Comparative Example | Recombinant protein | Denaturation midpoint temperature (° C.) | Dissociation constant (nM) | |
|---|---|---|---|---|
| | | | H type 1 sugar chain | H type 3 sugar chain |
| Example 12 | Fucose-binding protein 127C72G | 88.3 ± 0.5 | 1.2 | 1.1 |
| Example 13 | Fucose-binding protein 127C72A | 83.4 ± 0.5 | 0.7 | 2.0 |
| Comparative Examples 2 and 3 | Recombinant BC2LCN(155)cys | 82.3 ± 0.5 | 3.9 | 11 |

Reference Example 2 Production and Functional Evaluation of Amino Acid Substitution Products of Recombinant BC2LCN-2

In Reference Example 2, mutations were introduced to the recombinant BC2LCN described in Comparative Example 1 at the cysteine residue identified as the cysteine residue at position 72 in SEQ ID NO: 1, that is, mutations were introduced such that the cysteine residue at position 86 in the amino acid sequence of the recombinant BC2LCN(155)cys (SEQ ID NO: 32) is substituted with other amino acid residues. The recombinant proteins were produced using transformants, and evaluated for their thermal stabilities and for their binding affinities to H type 1 sugar chain and H type 3 sugar chain.

(1) Introduction of Mutations to Cysteine Residue Identified as Cysteine Residue at Position 72 in SEQ ID NO: 1

Using the expression vector pET-BC2LCN(155)cys described in (1) of Comparative Example 1 as a template, and using oligonucleotides having the sequences of SEQ ID NO: 48 and SEQ ID NO: 62 as PCR primers, PCR was carried out by the method disclosed in JP 2018-000038 A. The PCR primer having the sequence of SEQ ID NO: 50 was designed to have the degenerate sequence VNN (V=A, C, or G; N=A, C, G) such that the cysteine residue at position 86 in SEQ ID NO: 32 (which corresponds to the cysteine residue at position 72 in SEQ ID NO: 1) is randomly substituted with another amino acid residue. The resulting PCR product was digested with the restriction enzymes NcoI and KpnI, and then subjected to ligation reaction with the expression vector pET-BC2LCNcys described in (1) that had been similarly treated with the restriction enzymes. *E. coli* BL21 (DE3) was transformed using the ligation product, to obtain a plurality of transformants. An expression vector was extracted from each transformant, and its nucleotide sequence was analyzed. As a result, the 19 kinds of expression vectors shown in Table 10 and transformants having these expression vectors were prepared.

[Table 10]

TABLE 10

| Expression vector | Transformant | Recombinant protein | Amino acid substitution* |
|---|---|---|---|
| pET-L1b | L1b | Fucose-binding protein C72G | Glycine residue |
| pET-L2b | L2b | Fucose-binding protein C72A | Alanine residue |
| pET-L3b | L3b | Fucose-binding protein C72W | Tryptophan residue |
| pET-L4b | LAb | Fucose-binding protein C72K | Lysine residue |
| pET-L5b | L5b | Fucose-binding protein C72H | Histidine residue |
| pET-L6b | L6b | Fucose-binding protein C72S | Serine residue |
| pET-L7b | L7b | Fucose-binding protein C72T | Threonine residue |
| pET-L8b | L8b | Fucose-binding protein C72N | Asparagine residue |
| pET-L9b | L9b | Fucose-binding protein C72Q | Glutamine residue |
| pET-L10b | L10b | Fucose-binding protein C72Y | Tyrosine residue |
| pET-L11b | L11b | Fucose-binding protein C72P | Proline residue |
| pET-L12b | L12b | Fucose-binding protein C72M | Methionine residue |
| pET-L13b | L13b | Fucose-binding protein C72F | Phenylalanine residue |
| pET-L14b | L14b | Fucose-binding protein C72R | Arginine residue |
| pET-L15b | L15b | Fucose-binding protein C72E | Glutamic acid residue |
| pET-L16b | L16b | Fucose-binding protein C72D | Aspartic acid residue |
| pET-L17b | L17b | Fucose-binding protein C72V | Valine residue |
| pET-L18b | L18b | Fucose-binding protein C72L | Leucine residue |
| pET-L19b | L19b | Fucose-binding protein C72I | Isoleucine residue |

*Amino acid substitution of the cysteine residue at position 86 in the amino acid sequence of recombinant BC2LCNcys (SEQ ID NO: 36)

(2) Production of Recombinant Proteins

Using the transformants L1b to L19b (Table 10) prepared in (1), production of recombinant proteins, collection of soluble protein extracts, and purification of fucose-binding proteins from the soluble protein extracts by nickel chelate affinity chromatography were carried out by the method described in Comparative Example 1, to produce the 19 kinds of recombinant proteins described in Table 10.

(3) Evaluation of Thermal Stabilities of Recombinant Proteins

In order to investigate the thermal stabilities of the recombinant proteins produced in (2), the sugar-chain binding affinity of each recombinant protein after heat treatment was evaluated by the surface plasmon resonance method. More specifically, the concentration of each recombinant protein produced in (2) was measured by the ultraviolet absorption method, and the recombinant protein was diluted to 30 µg/mL using D-PBS(-) (FUJIFILM Wako Pure Chemical Corporation). The recombinant protein solution prepared was left to stand at room temperature or 73° C. for 30 minutes, and a Biacore T100 (T200 Sensitivity Enhanced) apparatus (manufactured by GE Healthcare) was used to evaluate the sugar-chain binding capacity using the recombinant protein as an analyte, and H type 3 sugar chain as a solid phase. As a sensor chip, a Sensor Chip CM5 (manufactured by GE Healthcare) coated with dextran was used. After immobilizing streptavidin (manufactured by FUJIFILM Wako Pure Chemical Corporation) to the dextran by the amine coupling method, biotin-labeled H type 3 sugar chain (manufactured by Glycotech) was added thereto to allow immobilization of the sugar chain on the sensor chip by the biotin-streptavidin reaction, to prepare a sensor chip on which H type 3 sugar chain is immobilized. The binding capacity to H type 3 sugar chain was measured by the binding assay method, and the binding stability value was used as the measured value of the sugar-chain binding capacity. Using HBS-EP+ (manufactured by GE Healthcare) as a buffer, the measurement was carried out at a temperature of 25° C. The following binding conditions were used: flow rate, 30 µL/minute; binding time, 2 minutes; dissociation time, 1 minute. The following regeneration conditions were used for the sensor chip: use of 25 mM sodium hydroxide; flow rate, 30 µL/minute; regeneration time, 15 seconds. The analysis was carried out using the analysis software (Biacore T100 Evaluation Software, version or Biacore T200 Evaluation Software, version) attached to the Biacore T100 (T200 Sensitivity Enhanced) apparatus.

Table 11 shows the result of evaluation of the sugar-chain binding capacity of each recombinant protein after the heat treatment at 73° C. for 30 minutes. In Table 11, the sugar-chain binding capacity of each recombinant protein is expressed as a relative value with respect to the sugar-chain binding capacity after treatment at room temperature, which is taken as 100%. In Table 11, the sugar-chain binding capacities of the fucose-binding protein C72R, the fucose-binding protein C72E, the fucose-binding protein C72D, the fucose-binding protein C72V, the fucose-binding protein C72L, and the fucose-binding protein C72I are expressed as "-" since their sugar-chain binding capacities were lost after the treatment at room temperature. As shown in Table 11, the following recombinant proteins retained sugar-chain binding capacity even after the heat treatment at 73° C. for 30 minutes: the recombinant BC2LCNcys, which is the protein before the amino acid residue substitution, the fucose-binding protein C72G, the fucose-binding protein C72A, and the fucose-binding protein C72W.

[Table 11]

TABLE 11

| Recombinant protein | Amino acid substitution*[1] | Sugar-chain binding capacity (%)*[2] |
|---|---|---|
| Recombinant BC2LCNcys | None | 26.4 |
| Fucose-binding protein C72G | Glycine residue | 94.8 |
| Fucose-binding protein C72A | Alanine residue | 33.9 |
| Fucose-binding protein C72W | Tryptophan residue | 66.7 |
| Fucose-binding protein C72K | Lysine residue | 0.0 |
| Fucose-binding protein C72H | Histidine residue | 0.0 |
| Fucose-binding protein C72S | Serine residue | 0.0 |
| Fucose-binding protein C72T | Threonine residue | 0.0 |
| Fucose-binding protein C72N | Asparagine residue | 0.0 |
| Fucose-binding protein C72Q | Glutamine residue | 0.0 |

63

TABLE 11-continued

| Recombinant protein | Amino acid substitution*1 | Sugar-chain binding capacity (%)*2 |
|---|---|---|
| Fucose-binding protein C72Y | Tyrosine residue | 0.0 |
| Fucose-binding protein C72P | Proline residue | 0.0 |
| Fucose-binding protein C72M | Methionine residue | 0.0 |
| Fucose-binding protein C72F | Phenylalanine residue | 0.0 |
| Fucose-binding protein C72R | Arginine residue | —*3 |
| Fucose-binding protein C72E | Glutamic acid residue | —*3 |
| Fucose-binding protein C72D | Aspartic acid residue | —*3 |
| Fucose-binding protein C72V | Valine residue | —*3 |
| Fucose-binding protein C72L | Leucine residue | —*3 |
| Fucose-binding protein C72I | Isoleucine residue | —*3 |

*1Amino acid substitution of the cysteine residue at position 86 in the amino acid sequence of recombinant BC2LCNcys (SEQ ID NO: 36)
*2Relative value with respect to the sugar-chain binding capacity after treatment at room temperature, which is taken as 100%
*3Sugar-chain binding capacity was lost after treatment at room temperature (4) Measurement of Denaturation Midpoint Temperatures The fucose-binding protein C72G, the fucose-binding protein C72A, and the fucose-binding protein C72W, which exhibited sugar-chain binding capacity even after the heat treatment at 73° C. for 30 minutes in (3); and the recombinant BC2LCN(155)cys; were subjected to measurement of the denaturation midpoint temperature by the method described in (2) of Example 12. The results are shown in Table 12. As shown in Table 12, it can be seen that the fucose-binding protein C72G (wherein the cysteine residue identified as the cysteine residue at position 72 in SEQ ID NO: 1 is substituted with a glycine residue) and the fucose-binding protein C72A (wherein the cysteine residue identified as the cysteine residue at position 72 in SEQ ID NO: 1 is substituted with an alanine residue) have higher denaturation midpoint temperatures, that is, improved thermal stabilities, compared to the recombinant BC2LCN(155)cys (wherein the cysteine residue identified as the cysteine residue at position 72 in SEQ ID NO: 1 is not substituted). On the other hand, it can be seen that the fucose-binding protein C72W (wherein the cysteine residue identified as the cysteine residue at position 72 in SEQ ID NO: 1 is substituted with a tryptophan residue) has a lower denaturation midpoint temperature, that is, a lower thermal stability, compared to the recombinant BC2LCN(155)cys.
[Table 12]

TABLE 12

| Recombinant protein | Denaturation midpoint temperature (° C.) |
|---|---|
| Fucose-binding protein C72G | 88.2 ± 0.5 |
| Fucose-binding protein C72A | 83.2 ± 0.5 |
| Fucose-binding protein C72W | 75.6 ± 0.5 |
| Recombinant BC2LCN(155)cys | 82.3 ± 0.5 |

(5) Evaluation of Sugar-Chain Binding Affinities of Recombinant Proteins

The fucose-binding protein C72G and the fucose-binding protein C72A, which were found to have higher thermal stabilities than the recombinant BC2LCN(155)cys in (4), were subjected to evaluation of the binding affinities to H type 1 sugar chain and H type 3 sugar chain by the method described in (2) of Example 7. Table 13 shows the dissociation constants of the fucose-binding protein C72G, the fucose-binding protein C72A, and the recombinant BC2LCN(155)cys for H type 1 sugar chain and H type 3 sugar chain. As shown in Table 13, it can be seen that the fucose-binding protein C72G and the fucose-binding protein C72A have higher binding affinities to H type 1 sugar chain and H type 3 sugar chain than the recombinant BC2LCN(155)cys.
[Table 13]

TABLE 13

| | Dissociation constant (nM) | |
|---|---|---|
| Recombinant protein | H type 1 sugar chain | H type 3 sugar chain |
| Fucose-binding protein C72G | 2.1 | 5.3 |
| Fucose-binding protein C72A | 1.0 | 4.5 |
| Recombinant BC2LCN(155)cys | 3.9 | 11.0 |

Example 14 Production of Adsorbent 129 by Immobilization of Fucose-Binding Protein 129 on Insoluble Carrier Examples 14 to 17 are related to production of adsorbents by immobilization of each of the fucose-binding proteins produced in Examples 1 to 4 on an insoluble carrier. More specifically, as the insoluble carrier, a commercially available porous synthetic polymer-based carrier (Toyopearl HW-40EC, manufactured by Tosoh Corporation) was used. For immobilization of a fucose-binding protein having an oligopeptide containing a cysteine residue added thereto as a carrier-immobilization tag, a functional group (maleimide group) was introduced to the carrier. Thereafter, by reacting the mercapto group of the cysteine residue of the protein with the maleimide group, an adsorbent containing the protein immobilized on the insoluble carrier was produced.

Unless otherwise specified, in the following Examples 14 to 24, Comparative Examples 4 to 10, and Reference Examples 4 to 10, the weight of the insoluble carrier is the wet weight obtained by suspending the insoluble carrier in water and filtering the resulting suspension through a glass filter, followed by weighing the insoluble carrier. The "volume" of the insoluble carrier is the volume obtained by suspending the insoluble carrier in water and placing the resulting suspension in a graduated container, followed by leaving the suspension for not less than 12 hours and measuring the precipitation volume by visual observation.

Example 14 is related to production of an adsorbent (hereinafter referred to as adsorbent 129) by immobilization of the fucose-binding protein 129 produced in Example 1 on an insoluble carrier.
(1) Immobilization of Hydrophilic Polymer on Insoluble Carrier Toyopearl HW-40EC (manufactured by Tosoh Corporation, 100 to 300 μm) suspended in water was wet-classified into a particle size range of 150 to 250 μm using a standard stainless-steel sieve, and filtered through a glass filter. In the following Comparative Examples, when the Toyopearl HW-40EC classified into 150 to 250 μm is evaluated as an adsorbent, it is referred to as adsorbent A. The adsorbent HW-40EC in the water-wet state had an average particle size of 180 μm and a particle size range of 150 to 250 μm.

Subsequently, 10.0 g of Toyopearl HW-40EC, 10.8 mL (54 mmol) of 5M aqueous NaOH solution (manufactured by Kanto Chemical Co., Ltd.), and 5.0 mL of water were placed in a 250-mL Teflon (registered trademark) container, and then a mixed solution of 5.0 g (54 mmol) of epichlorohydrin (manufactured by Tokyo Chemical Industry Co., Ltd.) and 5.0 mL of dimethyl sulfoxide (DMSO, manufactured by Kanto Chemical Co., Ltd.) was added thereto, followed by shaking the resulting mixture in a shaker at 30° C. for 3 hours, to allow epoxidation of the Toyopearl HW-40EC. After the reaction, the solution was washed with water on a glass filter until the filtrate became neutral. The whole amount of the epoxidized Toyopearl HW-40EC was placed in a 250-mL Teflon (registered trademark) container, and 15.0 g of 30% by weight aqueous dextran solution (prepared from a product manufactured by Sigma-Aldrich (molecular weight, 450,000 to 650,000)) was added thereto, followed by shaking the resulting mixture in a shaker at 30° C. for 30 minutes. Subsequently, 1.05 mL (1.58 g, 19 mmol) of 48% aqueous NaOH solution was added to the reaction container, and the resulting mixture was further shaken in a shaker at 30° C. for 18 hours, to immobilize dextran on the epoxidized Toyopearl HW-40EC. After the reaction, the solution was washed with water on a glass filter until the filtrate became neutral, to prepare the desired dextran-immobilized Toyopearl HW-40EC (hereinafter referred to as DEX550 Toyopearl HW-40EC).

(2) Introduction of Maleimide Groups to Insoluble Carrier on Which Hydrophilic Polymer Is Immobilized In a 100-mL Teflon (registered trademark) container, 5.0 g of DEX550 Toyopearl HW-40EC, and 10.0 mL of an aqueous tetraethylene glycol diglycidyl ether solution preliminarily prepared (prepared from Denacol EX-821, manufactured by Nagase ChemteX Corporation; concentration, 100 mg/mL) were placed, and the mixture was shaken in a shaker at 30° C. for 30 minutes, followed by adding 104 μL (156 mg, 1.87 mmol) of 48% (about 18.1 M) aqueous NaOH solution to the reaction container and shaking the resulting mixture in a shaker at 30° C. for 8 hours, to prepare epoxidized DEX550 Toyopearl HW-40E. After the reaction, the reaction mixture was washed with water on a glass filter until the filtrate became neutral. The whole amount of the filtered epoxidized DEX550 Toyopearl HW-40EC was placed in a 100-mL Teflon (registered trademark) container, and 10.0 mL of 0.5 M aqueous ethylenediamine solution (prepared from ethylenediamine manufactured by Tokyo Chemical Industry Co., Ltd.) was added thereto, followed by shaking the resulting mixture in a shaker at 50° C. for 3 hours, to prepare aminated DEX550 Toyopearl HW-40EC. After the reaction, the reaction mixture was washed with water on a glass filter until the filtrate became neutral. The whole amount of the filtered aminated DEX550 Toyopearl HW-40EC was placed in a 100-mL Teflon (registered trademark) container, and 10.0 mL of a solution of 3-maleimidopropionic acid N-succinimidyl in DMSO (prepared from 3-maleimidopropionic acid N-succinimidyl manufactured by FUJIFILM Wako Pure Chemical Corporation; concentration, 10 mg/mL) was added thereto, followed by shaking the resulting mixture in a shaker at 35° C. for 4 hours, to allow maleimide modification of the aminated Toyopearl HW-40EC. After the reaction, the reaction mixture was washed three times with 20 mL of DMSO, and five times with 30 mL of water on a glass filter, to prepare the desired maleimide-modified DEX550 Toyopearl HW-40EC.

(3) Immobilization of Fucose-Binding Protein on Insoluble Carrier to Which Maleimide Groups are Introduced As a fucose-binding protein, the purified 129 solution (solution of the fucose-binding protein 129 in D-PBS(−)) prepared in Example 1 was used. The maleimide-modified DEX550 Toyopearl HW-40EC was suspended in water, and then filtered through a glass filter before use.

To 920 μL of the purified 129 solution (concentration, 9.75 mg/mL), 5.02 mL of D-PBS(−) and 60 μL of 100 mM aqueous TCEP solution were added, to prepare an immobilization protein solution. In a 100-mL Teflon (registered trademark) container, 4.5 g of the maleimide-modified DEX550 Toyopearl HW-40EC (which corresponds to 6.0 mL in the state of an aqueous suspension) was placed, and then 6.0 mL of an immobilization buffer (0.2 M sodium phosphate, 0.5 M sodium chloride, 20 mM EDTA; pH 7.4) was added thereto. Subsequently, 6.0 mL of the immobilization protein solution (the concentration of the fucose-binding protein 129 added, 1.5 mg/mL-carrier) was added thereto, and the resulting mixture was shaken at 35° C. for 15 hours, to immobilize the protein on the maleimide-modified Toyopearl HW-40EC, to produce the desired adsorbent 129.

The adsorbent 129 obtained was washed with D-PBS(−), and then the amount of the fucose-binding protein 129 in the washing solution was measured using a Micro BCA Protein Assay Kit (manufactured by Thermo Fisher Scientific Inc.). From the amount of the fucose-binding protein 129 added before the immobilization reaction, the fucose-binding protein 129 collected was subtracted to calculate the amount of the fucose-binding protein 129 immobilized per 1 mL of the adsorbent 129. As a result, the immobilized amount was found to be 193 μg/mL-adsorbent. The adsorbent 129 in the water-wet state had an average particle size of 177 μm and a particle size range of 150 to 250 μm.

(4) Introduction of Bromoacetyl Groups to Insoluble Carrier on Which Hydrophilic Polymer Is Immobilized In a 100-mL Teflon container, 5.0 g of the aminated DEX550 Toyopearl HW-40EC prepared in (3) of Example 14 was placed, and 10.0 mL of a solution of N-(bromoacetoxy) succinimide in DMSO (prepared from N-(bromoacetoxy) succinimide manufactured by Tokyo Chemical Industry Co., Ltd.; concentration, 10 mg/mL) was added thereto, followed by shaking the resulting mixture in a shaker at 25° C. for 4 hours, to allow haloacetylation of the aminated Toyopearl HW-40EC. After the reaction, the reaction mixture was washed three times with 20 mL of DMSO, and five times with 30 mL of water on a glass filter, to prepare the desired bromoacetylated DEX550 Toyopearl HW-40EC.

(5) Immobilization of Fucose-Binding Protein on Insoluble Carrier to Which Bromoacetyl Groups are Introduced The fucose-binding protein 129 was immobilized by the same method as in (3) of Example 14 except that the bromoacetylated DEX550 Toyopearl HW-40EC was used instead of the maleimide-modified DEX550 Toyopearl HW-40EC, to produce the desired adsorbent 129Br.

For the adsorbent 129Br obtained, the amount of the fucose-binding protein 129 immobilized per 1 mL of the adsorbent 129Br was calculated by the method described in (3) of Example 14. As a result, the immobilized amount was found to be 155 μg/mL-adsorbent. The adsorbent 129B in the water-wet state had an average particle size of 177 μm and a particle size range of 150 to 250 μm.

Example 15 Production of Adsorbent 127 by Immobilization of Fucose-Binding Protein 127 on Insoluble Carrier Example 15 is related to production of an adsorbent (hereinafter referred to as adsorbent 127) by immobilization of the fucose-binding protein 127 produced in Example 2 on an insoluble carrier.

The desired adsorbent 127 was produced by the same method as described in Example 14 except that the fucose-binding protein 127 produced in Example 2 was used instead of the fucose-binding protein 129 produced in Example 1.

According to the method described in (3) of Example 14, the amount of the fucose-binding protein 127 immobilized per 1 mL of the adsorbent 127 was calculated. As a result, the immobilized amount was found to be 351 μg/mL-adsorbent. The adsorbent 127 in the water-wet state had an average particle size of 175 μm and a particle size range of 150 to 250 μm.

Example 16 Production of Adsorbent 129G36C by Immobilization of Fucose-Binding Protein 129G36C on Insoluble Carrier Example 16 is related to production of an adsorbent (hereinafter referred to as adsorbent 129G36C) by immobilization of the fucose-binding protein 129G36C produced in Example 3 on an insoluble carrier.

The desired adsorbent 129G36C was produced by the same method as described in Example 14 except that the fucose-binding protein 129G36C produced in Example 3 was used instead of the fucose-binding protein 129 produced in Example 1.

According to the method described in (3) of Example 14, the amount of the fucose-binding protein 129G36C immobilized per 1 mL of the adsorbent 129G36C was calculated. As a result, the immobilized amount was found to be 244 μg/mL-adsorbent. The adsorbent 129G36C in the water-wet state had an average particle size of 176 μm and a particle size range of 150 to 250 μm.

Example 17 Production of Adsorbent 127G36C by Immobilization of Fucose-Binding Protein 127G36C on Insoluble Carrier Example 17 is related to production of an adsorbent (hereinafter referred to as adsorbent 127G36C) by immobilization of the fucose-binding protein 127G36C produced in Example 4 on an insoluble carrier.

The desired adsorbent 127G36C was produced by the same method as described in Example 14 except that the fucose-binding protein 127G36C produced in Example 4 was used instead of the fucose-binding protein 129 produced in Example 1.

According to the method described in (3) of Example 14, the amount of the fucose-binding protein 127G36C immobilized per 1 mL of the adsorbent 127G36C was calculated. As a result, the immobilized amount was found to be 245 μg/mL-adsorbent. The adsorbent 127G36C in the water-wet state had an average particle size of 180 μm and a particle size range of 150 to 250 μm.

Reference Example 3 Production of Adsorbent 155 by Immobilization of Recombinant BC2LCN(155)cys on Insoluble Carrier Reference Example 3 is related to production of an adsorbent by immobilization of the recombinant BC2LCN (155)cys produced in Comparative Example 1 on an insoluble carrier. More specifically, as the insoluble carrier, a commercially available porous synthetic polymer-based carrier (Toyopearl HW-40EC, manufactured by Tosoh Corporation) was used. For immobilization of the recombinant BC2LCN(155)cys having an oligopeptide containing a cysteine residue added thereto as a carrier-immobilization tag, a functional group (maleimide group) was introduced to the carrier. Thereafter, by reacting the mercapto group of the cysteine residue of the protein with the maleimide group, an adsorbent (hereinafter referred to as adsorbent 155) containing the protein immobilized on the insoluble carrier was produced.

The desired adsorbent 155 was produced by the same method as described in Example 14 except that the recombinant BC2LCN(155)cys produced in Comparative Example 1 was used instead of the fucose-binding protein 129 produced in Example 1.

According to the method described in (3) of Example 14, the amount of the fucose-binding protein 155 immobilized per 1 mL of the adsorbent 155 was calculated. As a result, the immobilized amount was found to be 298 μg/mL-adsorbent. The adsorbent 155 in the water-wet state had an average particle size of 178 μm and a particle size range of 150 to 250 μm.

Example 18 Evaluation of Cell Adsorption Capacities of Adsorbents—1

Examples 18 to 24, Comparative Examples 4 to 10, and Reference Examples 4 to 10 are related to evaluation of the cell adsorption capacities and the cell separation capacities of the adsorbents produced in Examples 14 to 17 and Reference Example 3.

Example 18 is related to evaluation of the cell adsorption capacities of the adsorbent 129, adsorbent 127, adsorbent 129G36C, and adsorbent 127G36C using human embryonal carcinoma cells (C1.4/D3, obtained from Cosmo Bio Co., Ltd.; hereinafter referred to as 2102Ep cells), which have a sugar chain containing a structure composed of "Fucα1-2Galβ1-3GlcNAc and/or Fucα1-2Galβ1-3GalNAc".

(1) Preparation of Columns Packed with Adsorbents

Columns were prepared by attaching a polyester mesh filter (manufactured by BioLab) having a mesh size of 40 μm between a 2.5-mL syringe (manufactured by Terumo Corporation) and an injection needle (manufactured by Terumo Corporation; 22 G). Subsequently, the adsorbent 129 prepared in Example 14, the adsorbent 127 produced in Example 15, the adsorbent 129G36C produced in Example 16, and the adsorbent 127G36C produced in Example 17 were subjected to replacement with MACS buffer, and prepared into 50% adsorbent suspensions such that the precipitation volume after being left to stand for not less than 12 hours was 50%. Into each column prepared, 1.0 mL of each suspension was applied for packing the column with each adsorbent (adsorbent volume, 500 μL).

(2) Culture of 2102Ep Cells and Preparation of Cell Suspension for Evaluation

2102Ep cells are adherent cells. Using D-MEM medium (High Glucose, manufactured by FUJIFILM Wako Pure Chemical Corporation) supplemented with 10% FBS (manufactured by Biological Industries) and an antibiotic solution (penicillin-streptomycin solution, manufactured by FUJIFILM Wako Pure Chemical Corporation), the cells were plated on a petri dish for adherent culture (manufactured by Corning) having a diameter of 6 cm, or on a petri dish for adherent culture (manufactured by Corning) having a diameter of 10 cm, and cultured in an atmosphere of 5% $CO_2$ at 37° C.

After the culture, the 2102Ep cells were fluorescently stained using Cell Tracker Orange (manufactured by Thermo Fisher Scientific Inc.) by the following method. The medium in the petri dish during the culture of the 2102Ep cells was discarded, and then the cells were washed by addition of D-PBS(−), followed by discarding the D-PBS (−). Subsequently, a solution prepared by dissolving Cell Tracker Orange in serum-free RPMI 1640 medium (manufactured by FUJIFILM Wako Pure Chemical Corporation) at a final concentration of 10 μM was added, and culture was performed in an atmosphere of 5% $CO_2$ at 37° C. for 1 hour.

After discarding the fluorescent reagent solution, the D-MEM medium supplemented with 10% FBS and the antibiotic solution was added, and culture was performed in an atmosphere of 5% $CO_2$ at 37° C. for 1 hour. Subsequently, the D-MEM medium was discarded, and fresh D-MEM medium was added again, followed by performing culture in an atmosphere of 5% $CO_2$ at 37° C. overnight.

Subsequently, collection of cells and preparation of a cell suspension were carried out by the following method. The D-MEM medium in the petri dish during the cell culture was discarded, and then D-PBS(–) was added, followed by washing the cells and discarding the D-PBS(–). Subsequently, an appropriate amount of Accutase (manufactured by Innovative Cell Technologies, Inc.) was added, and then the petri dish was left to stand for several minutes to detach the 2102Ep cells, followed by collecting the detached cells into a 50-mL tube. After precipitating the cells by centrifugation, the cells were suspended in the MACS buffer, and centrifugation was carried out again, followed by discarding the supernatant to wash the cells. After carrying out the cell washing operation twice, the cells were suspended in MACS buffer, and filtered using a cell strainer, to prepare a cell suspension of the 2102Ep cells stained with Cell Tracker Orange.

(3) Evaluation of Adsorption Capacities for 2102Ep Cells Using Columns Packed with Adsorbents The column packed with each adsorbent was placed in an upright position, and the cell suspension of 2102Ep cells prepared by the method described above was applied to the column in an amount of $1.1 \times 10^7$ cells/mL-adsorbent.

Subsequently, 4 mL of MACS buffer was applied from the top of the column, and the effluent from the needle section was collected into another container (the cell suspension is hereinafter referred to as effluent cell suspension). Into a FluoroNunc 96-well plate for detection of fluorescence (manufactured by Thermo Fisher Scientific Inc.), 100 μL of each effluent cell suspension collected was dispensed, and the plate was subjected to measurement of the fluorescence intensity at an excitation wavelength of 541 nm and a detection wavelength of 580 nm using a plate reader (Infinite M200, manufactured by TECAN). At the same time, a dilution series was prepared using the cell suspension of 2102Ep cells stained with Cell Tracker Orange, and 100 μL of each dilution was dispensed into a FluoroNunc 96-well plate for detection of fluorescence. By fluorescence scanning at an excitation wavelength of 541 nm and a detection wavelength of 580 nm using a plate reader, a calibration curve was prepared for the concentration and fluorescence intensity of the 2102Ep cells stained with Cell Tracker Orange. Based on the fluorescence intensity of each effluent cell suspension and the calibration curve obtained by the method described above, the number of cells contained in each effluent cell suspension was calculated, and the effluent rate of the 2102Ep cells in each effluent cell suspension was calculated as follows: "effluent rate=number of effluent cells per column/number of cells added".

Table 14 shows the effluent rate of the 2102Ep cells evaluated for each adsorbent. The effluent rate for the adsorbent 129 was 2.7%; the effluent rate for the adsorbent 127 was 2.9%; the effluent rate for the adsorbent 129G36C was 3.0%; and the effluent rate for the adsorbent 127G36C was 2.6%. Thus, it became clear that all of the adsorbents prepared by immobilizing the fucose-binding proteins of the present invention on the insoluble carrier have 2102Ep-cell adsorption capacities of as high as more than 95%.

Comparative Example 4 Evaluation of Cell Adsorption Capacity of Adsorbent Having No Fucose-Binding Protein Immobilized Thereon—1

Comparative Example 4 is related to evaluation of the adsorption capacity of adsorbent A, which has no fucose-binding protein immobilized thereon, for 2102Ep cells.

By the method described in (1) of Example 18, adsorbent A was packed into a column (adsorbent volume: 500 μL). Subsequently, using the cell suspension of 2102Ep cells prepared in (2) of Example 18, application of the cell suspension to the column packed with the adsorbent, collection of the effluent cell suspension, and measurement of the fluorescence intensity of the effluent cell suspension were sequentially carried out by the method described in (3) of Example 18. As a result of calculation of the effluent rate of the 2102Ep cells for adsorbent A, the effluent rate was found to be 88.2% (Table 14). Thus, it became clear that adsorbent A, which has no fucose-binding protein immobilized thereon, hardly adsorbs 2102Ep cells.

Reference Example 4 Evaluation of Cell Adsorption Capacity of Adsorbent Prepared by Immobilization of Recombinant BC2LCN(155)cys—1

Reference Example 4 is related to evaluation of the adsorption capacity of adsorbent 155, which was prepared by immobilization of the recombinant BC2LCN(155)cys, for 2102Ep cells.

By the method described in (1) of Example 18, adsorbent 155 was packed into a column (adsorbent volume: 500 μL). Subsequently, using the cell suspension of 2102Ep cells prepared in (2) of Example 18, application of the cell suspension to the column packed with the adsorbent, collection of the effluent cell suspension, and measurement of the fluorescence intensity of the effluent cell suspension were sequentially carried out by the method described in (3) of Example 18. As a result of calculation of the effluent rate of the 2102Ep cells for adsorbent 155, the effluent rate was found to be 2.9% (Table 14). Thus, it became clear that adsorbent 155, which was prepared by immobilizing the recombinant BC2LCN(155)cys on the insoluble carrier, also has a 2102Ep-cell adsorption capacity of as high as more than 95% similarly to the adsorbents prepared by immobilizing the fucose-binding proteins on the insoluble carrier.

[Table 14]

TABLE 14

| Example/ Comparative Example/ Reference Example | Adsorbent | 2102Ep cell effluent rate |
|---|---|---|
| Example 18 | Adsorbent 129 | 2.7% |
| | Adsorbent 127 | 2.9% |
| | Adsorbent 129G36C | 3.0% |
| | Adsorbent 127G36C | 2.6% |
| Comparative Example 4 | Adsorbent A | 88.2% |
| Reference Example 4 | Adsorbent 155 | 2.9% |

Example 19 Evaluation of Cell Adsorption Capacities of Adsorbents—2

Example 19 is related to evaluation of the cell adsorption capacities of adsorbent 129, adsorbent 127, adsorbent 129G36C, and adsorbent 127G36C using human lung adenocarcinoma cells (PC-9 cells; obtained from DS Pharma Biomedical Co., Ltd.; ECACC cell line number: 90071810), which have a sugar chain containing a structure composed of "Fucα1-2Galβ1-3GlcNAc and/or Fucα1-2Galβ1-3Gal-NAc".

(1) Preparation of Columns Packed with Adsorbents

By the method described in (1) of Example 18, columns packed with the above-described adsorbents were prepared (adsorbent volume: 500 μL).

(2) Culture of PC-9 Cells and Preparation of Cell Suspension for Evaluation

PC-9 cells are adherent cells. Using RPMI 1640 medium (manufactured by FUJIFILM Wako Pure Chemical Corporation) supplemented with 10% FBS (manufactured by Biological Industries) and an antibiotic solution (penicillin-streptomycin solution, manufactured by FUJIFILM Wako Pure Chemical Corporation), the cells were plated on a petri dish for adherent culture (manufactured by Corning) having a diameter of 6 cm, or on a petri dish for adherent culture (manufactured by Corning) having a diameter of 10 cm, and cultured in an atmosphere of 5% $CO_2$ at 37° C.

After the culture, a cell suspension of PC-9 cells stained with Cell Tracker Orange was prepared by the method described in (2) of Example 18.

(3) Evaluation of Adsorption Capacities for PC-9 Cells Using Columns Packed with Adsorbents The column packed with each adsorbent was placed in an upright position, and the cell suspension of PC-9 cells prepared by the method described above was applied to the column in an amount of $4.8 \times 10^6$ cells/mL-adsorbent. Thereafter, by the method described in (3) of Example 18, an effluent cell suspension was collected from each adsorbent, and the effluent rate of PC-9 cells was calculated. Preparation of a calibration curve for the concentration and fluorescence intensity of the PC-9 cells stained with Cell Tracker Orange was carried out according to the method described in (3) of Example 18.

Table 15 shows the effluent rate of the PC-9 cells evaluated for each adsorbent. The effluent rate for the adsorbent 129 was 2.5%; the effluent rate for the adsorbent 127 was 2.4%; the effluent rate for the adsorbent 129G36C was 2.6%; and the effluent rate for the adsorbent 127G36C was 2.5%. Thus, it became clear that all of the adsorbents prepared by immobilizing the fucose-binding proteins of the present invention on the insoluble carrier have PC-9-cell adsorption capacities of as high as more than 95%.

Comparative Example 5 Evaluation of Cell Adsorption Capacity of Adsorbent Having No Fucose-Binding Protein Immobilized Thereon—2

Comparative Example 5 is related to evaluation of the adsorption capacity of adsorbent A, which has no fucose-binding protein immobilized thereon, for PC-9 cells.

By the method described in (1) of Example 18, adsorbent A was packed into a column (adsorbent volume: 500 μL). Subsequently, using the cell suspension of PC-9 cells prepared in (2) of Example 19, application of the cell suspension to the column packed with the adsorbent, collection of the effluent cell suspension, and measurement of the fluorescence intensity of the effluent cell suspension were sequentially carried out by the method described in (3) of Example 19. As a result of calculation of the effluent rate of the PC-9 cells for adsorbent A, the effluent rate was found to be 95.2% (Table 15). Thus, it became clear that adsorbent A, which has no fucose-binding protein immobilized thereon, hardly adsorbs PC-9 cells.

Reference Example 5 Evaluation of Cell Adsorption Capacity of Adsorbent Prepared by Immobilization of Recombinant BC2LCN(155)cys—2

Reference Example 5 is related to evaluation of the cell adsorption capacity of adsorbent 155, which was prepared by immobilization of the recombinant BC2LCN(155)cys, for PC-9 cells.

By the method described in (1) of Example 18, adsorbent 155 was packed into a column (adsorbent volume: 500 μL). Subsequently, using the cell suspension of PC-9 cells prepared in (2) of Example 19, application of the cell suspension to the column packed with the adsorbent, collection of the effluent cell suspension, and measurement of the fluorescence intensity of the effluent cell suspension were sequentially carried out by the method described in (3) of Example 19. As a result of calculation of the effluent rate of the PC-9 cells for adsorbent 155, the effluent rate was found to be 2.4% (Table 15). Thus, it became clear that adsorbent 155, which was prepared by immobilizing the recombinant BC2LCN(155)cys on the insoluble carrier, also has a PC-9-cell adsorption capacity of as high as more than 95% similarly to the adsorbents prepared by immobilizing the fucose-binding proteins on the insoluble carrier.

[Table 15]

TABLE 15

| Example/ Comparative Example/ Reference Example | Adsorbent | PC-9 cell effluent rate |
|---|---|---|
| Example 19 | Adsorbent 129 | 2.5% |
| | Adsorbent 127 | 2.4% |
| | Adsorbent 129G36C | 2.6% |
| | Adsorbent 127G36C | 2.5% |
| Comparative Example 5 | Adsorbent A | 95.2% |
| Reference Example 5 | Adsorbent 155 | 2.4% |

Example 20 Evaluation of Cell Adsorption Capacities of Adsorbents—3

Example 20 is related to evaluation of the cell adsorption capacities of adsorbent 129, adsorbent 127, adsorbent 129G36C, and adsorbent 127G36C using human Burkitt lymphoma cells (Ramos cells, JCRB9119), which have no sugar chain containing a structure composed of "Fucα1-2Galβ1-3GlcNAc and/or Fucα1-2Galβ1-3GalNAc".

(1) Preparation of Columns Packed with Adsorbents

By the method described in (1) of Example 18, columns packed with the above-described adsorbents were prepared (adsorbent volume: 500 μL).

(2) Culture of Ramos Cells and Preparation of Cell Suspension for Evaluation

Ramos cells are floating cells. Using RPMI 1640 medium (manufactured by FUJIFILM Wako Pure Chemical Corporation) supplemented with 10% FBS (manufactured by Biological Industries) and an antibiotic solution (penicillin-streptomycin solution, manufactured by FUJIFILM Wako Pure Chemical Corporation), the cells were plated on a petri dish for suspension culture (manufactured by Sumitomo Bakelite Co., Ltd.), and cultured in an atmosphere of 5% $CO_2$ at 37° C.

After the culture, a cell suspension of Ramos cells stained with Cell Tracker Orange was prepared by the method described in (2) of Example 18.

(3) Evaluation of Adsorption Capacities for Ramos Cells Using Columns Packed with Adsorbents The column packed with each adsorbent was placed in an upright position, and the cell suspension of Ramos cells prepared by the method described above was applied to the column in an amount of $1.4 \times 10^7$ cells/mL-adsorbent. Thereafter, by the method described in (3) of Example 18, an effluent cell suspension was collected from each adsorbent, and the effluent rate of Ramos cells was calculated. Preparation of a calibration curve for the concentration and fluorescence intensity of the Ramos cells stained with Cell Tracker Orange was carried out according to the method described in (3) of Example 18.

Table 16 shows the effluent rate of the Ramos cells evaluated for each adsorbent. The effluent rate for the adsorbent 129 was 99%; the effluent rate for the adsorbent 127 was 102%; the effluent rate for the adsorbent 129G36C was 99%; and the effluent rate for the adsorbent 127G36C was 101%. Thus, it became clear that the adsorbents prepared by immobilizing the fucose-binding proteins of the present invention on the insoluble carrier do not adsorb Ramos cells.

Comparative Example 6 Evaluation of Cell Adsorption Capacity of Adsorbent Having No Fucose-Binding Protein Immobilized Thereon—3

Comparative Example 6 is related to evaluation of the adsorption capacity of adsorbent A, which has no fucose-binding protein immobilized thereon, for Ramos cells.

By the method described in (1) of Example 18, adsorbent A was packed into a column (adsorbent volume: 500 μL). Subsequently, using the cell suspension of Ramos cells prepared in (2) of Example 20, application of the cell suspension to the column packed with the adsorbent, collection of the effluent cell suspension, and measurement of the fluorescence intensity of the effluent cell suspension were sequentially carried out by the method described in (3) of Example 20. As a result of calculation of the effluent rate of the Ramos cells for adsorbent A, the effluent rate was found to be 101% (Table 16). Thus, it became clear that adsorbent A, which has no fucose-binding protein immobilized thereon, also has no adsorption capacity for Ramos cells.

Reference Example 6 Evaluation of Cell Adsorption Capacity of Adsorbent Prepared by Immobilization of Recombinant BC2LCN(155)cys—3

Reference Example 6 is related to evaluation of the cell adsorption capacity of adsorbent 155, which was prepared by immobilization of the recombinant BC2LCN(155)cys, for Ramos cells.

By the method described in (1) of Example 18, adsorbent 155 was packed into a column (adsorbent volume: 500 μL). Subsequently, using the cell suspension of Ramos cells prepared in (2) of Example 20, application of the cell suspension to the column packed with the adsorbent, collection of the effluent cell suspension, and measurement of the fluorescence intensity of the effluent cell suspension were sequentially carried out by the method described in (3) of Example 20. As a result of calculation of the effluent rate of the Ramos cells for adsorbent 155, the effluent rate was found to be 102% (Table 16). Thus, it became clear that adsorbent 155, which was prepared by immobilizing the recombinant BC2LCN(155)cys on the insoluble carrier, also does not adsorb Ramos cells.

[Table 16]

TABLE 16

| Example/ Comparative Example/ Reference Example | Adsorbent | Ramos cell effluent rate |
|---|---|---|
| Example 20 | Adsorbent 129 | 99% |
| | Adsorbent 127 | 102% |
| | Adsorbent 129G36C | 99% |
| | Adsorbent 127G36C | 101% |
| Comparative Example 6 | Adsorbent A | 101% |
| Reference Example 6 | Adsorbent 155 | 102% |

Example 21 Evaluation of Cell Separation Capacity of Adsorbent—4

Example 21 is related to evaluation of the cell separation capacity of adsorbent 127, using a cell mixture of human lung adenocarcinoma cells (PC-9 cells), which have a sugar chain containing a structure composed of "Fucα1-2Galβ1-3GlcNAc and/or Fucα1-2Galβ1-3GalNAc", and K562 cells (JCRB0019), which are human chronic myelocytic leukemia cells having no sugar chain containing a structure composed of "Fucα1-2Galβ1-3GlcNAc and/or Fucα1-2Galβ1-3Gal-NAc".

(1) Production of Adsorbent 127, and Preparation of Column Packed with Adsorbent 127

Adsorbent 127 was produced according to the method described in Example 15. As a result of calculation of the amount of the fucose-binding protein 127 immobilized per 1 mL of the adsorbent 127, the immobilized amount was found to be 443 μg/mL-adsorbent. Subsequently, according to the method described in (1) of Example 18, a column packed with the adsorbent 127 produced was prepared (adsorbent volume: 500 μL).

(2) Culture of PC-9 Cells and K562 Cells, and Preparation of Cell Mixture for Evaluation PC-9 cells are adherent cells. The cells were cultured according to the method described in Example 19. After the culture, a cell suspension of PC-9 cells stained with Cell Tracker Green (manufactured by Thermo Fisher Scientific Inc.) was prepared according to the same method as described in (2) of Example 18 except that Cell Tracker Green was used instead of Cell Tracker Orange.

K562 cells are floating cells. Using GIT medium (manufactured by Nihon Pharmaceutical Co., Ltd.), the cells were plated on a petri dish for suspension culture (manufactured by Sumitomo Bakelite Co., Ltd.), and cultured in an atmosphere of 5% $CO_2$ at 37° C. After the culture, a cell suspension of K562 cells stained with Cell Tracker Orange was prepared by the method described in (2) of Example 18.

The number of cells in each of the cell suspension of PC-9 cells and the cell suspension of K562 cells prepared by the above method was measured, and the cell suspension of PC-9 cells and the cell suspension of K562 cells were mixed together such that a ratio of 1:1 was achieved in terms of the cell number, to prepare a cell mixture for evaluation of the cell separation capacity.

(3) Evaluation of Cell Separation Capacity Using Column Packed with Adsorbent

The column packed with each adsorbent was placed in an upright position, and the cell mixture prepared by the above method was applied to the column in an amount of $4.8 \times 10^6$ cells/mL-adsorbent, that is, such that the amount of each of the PC-9 cells and the K562 cells was $2.4 \times 10^6$ cells/mL-adsorbent.

Subsequently, 4 mL of MACS buffer was applied from the top of the column, and the effluent cell suspension from the needle section was collected into another container. Into a FluoroNunc 96-well plate for detection of fluorescence (manufactured by Thermo Fisher Scientific Inc.), 100 μL of the effluent cell suspension collected was dispensed, and the plate was subjected to measurement of the fluorescence intensity at an excitation wavelength of 492 nm and a detection wavelength of 530 nm, or an excitation wavelength of 541 nm and a detection wavelength of 580 nm using a plate reader (Infinite M200, manufactured by TECAN). At the same time, a dilution series was prepared using the cell suspension of PC-9 cells stained with Cell Tracker Green, and 100 μL of each dilution was dispensed into a FluoroNunc 96-well plate for detection of fluorescence. By measurement of the fluorescence intensity at an excitation wavelength of 492 nm and a detection wavelength of 530 nm using a plate reader, a calibration curve was prepared for the concentration and fluorescence intensity of the PC-9 cells stained with Cell Tracker Green. Preparation of a calibration curve for the concentration and fluorescence intensity of the K562 cells stained with Cell Tracker Orange was carried out according to the method described in (3) of Example 20. Based on the fluorescence intensity of the effluent cell suspension and the calibration curve obtained by the method described above, the number of each type of cells contained in the effluent cell suspension collected was calculated, and the effluent rates of the PC-9 cells and the K562 cells in the effluent cell suspension were calculated.

Table 17 shows the effluent rates of the PC-9 cells and the K562 cells for adsorbent 127. While the effluent rate of the PC-9 cells was 3.3%, the effluent rate of the K562 cells was 55.1%. Thus, it became clear that adsorbent 127, prepared by immobilizing the fucose-binding protein 127 of the present invention on the insoluble carrier, is capable of selectively separating PC-9 cell alone from a mixture of PC-9 cells and K562 cells.

Comparative Example 7 Evaluation of Cell Separation Capacity of Adsorbent Having No Fucose-Binding Protein Immobilized Thereon—4

Comparative Example 7 is related to evaluation of the cell separation capacity of adsorbent A, which has no fucose-binding protein immobilized thereon, using a cell mixture of PC-9 cells and K562 cells.

By the method described in (1) of Example 18, adsorbent A was packed into a column (adsorbent volume: 500 μL). Subsequently, using the cell mixture of PC-9 cells and K562 cells prepared in (2) of Example 21, application of the cell mixture to the column packed with the adsorbent, collection of the effluent cell suspension, and measurement of the fluorescence intensity of the effluent cell suspension were sequentially carried out by the method described in (3) of Example 21. As a result of calculation of the effluent rates of the PC-9 cells and the K562 cells for adsorbent A, the effluent rate of the PC-9 cells was found to be 50.2%, and the effluent rate of the K562 cells was found to be 55.4% (Table 17). Thus, it became clear that adsorbent A, which has no fucose-binding protein immobilized thereon, is not capable of separating PC-9 cells by adsorption from a mixture of PC-9 cells and K562 cells.

Reference Example 7 Evaluation of Cell Separation Capacity of Adsorbent Prepared by Immobilization of Recombinant BC2LCN(155)cys—4

Reference Example 7 is related to evaluation of the cell separation capacity of adsorbent 155, using a cell mixture of PC-9 cells and K562 cells.

Adsorbent 155 was produced according to the method described in Reference Example 3. As a result of calculation of the amount of the recombinant BC2LCN(155)cys immobilized per 1 mL of the adsorbent 155, the immobilized amount was found to be 485 μg/mL-adsorbent. Subsequently, by the method described in (1) of Example 18, the adsorbent 155 was packed into a column (adsorbent volume: 500 μL).

Using the cell mixture of PC-9 cells and K562 cells prepared in (2) of Example 21, application of the cell mixture to the column packed with the adsorbent, collection of the effluent cell suspension, and measurement of the fluorescence intensity of the effluent cell suspension were sequentially carried out by the method described in (3) of Example 21. As a result of calculation of the effluent rates of the PC-9 cells and the K562 cells for adsorbent A, the effluent rate of the PC-9 cells was found to be 10.0%, and the effluent rate of the K562 cells was found to be 58.3% (Table 17). Thus, it became clear that adsorbent 155, prepared by immobilizing the recombinant BC2LCN(155)cys on the insoluble carrier, is capable of selectively separating PC-9 cell alone from a mixture of PC-9 cells and K562 cells.

[Table 17]

TABLE 17

| Example/ Comparative Example/ Reference Example | Adsorbent | PC-9 cell effluent rate | K562 cell effluent rate |
|---|---|---|---|
| Example 21 | Adsorbent 127 | 3.3% | 55.1% |
| Comparative Example 7 | Adsorbent A | 50.2% | 55.4% |
| Reference Example 7 | Adsorbent 155 | 10.0% | 58.3% |

Example 22 Evaluation of Cell Adsorption Capacity of Adsorbent—5

Example 22 is related to evaluation of the cell adsorption capacity of adsorbent 127, using 201B7 cells (distributed from CiRA, Kyoto University after concluding a patent licensing agreement and an MTA agreement), which are a human iPS cell line having a sugar chain containing a structure composed of "Fucα1-2Galβ1-3GlcNAc and/or Fucα1-2Galβ1-3GalNAc".

(1) Preparation of Column Packed with Adsorbent

Using the adsorbent 127 prepared in (1) of Example 21, a column packed with the adsorbent 127 produced was prepared according to the method described in (1) of Example 18 (adsorbent volume: 500 μL).

(2) Culture of 201B7 Cells and Preparation of Cell Suspension for Evaluation

Culture of 201B7 cells was carried out by the following method using a petri dish for adherent culture (manufactured by Corning).

A solution of 3 μg/mL iMatrix-511 (manufactured by Nippi Inc.) preliminarily prepared by dilution with D-PBS was placed in the petri dish, and left to stand at 4° C. overnight or longer to allow coating of the culture surface of the petri dish with iMatrix-511. After discarding the iMatrix-511 solution from the coated petri dish, the dish was washed by addition of StemFit AK02N medium (manufactured by Ajinomoto Co., Inc.), which is an iPS cell culture medium. The same medium was supplemented with 10 UM ROCK Inhibitor (Y-27632, manufactured by FUJIFILM Wako Pure Chemical Corporation), and 201B7 cells thawed from a frozen vial were suspended therein, followed by plating the cells. After overnight culture, the StemFit AK02N medium containing Y-27632 was discarded, and replaced with Stem-Fit AK02N medium free of Y-27632. At the time when an appropriate cell density was achieved, the cells were collected and subcultured.

Collection of cells from the petri dish was carried out by the following method. An operation of adding D-PBS(-) to the petri dish to wash the cells and discarding the D-PBS(-) was carried out twice to wash the cells. Thereafter, a detachment solution prepared by mixing CTS TrypLE Select Enzyme (manufactured by Thermo Fisher Scientific Inc.) and Versene Solution (manufactured by Thermo Fisher Scientific Inc.) together at 1:1 was added to the petri dish, and the petri dish was left to stand in an atmosphere of 5% $CO_2$ at 37° C. for 1 minute. After confirming that the cells were becoming round and being detached, the detachment solution was discarded, and then StemFit AK02N medium containing 10 UM Y-27632 was added to the petri dish, followed by detaching the cells using a cell scraper and collecting the cells into a 50-mL tube. The number of cells collected was counted with a hemacytometer. The cells were then plated at a density of 104 to 105/mL in StemFit AK02N medium containing Y-27632, followed by continuation of culture in StemFit AK02N medium free of Y-27632 until an appropriate cell density was achieved.

Subsequently, fluorescent staining of 201B7 cells using Cell Tracker Orange was carried out by the following method. The medium in the petri dish was discarded, and then the cells were rinsed by addition of D-PBS(-), followed by sucking and discarding the D-PBS(-). Subsequently, a solution prepared by dissolving Cell Tracker Orange in serum-free RPMI 1640 medium at a final concentration of 20 μM was added, and culture was performed in an atmosphere of 5% $CO_2$ at 37° C. for 1 hour. After discarding the fluorescent reagent solution, StemFit AK02N medium was added, and culture was performed in an atmosphere of 5% $CO_2$ at 37° C. for 1 hour. After discarding the medium, StemFit AK02N medium was added, and culture was performed in an atmosphere of 5% $CO_2$ at 37° C. overnight. Subsequently, collection of cells and preparation of a cell suspension were carried out by the following method. An operation of adding D-PBS(-) to the petri dish to rinse the cells and discarding the D-PBS(-) was carried out twice to wash the cells. Thereafter, a detachment solution prepared by mixing CTS TrypLE Select Enzyme (manufactured by Thermo Fisher Scientific Inc.) and Versene Solution (manufactured by Thermo Fisher Scientific Inc.) together at 1:1 was added, and the cells were left to stand in an atmosphere of 5% $CO_2$ at 37° C. for 1 minute. After confirming that the cells were becoming round and being detached, the detachment solution was discarded, and then StemFit AK02N medium was added, followed by detaching the cells using a cell scraper and collecting the cells into a 50-mL tube. After precipitating the collected cells by centrifugation, the cells were suspended in MACS buffer, and centrifugation was carried out again, followed by discarding the supernatant to wash the cells. After carrying out the cell washing operation twice, the cells were suspended in MACS buffer, and filtered using a cell strainer, to prepare a cell suspension of 201B7 cells stained with Cell Tracker Orange.

(3) Evaluation of Adsorption Capacity for 201B7 Cells Using Column Packed with Adsorbent The column packed with adsorbent 127 was placed in an upright position, and the cell suspension of 201B7 cells prepared by the method described above was applied to the column in an amount of $4.4 \times 10^5$ cells/mL-adsorbent. Thereafter, by the method described in (3) of Example 18, an effluent cell suspension was collected from the adsorbent 127, and the effluent rate of 201B7 cells was calculated. As a result, the effluent rate of the 201B7 cells for the adsorbent 127 was found to be 0.5% (Table 18). Thus, it became clear that adsorbent 127, which was prepared by immobilizing the fucose-binding protein 127 of the present invention on the insoluble carrier, has a high iPS-cell adsorption capacity. Preparation of a calibration curve for the concentration and fluorescence intensity of the 201B7 cells stained with Cell Tracker Orange was carried out according to the method described in (3) of Example 18.

Comparative Example 8 Evaluation of Cell Adsorption Capacity of Adsorbent Having No Fucose-Binding Protein Immobilized Thereon—5

Comparative Example 8 is related to evaluation of the adsorption capacity of adsorbent A, which has no fucose-binding protein immobilized thereon, for 201B7 cells.

By the method described in (1) of Example 18, adsorbent A was packed into a column (adsorbent volume: 500 μL). Subsequently, using the cell suspension of 201B7 cells prepared in (2) of Example 22, application of the cell suspension to the column packed with the adsorbent, collection of the effluent cell suspension, and measurement of the fluorescence intensity of the effluent cell suspension were sequentially carried out by the method described in (3) of Example 22. As a result of calculation of the effluent rate of the 201B7 cells for adsorbent A, the effluent rate was found to be 77.0% (Table 18). Thus, it became clear that adsorbent A, which has no fucose-binding protein immobilized thereon, hardly adsorbs 201B7 cells.

Reference Example 8 Evaluation of Cell Adsorption Capacity of Adsorbent Prepared by Immobilization of Recombinant BC2LCN(155)cys—5

Reference Example 8 is related to evaluation of the adsorption capacity of adsorbent 155, which was prepared by immobilization of the recombinant BC2LCN(155)cys, for 201B7 cells.

Using the adsorbent 155 produced in (1) of Reference Example 7, a column packed with the adsorbent 155 was prepared according to the method described in (1) of Example 18 (adsorbent volume: 500 μL). Subsequently, using the cell suspension of 201B7 cells prepared in (2) of Example 22, application of the cell suspension to the column packed with the adsorbent, collection of the effluent cell suspension, and measurement of the fluorescence intensity of the effluent cell suspension were sequentially carried out by the method described in (3) of Example 22. As a result of calculation of the effluent rate of the 201B7 cells for adsorbent 155, the effluent rate was found to be 0.6% (Table 18). Thus, it became clear that adsorbent 155, which was prepared by immobilizing the recombinant BC2LCN(155) cys on the insoluble carrier, also has a high iPS-cell adsorption capacity.
[Table 18]

TABLE 18

| Example/ Comparative Example/ Reference Example | Adsorbent | 201B7 cell effluent rate |
| --- | --- | --- |
| Example 22 | Adsorbent 127 | 0.50% |
| Comparative Example 8 | Adsorbent A | 77.0% |
| Reference Example 8 | Adsorbent 155 | 0.60% |

Example 23 Evaluation of Cell Adsorption Capacity of Adsorbent—6

Example 23 is related to evaluation of the cell adsorption capacity of adsorbent 127 using NHDF cells (manufactured by PromoCell), which are normal human skin fibroblasts having no sugar chain containing a structure composed of "Fucα1-2Galβ1-3GlcNAc and/or Fucα1-2Galβ1-3Gal-NAc".
(1) Preparation of Column Packed with Adsorbent
Using the adsorbent 127 produced in (1) of Example 21, a column packed with the adsorbent 127 produced was prepared according to the method described in (1) of Example 18 (adsorbent volume: 500 μL).
(2) Culture of NHDF Cells and Preparation of Cell Suspension for Evaluation
NHDF cells are adherent cells. Using a fibroblast growth medium 2 (manufactured by PromoCell), the cells were plated on a petri dish for adherent culture (manufactured by Corning) having a diameter of 10 cm, or on a petri dish for adherent culture (manufactured by Corning) having a diameter of 15 cm, and cultured in an atmosphere of 5% $CO_2$ at 37° C. After the culture, a cell suspension of NHDF cells stained with Cell Tracker Green (manufactured by Thermo Fisher Scientific Inc.) was prepared according to the same method as described in (2) of Example 18 except that Cell Tracker Green was used instead of Cell Tracker Orange.
(3) Evaluation of Adsorption Capacity for NHDF Cells Using Column Packed with Adsorbent
The column packed with adsorbent 127 was placed in an upright position, and the cell suspension of NHDF cells prepared by the method described above was applied to the column in an amount of $8.2 \times 10^5$ cells/mL-adsorbent. Thereafter, by the method described in (3) of Example 18, an effluent cell suspension was collected from the adsorbent 127, and the effluent rate of NHDF cells was calculated. As a result, the effluent rate of the NHDF cells for the adsorbent 127 was found to be 90.3% (Table 19). Thus, it became clear that each adsorbent prepared by immobilizing the fucose-binding protein of the present invention on the insoluble carrier does not adsorb NHDF cells. Preparation of a calibration curve for the concentration and fluorescence intensity of the NHDF cells stained with Cell Tracker Green was carried out according to the method described in (3) of Example 21.

Comparative Example 9 Evaluation of Cell Adsorption Capacity of Adsorbent Having No Fucose-Binding Protein Immobilized Thereon—6

Comparative Example 9 is related to evaluation of the cell adsorption capacity of adsorbent A, which has no fucose-binding protein immobilized thereon, using NHDF cells.

By the method described in (1) of Example 18, adsorbent A was packed into a column (adsorbent volume: 500 μL). Subsequently, using the cell suspension of NHDF cells prepared in (2) of Example 23, application of the cell suspension to the column packed with the adsorbent, collection of the effluent cell suspension, and measurement of the fluorescence intensity of the effluent cell suspension were sequentially carried out by the method described in (3) of Example 23. As a result of calculation of the effluent rate of the NHDF cells for adsorbent A, the effluent rate was found to be 85.1% (Table 19). Thus, it became clear that adsorbent A, which has no fucose-binding protein immobilized thereon, hardly adsorbs NHDF cells.

Reference Example 9 Evaluation of Cell Adsorption Capacity of Adsorbent Prepared by Immobilization of Recombinant BC2LCN(155)cys—6

Reference Example 9 is related to evaluation of the cell adsorption capacity of adsorbent 155, using NHDF cells.
Using the adsorbent 155 produced in (1) of Reference Example 7, a column packed with the adsorbent 155 was prepared according to the method described in (1) of Example 18 (adsorbent volume: 500 μL). Subsequently, using the cell suspension of NHDF cells prepared in (2) of Example 23, application of the cell suspension to the column packed with the adsorbent, collection of the effluent cell suspension, and measurement of the fluorescence intensity of the effluent cell suspension were sequentially carried out by the method described in (3) of Example 23. As a result of calculation of the effluent rate of the NHDF cells for adsorbent 155, the effluent rate was found to be 104% (Table 19). Thus, it became clear that adsorbent 155, which was prepared by immobilizing the recombinant BC2LCN(155) cys on the insoluble carrier, does not adsorb NHDF cells.
[Table 19]

TABLE 19

| Example/ Comparative Example/ Reference Example | Adsorbent | NHDF cell effluent rate |
| --- | --- | --- |
| Example 23 | Adsorbent 127 | 90.3% |
| Comparative Example 9 | Adsorbent A | 85.1% |
| Reference Example 9 | Adsorbent 155 | 104% |

Example 24 Evaluation of Cell Separation Capacity of Adsorbent—7

Example 24 is related to evaluation of the cell separation capacity of adsorbent 127, using a cell mixture of 201B7 cells, which are a human iPS cell line having a sugar chain containing a structure composed of "Fucα1-2Galβ1-3GlcNAc and/or Fucα1-2Galβ1-3GalNAc", and NHDF cells, which have no sugar chain containing a structure composed of "Fucα1-2Galβ1-3GlcNAc and/or Fucα1-2Galβ1-3GalNAc".
(1) Preparation of Column Packed with Adsorbent
Using the adsorbent 127 produced in (1) of Example 21, a column packed with the adsorbent 127 produced was prepared according to the method described in (1) of Example 18 (adsorbent volume: 500 μL).
(2) Preparation of Cell Mixture for Evaluation
A cell suspension of 201B7 cells stained with Cell Tracker Orange, prepared in (2) of Example 22 was used. In addition, a cell suspension of NHDF cells stained with Cell Tracker Green, prepared in (2) of Example 23 was used.

The number of cells in each of the cell suspension of 201B7 cells and the cell suspension of NHDF cells was measured, and the cell suspension of 201B7 cells and the cell suspension of NHDF cells were mixed together at a ratio of 35:65 in terms of the cell numbers of the 201B7 cells and the NHDF cells, respectively, to prepare a cell mixture for evaluation of the cell separation capacity.

(3) Evaluation of Cell Separation Capacity Using Column Packed with Adsorbent

The column packed with each adsorbent was placed in an upright position, and the cell mixture prepared by the above method was applied to the column in an amount of $1.3 \times 10^6$ cells/mL-adsorbent, that is, such that the amounts of the 201B7 cells and the NHDF cells were $0.46 \times 10^6$ cells/mL-adsorbent and $0.84 \times 10^6$ cells/mL-adsorbent, respectively.

Thereafter, by the method described in (3) of Example 21, an effluent cell suspension was collected from the adsorbent 127, and the number of each type of cells contained in the effluent cell suspension collected was calculated. Thereafter, the effluent rates of the 201B7 cells and the NHDF cells in the effluent cell suspension were calculated.

Table 20 shows the effluent rates of the 201B7 cells and the NHDF cells for adsorbent 127. While the effluent rate of the 201B7 cells was 0.3%, the effluent rate of the NHDF cells was 78.4%. Thus, it became clear that adsorbent 127, prepared by immobilizing the fucose-binding protein 127 of the present invention on the insoluble carrier, is capable of selectively separating 201B7 cell alone from a mixture of 201B7 cells and NHDF cells.

Comparative Example 10 Evaluation of Cell Separation Capacity of Adsorbent Having No Fucose-Binding Protein Immobilized Thereon—7

Comparative Example 10 is related to evaluation of the cell separation capacity of adsorbent A, which has no fucose-binding protein immobilized thereon, using a cell mixture of 201B7 cells and NHDF cells.

By the method described in (1) of Example 18, adsorbent A was packed into a column (adsorbent volume: 500 μL). Subsequently, using the cell mixture of 201B7 cells and NHDF cells prepared in (2) of Example 24, application of the cell mixture to the column packed with the adsorbent, collection of the effluent cell suspension, and measurement of the fluorescence intensity of the effluent cell suspension were sequentially carried out by the method described in (3) of Example 24. As a result of calculation of the effluent rates of the 201B7 cells and the NHDF cells for adsorbent A, the effluent rate of the 201B7 cells was found to be 66.7%, and the effluent rate of the NHDF cells was found to be 83.7% (Table 20). Thus, it became clear that adsorbent A, which has no fucose-binding protein immobilized thereon, is not capable of separating 201B7 cells by adsorption from a mixture of 201B7 cells and NHDF cells.

Reference Example 10 Evaluation of Cell Separation Capacity of Adsorbent Prepared by Immobilization of Recombinant BC2LCN(155)cys—7

Reference Example 10 is related to evaluation of the cell separation capacity of adsorbent 155, using a cell mixture of 201B7 cells and NHDF cells.

Using the adsorbent 155 produced in (1) of Reference Example 7, a column packed with the adsorbent 155 was prepared according to the method described in (1) of Example 18 (adsorbent volume: 500 μL). Subsequently, using the cell mixture of 201B7 cells and NHDF cells prepared in (2) of Example 24, application of the cell mixture to the column packed with the adsorbent, collection of the effluent cell suspension, and measurement of the fluorescence intensity of the effluent cell suspension were sequentially carried out by the method described in (3) of Example 24. As a result of calculation of the effluent rates of the 201B7 cells and the NHDF cells for adsorbent A, the effluent rate of the 201B7 cells was found to be 0.6%, and the effluent rate of the NHDF cells was found to be 79.7% (Table 20). Thus, it became clear that adsorbent 155, prepared by immobilizing the recombinant BC2LCN(155)cys on the insoluble carrier, is capable of selectively separating 201B7 cell alone from a mixture of 201B7 cells and NHDF cells.

[Table 20]

TABLE 20

| Example/ Comparative Example/ Reference Example | Adsorbent | 201B7 cell effluent rate | NHDF cell effluent rate |
| --- | --- | --- | --- |
| Example 24 | Adsorbent 127 | 0.3% | 78.4% |
| Comparative Example 10 | Adsorbent A | 66.7% | 83.7% |
| Reference Example 10 | Adsorbent 155 | 0.6% | 79.7% |

Example 25 Evaluation of Cell Separation Capacity of Adsorbent—8

Example 25 is related to evaluation of the cell separation capacity of adsorbent 127, using cell mixtures of 201B7 cells, 253G1 cells, or 1231A3 cells, which are human iPS cell lines having a sugar chain containing a structure composed of "Fucα1-2Galβ1-3GlcNAc and/or Fucα1-2Galβ1-3GalNAc" (which cell lines were distributed from CiRA, Kyoto University after concluding a patent licensing agreement and an MTA agreement), and NHDF cells, which have no sugar chain containing a structure composed of "Fucα1-2Galβ1-3GlcNAc and/or Fucα1-2Galβ1-3GalNAc".

(1) Production of Adsorbent 127, and Preparation of Column Packed with Adsorbent 127

Adsorbent 127 was produced according to the method described in Example 15. As a result of calculation of the amount of the fucose-binding protein 127 immobilized per 1 mL of the adsorbent 127, the immobilized amount was found to be 1000 μg/mL-adsorbent. Subsequently, according to the method described in (1) of Example 18, a column packed with the adsorbent 127 produced was prepared (adsorbent volume: 500 μL).

(2) Preparation of Cell Mixtures for Evaluation

Cell suspensions of 201B7 cells, 253G1 cells, and 1231A3 cells stained with Cell Tracker Orange, prepared according to the method in (2) of Example 22 were used. In addition, a cell suspension of NHDF cells stained with Cell Tracker Green, prepared in (2) of Example 23 was used.

The number of cells in each of the cell suspensions of 201B7 cells, 253G1 cells, 1231A3 cells, and NHDF cells was measured, and each of the cell suspensions of 201B7 cells, 253G1 cells, and 1231A3 cells was mixed with the cell suspension of NHDF cells such that the ratio between the 201B7 cells and the NHDF cells was 49:51, such that the ratio between the 253G1 cells and the NHDF cells was 53:47, and such that the ratio between the 1231A3 cells and the NHDF cells was 69:31 in terms of the cell number, to prepare cell mixtures for evaluation of the cell separation capacity.

(3) Evaluation of Cell Separation Capacity Using Column Packed with Adsorbent

The column packed with each adsorbent was placed in an upright position, and the cell mixture of the cell suspensions of 201B7 cells and NHDF cells prepared by the above method was applied to the column in an amount of $3.3\times 10^6$ cells/mL-adsorbent, that is, such that the amounts of the 201B7 cells and the NHDF cells were $1.6\times10^6$ cells/mL-adsorbent and $1.7\times10^6$ cells/mL-adsorbent, respectively. The cell mixture of the cell suspensions of 253G1 cells and NHDF cells prepared by the above method was applied to the column in an amount of $3.6\times10^6$ cells/mL-adsorbent, that is, such that the amounts of the 253G1 cells and the NHDF cells were $1.9\times10^6$ cells/mL-adsorbent and $1.7\times10^6$ cells/mL-adsorbent, respectively. The cell mixture of the cell suspensions of 1231A3 cells and NHDF cells prepared by the above method was applied to the column in an amount of $5.5\times10^6$ cells/mL-adsorbent, that is, such that the amounts of the 1231A3 cells and the NHDF cells were $3.8\times10^6$ cells/mL-adsorbent and $1.7\times10^6$ cells/mL-adsorbent, respectively.

Thereafter, by the method described in (3) of Example 21, each effluent cell suspension was collected from the adsorbent 127, and the number of each type of cells contained in the effluent cell suspension collected was calculated. Thereafter, the effluent rates of the 201B7 cells and the NHDF cells, the effluent rates of the 253G1 cells and the NHDF cells, or the effluent rates of the 1231A3 cells and the NHDF cells in each effluent cell suspension were calculated.

Table 21 shows the effluent rates of the 201B7 cells and the NHDF cells, the effluent rates of the 253G1 cells and the NHDF cells, and the effluent rates of the 1231A3 cells and the NHDF cells for the adsorbent 127. While the effluent rate of the 201B7 cells was 1.8%, the effluent rate of the NHDF cells was 76.2%. While the effluent rate of the 253G1 cells was 3.4%, the effluent rate of the NHDF cells was 94.0%. While the effluent rate of the 1231A3 cells was 2.7%, the effluent rate of the NHDF cells was 78.1%. Thus, it became clear that adsorbent 127, prepared by immobilizing the fucose-binding protein 127 of the present invention on the insoluble carrier, is capable of selectively separating 201B7 cells, 253G1 cells, or 1231A3 cells alone from a mixture of 201B7 cells and NHDF cells, a mixture of 253G1 cells and NHDF cells, or a mixture of 1231A3 cells and NHDF cells, respectively.

Comparative Example 11 Evaluation of Cell Separation Capacity of Adsorbent Having No Fucose-Binding Protein Immobilized Thereon—8

Comparative Example 11 is related to evaluation of the cell separation capacity of adsorbent A, which has no fucose-binding protein immobilized thereon, using a cell mixture of 201B7 cells and NHDF cells, a cell mixture of 253G1 cells and NHDF cells, or a cell mixture of 1231A3 cells and NHDF cells.

By the method described in (1) of Example 18, adsorbent A was packed into a column (adsorbent volume: 500 μL). Subsequently, using the cell mixture of 201B7 cells and NHDF cells, the cell mixture of 253G1 cells and NHDF cells, or the cell mixture of 1231A3 cells and NHDF cells prepared in (2) of Example 25, application of the cell mixture to the column packed with the adsorbent, collection of the effluent cell suspension, and measurement of the fluorescence intensity of the effluent cell suspension were sequentially carried out by the method described in (3) of Example 25. As a result of calculation of the effluent rates of the 201B7 cells and the NHDF cells, the effluent rates of the 253G1 cells and the NHDF cells, or the effluent rates of the 1231A3 cells and the NHDF cells for adsorbent A, the effluent rate of the 201B7 cells was found to be 97.8%, and the effluent rate of the NHDF cells was found to be 83.7%; the effluent rate of the 253G1 cells was found to be 104.0%, and the effluent rate of the NHDF cells was found to be 72.6%; or the effluent rate of the 1231A3 cells was found to be 91.3%, and the effluent rate of the NHDF cells was found to be 86.3% (Table 21), respectively. Thus, it became clear that adsorbent A, which has no fucose-binding protein immobilized thereon, is not capable of separating 201B7 cells, 253G1 cells, or 1231A3 cells by adsorption from a mixture of 201B7 cells and NHDF cells, a mixture of 253G1 cells and NHDF cells, or a mixture of 1231A3 cells and NHDF cells, respectively.

[Table 21]

TABLE 21

| Example/ Comparative Example | Adsorbent | 201B7 cell effluent rate | 253G1 cell effluent rate | 1123A3 cell effluent rate | NHDF cell effluent rate |
|---|---|---|---|---|---|
| Example 25 | Adsorbent 127 | 1.8% | — | — | 76.2% |
| | | — | 3.4% | — | 94.0% |
| | | — | — | 2.7% | 78.1% |
| Comparative Example 11 | Adsorbent A | 97.8% | — | — | 83.7% |
| | | — | 104.0% | — | 72.6% |
| | | — | — | 91.3% | 86.3% |

Example 26 Production of Adsorbent 127C72G by Immobilization of Fucose-Binding Protein 127C72G on Insoluble Carrier Example 26 is related to production of an adsorbent (hereinafter referred to as adsorbent 127C72G) by immobilization of the fucose-binding protein 127C72G produced in Example 12 on an insoluble carrier.

The desired adsorbent 127C72G was produced by the same method as described in Example 14 except that the fucose-binding protein 127C72G produced in Example 12 was used instead of the purified 129 solution (solution of fucose-binding protein 129 in D-PBS(−)) produced in Example 1.

According to the method described in (3) of Example 14, the amount of the fucose-binding protein 127C72G immobilized per 1 mL of the adsorbent 127C72G was calculated. As a result, the immobilized amount was found to be 294 μg/mL-adsorbent. The adsorbent 127C72G in the water-wet state had an average particle size of 180 μm and a particle size range of 150 to 250 μm.

Example 27 Evaluation of Cell Adsorption Capacity of Adsorbent—9

Example 27 is related to evaluation of the adsorption capacity of adsorbent 127C72G for 201B7 cells.

(1) Preparation of Column Packed with Adsorbent

Using the adsorbent 127C72G produced in Example 26, a column packed with the adsorbent 127C72G produced was prepared according to the method described in (1) of Example 18 (adsorbent volume: 500 μL). Subsequently, a cell suspension of 201B7 cells prepared by the method described in (2) of Example 22 was applied to the column prepared, in an amount of 5.6× $10^6$ cells/mL-adsorbent. Thereafter, application of the cell suspension to the column packed with the adsorbent, collection of the effluent cell suspension, and measurement of the fluorescence intensity of the effluent cell suspension were sequentially carried out by the method described in (3) of Example 22. As a result of calculation of the effluent rate of the 201B7 cells for adsorbent 127C72G, the effluent rate was found to be 4.0%. Thus, it became clear that adsorbent 127C72G, which was prepared by immobilizing the fucose-binding protein 127C72G of the present invention on the insoluble carrier, has a high iPS-cell adsorption capacity.

Example 28 Production and Functional Evaluation of Fucose-Binding Protein 127Q39x Example 28 is related to preparation of a fucose-binding protein by adding an oligopeptide containing a polyhistidine sequence to the N-terminus, and adding an oligopeptide containing a cysteine residue to the C-terminus, of an amino acid sequence which is the same as SEQ ID NO: 3 except that the glutamine residue identified as the glutamine residue at position 39 thereof is substituted with an amino acid residue x which is not a glutamine residue, that is, preparation of a fucose-binding protein (hereinafter referred to as fucose-binding protein 127Q39x) which is the same as the fucose-binding protein 127 of SEQ ID NO: 34 except that the glutamine residue at position 53 thereof is substituted with an amino acid residue x which is not a glutamine residue, and evaluation of the thermal stability thereof and the binding affinity thereof to a sugar chain.

(1) Preparation of Expression Vector pET-BC2LCN (127Q39x)cys and Recombinant *E. coli* BL21 (DE3)/pET-BC2LCN(127Q39x)cys The expression vector pET-BC2LCN(127Q39x)cys is an expression vector for expression of the fucose-binding protein 127Q39x, and the recombinant *E. coli* BL21 (DE3)/pET-BC2LCN(127Q39x)cys is a transformant for production of the fucose-binding protein 127Q39x. Here, x represents the 19 kinds of amino acid residues other than a glutamine residue. The following is one example of preparation of the expression vector and the transformant, and illustrates a method of preparing the expression vector pET-BC2LCN(127Q39L)cys and the recombinant *E. coli* BL21 (DE3)/pET-BC2LCN(127Q39L)cys for production of the fucose-binding protein 127Q39L (SEQ ID NO: 44) by adding an oligopeptide containing a polyhistidine sequence to the N-terminus, and adding an oligopeptide sequence containing a cysteine residue to the C-terminus, of the amino acid sequence of the fucose-binding protein of SEQ ID NO: 13 (amino acid sequence which is the same as SEQ ID NO: 3 except that the glutamine residue at position 39 is substituted with a leucine residue). In the amino acid sequence of SEQ ID NO: 44, the sequence from position 5 to position 10 corresponds to the oligopeptide containing a polyhistidine sequence; the sequence from position 15 to position 141 corresponds to the amino acid sequence of SEQ ID NO: 13; and the sequence from position 142 to position 148 corresponds to the oligopeptide sequence containing a cysteine residue.

A nucleotide sequence encoding the fucose-binding protein 127Q39L (nucleotide sequence having XbaI and XhoI restriction sites, shown in SEQ ID NO: 63; GenScript) was synthesized, and digested with the restriction enzymes XbaI and XhoI, followed by performing ligation reaction with the expression vector pET28a(+) (manufactured by Merck Millipore) treated with the restriction enzymes XbaI and XhoI. In the nucleotide sequence of SEQ ID NO: 63, the sequence from position 54 to position 71 corresponds to a polynucleotide encoding the oligopeptide containing a polyhistidine sequence; the sequence from position 84 to position 464 corresponds to a polynucleotide encoding the polypeptide corresponding to the amino acid sequence of SEQ ID NO: 13; and the sequence from position 465 to position 485 corresponds to a polynucleotide encoding the oligopeptide containing a cysteine residue. Subsequently, *E. coli* BL21 (DE3) was transformed using the ligation product, to obtain the recombinant *E. coli* BL21 (DE3)/pET-BC2LCN (127Q39L)cys. By the method disclosed in JP 2018-000038 A, the recombinant *E. coli* BL21 (DE3)/pET-BC2LCN (127Q39L)cys obtained was cultured, and then the expression vector pET-BC2LCN(127Q39L)cys was obtained by extraction from the bacterial cells obtained. As a result of confirmation of the nucleotide sequence by sequence analysis, it was confirmed that the expression vector pET-BC2LCN(127Q39L)cys contains the nucleotide sequence of SEQ ID NO: 28, which encodes the amino acid sequence of SEQ ID NO: 13. By the same method, expression vectors pET-BC2LCN(127Q39x)cys for expression of the 19 kinds of recombinant proteins shown in Table 22 (fucose-binding proteins 127Q39x), and transformants having these were prepared.

[Table 22]

TABLE 22

| Recombinant protein | Amino acid substitution* |
|---|---|
| Fucose-binding protein 127Q39L | Leucine residue |
| Fucose-binding protein 127Q39M | Methionine residue |
| Fucose-binding protein 127Q39C | Cysteine residue |
| Fucose-binding protein 127Q39G | Glycine residue |
| Fucose-binding protein 127Q39A | Alanine residue |
| Fucose-binding protein 127Q39W | Tryptophan residue |
| Fucose-binding protein 127Q39K | Lysine residue |
| Fucose-binding protein 127Q39H | Histidine residue |
| Fucose-binding protein 127Q39R | Arginine residue |
| Fucose-binding protein 127Q39E | Glutamic acid residue |
| Fucose-binding protein 127Q39S | Serine residue |
| Fucose-binding protein 127Q39T | Threonine residue |
| Fucose-binding protein 127Q39N | Asparagine residue |
| Fucose-binding protein 127Q39Y | Tyrosine residue |
| Fucose-binding protein 127Q39V | Valine residue |
| Fucose-binding protein 127Q39I | Isoleucine residue |
| Fucose-binding protein 127Q39F | Phenylalanine residue |
| Fucose-binding protein 127Q39D | Aspartic acid residue |
| Fucose-binding protein 127Q39P | Proline residue |

*Amino acid substitution of the glutamine residue at position 53 in the fucose-binding protein 127 (SEQ ID NO: 34)

(2) Production of Fucose-Binding Protein 127Q39x

Using the transformants prepared in (1), production of recombinant proteins, collection of soluble protein extracts, and purification of fucose-binding proteins from the soluble protein extracts by nickel chelate affinity chromatography were carried out by the method described in Comparative Example 1, to produce the 19 kinds of recombinant proteins (fucose-binding proteins 127Q39x) described in Table 22.

(3) Evaluation of Thermal Stabilities of Recombinant Proteins

In order to investigate the thermal stabilities of the recombinant proteins produced in (2), the sugar-chain binding affinity of each recombinant protein after heat treatment was evaluated by the same method as described in (3) of Reference Example 2 except that the heat treatment temperature was 81° C.

Table 23 shows the result of evaluation of the sugar-chain binding affinity of each recombinant protein after the heat treatment at 81° C. for 30 minutes. In Table 23, the sugar-chain binding capacity of each recombinant protein is expressed as a relative value with respect to the sugar-chain binding affinity after treatment at room temperature, which is taken as 100%. The evaluation of the sugar-chain binding affinity after treatment at room temperature was carried out also by the same method as described in (3) of Reference Example 2. In Table 23, the sugar-chain binding capacities of the fucose-binding protein 127Q39D and the fucose-binding protein 127Q39P are expressed as "-" since their sugar-chain binding capacities were lost after the treatment at room temperature. As shown in Table 23, the following recombinant proteins retained sugar-chain binding capacity even after the heat treatment at 81° C. for 30 minutes: the fucose-binding protein 127Q39L and the fucose-binding protein 127Q39M (SEQ ID NO: 45; amino acid sequence prepared by adding an oligopeptide containing a polyhisti-dine sequence to the N-terminus, and adding an oligopeptide sequence containing a cysteine residue to the C-terminus, of the amino acid sequence of the fucose-binding protein of SEQ ID NO: 14).

[Table 23]

TABLE 23

| Recombinant protein | Amino acid substitution*[1] | Sugar-chain binding capacity (%)*[2] |
| --- | --- | --- |
| Fucose-binding protein 127Q39L | Leucine residue | 56.3 |
| Fucose-binding protein 127Q39M | Methionine residue | 20.5 |
| Fucose-binding protein 127Q39C | Cysteine residue | 0.3 |
| Fucose-binding protein 127Q39G | Glycine residue | 0.0 |
| Fucose-binding protein 127Q39A | Alanine residue | 0.0 |
| Fucose-binding protein 127Q39W | Tryptophan residue | 0.0 |
| Fucose-binding protein 127Q39K | Lysine residue | 0.0 |
| Fucose-binding protein 127Q39H | Histidine residue | 0.0 |
| Fucose-binding protein 127Q39R | Arginine residue | 0.0 |
| Fucose-binding protein 127Q39E | Glutamic acid residue | 0.0 |
| Fucose-binding protein 127Q39S | Serine residue | 0.0 |
| Fucose-binding protein 127Q39T | Threonine residue | 0.0 |
| Fucose-binding protein 127Q39N | Asparagine residue | 0.0 |
| Fucose-binding protein 127Q39Y | Tyrosine residue | 0.0 |
| Fucose-binding protein 127Q39V | Valine residue | 0.0 |
| Fucose-binding protein 127Q39I | Isoleucine residue | 0.0 |
| Fucose-binding protein 127Q39F | Phenylalanine residue | 0.0 |
| Fucose-binding protein 127 | None | 0.0 |
| Fucose-binding protein 127Q39F | Phenylalanine residue | —*[3] |
| Fucose-binding protein 127Q39F | Phenylalanine residue | —*[3] |

*[1]Amino acid substitution of the glutamine residue at position 53 in the fucose-binding protein 127 (SEQ ID NO: 34)
*[2]Relative value with respect to the sugar-chain binding capacity after treatment at room temperature, which is taken as 100%
*[3]Sugar-chain binding capacity was lost after treatment at room temperature (4) Measurement of Denaturation Midpoint Temperature The fucose-binding protein 127Q39L, which exhibited sugar-chain binding capacity even after the heat treatment at 81° C. for 30 minutes in (3), was subjected to measurement of the denaturation midpoint temperature by the method described in (2) of Example 12. As a result, the denaturation midpoint temperature of the fucose-binding protein 127Q39L was found to be 90.2±0.5° C.

(5) Evaluation of Binding Affinity to Sugar Chain

As a result of evaluation of the binding affinity of the fucose-binding protein 127Q39L to H type 3 sugar chain by the method described in (2) of Example 7, the dissociation constant was found to be 1.1 nM.

Example 29 Production and Functional Evaluation of Fucose-Binding Protein 127Q39x/C72z and Fucose-Binding Protein 127Q39x/Q65y/C72z Example 29 is related to production of a fucose-binding protein by adding an oligopeptide containing a polyhistidine sequence to the N-terminus, and adding an oligopeptide containing a cysteine residue to the C-terminus, of an amino acid sequence which is the same as SEQ ID NO: 3 except that the glutamine residue at position 39 and the cysteine residue at position 72 are substituted with other amino acid residues (hereinafter referred to as fucose-binding protein 127Q39x/C72z), and a fucose-binding protein by adding an oligopeptide containing a polyhistidine sequence to the N-terminus, and adding an oligopeptide containing a cysteine residue to the C-terminus, of an amino acid sequence which is the same as SEQ ID NO: 3 except that the glutamine residue at position 39, the glutamine residue at position 65, and the cysteine residue at position 72 are substituted with other amino acid residues (hereinafter referred to as fucose-binding protein 127Q39x/Q65y/C72z), and evaluation of the thermal stabilities thereof and the binding affinities thereof to sugar chains. More specifically, the fucose-binding protein 127Q39x/C72z is a fucose-binding protein which is the same as the fucose-binding protein 127 of SEQ ID NO: 34 except that the glutamine residue at position 53 is substituted with an amino acid residue x which is not a glutamine residue, and that the cysteine residue identified as the cysteine residue at position 86 is substituted with an amino acid residue z which is not a cysteine residue. The fucose-binding protein 127Q39x/Q65y/C72z is a fucose-binding protein which is the same as the fucose-binding protein 127 of SEQ ID NO: 34 except that the glutamine residue at position 53 is substituted with an amino acid residue x which is not a glutamine residue, that the glutamine residue identified as the glutamine residue at position 79 is substituted with an amino acid residue y which is not a glutamine residue, and that the cysteine residue identified as the cysteine residue at position 86 is substituted with an amino acid residue z which is not a cysteine residue.

(1) Preparation of Expression Vector pET-BC2LCN (127Q39x/C72z)cys and Recombinant E. coli BL21 (DE3)/pET-BC2LCN(127Q39x/C72z)cys The expression vector pET-BC2LCN(127Q39x/C72z)cys is an expression vector for expression of the fucose-binding protein 127Q39x/C72z, and the recombinant E. coli BL21 (DE3)/pET-BC2LCN(127Q39x/C72z)cys is a transformant for production of the fucose-binding protein 127Q39x/Q65y/C72z. Here, x represents the 19 kinds of amino acid residues other than a glutamine residue, and z represents the 19 kinds of amino acid residues other than a cysteine residue. The following is one example of preparation of the expression vector and the transformant, and illustrates a method of preparing the expression vector pET-BC2LCN (127Q39L/C72G)cys and the recombinant E. coli BL21 (DE3)/pET-BC2LCN(127Q39L/C72G)cys for production of the fucose-binding protein 127Q39L/C72G (SEQ ID NO: 46) by adding an oligopeptide containing a polyhistidine sequence to the N-terminus, and adding an oligopeptide sequence containing a cysteine residue to the C-terminus, of the amino acid sequence of the fucose-binding protein of SEQ ID NO: 15 (amino acid sequence which is the same as the amino acid sequence of SEQ ID NO: 3 except that the glutamine residue at position 39 is substituted with a leucine residue, and that the cysteine residue at position 72 is substituted with a glycine residue). In the amino acid sequence of SEQ ID NO: 46, the sequence from position 5 to position 10 corresponds to the oligopeptide containing a polyhistidine sequence; the sequence from position 15 to position 141 corresponds to the amino acid sequence of SEQ ID NO: 15; and the sequence from position 142 to position 148 corresponds to the oligopeptide sequence containing a cysteine residue. In the amino acid sequence of SEQ ID NO: 47, the sequence from position 5 to position 10 corresponds to the oligopeptide containing a polyhistidine sequence; the sequence from position 15 to position 141 corresponds to the amino acid sequence of SEQ ID NO: 16; and the sequence from position 142 to position 148 corresponds to the oligopeptide sequence containing a cysteine residue.

A nucleotide sequence encoding the fucose-binding protein 127Q39L/C72G (nucleotide sequence having XbaI and XhoI restriction sites, shown in SEQ ID NO: 64; GenScript) was synthesized, and digested with the restriction enzymes XbaI and XhoI, followed by performing ligation reaction with the expression vector pET28a (+) (manufactured by Merck Millipore) treated with the restriction enzymes XbaI and XhoI. In the nucleotide sequence of SEQ ID NO: 64, the sequence from position 54 to position 71 corresponds to a polynucleotide encoding the oligopeptide containing a polyhistidine sequence; the sequence from position 84 to position 464 corresponds to a polynucleotide encoding the polypeptide corresponding to the amino acid sequence of SEQ ID NO: 15; and the sequence from position 465 to position 485 corresponds to a polynucleotide encoding the oligopeptide containing a cysteine residue. Subsequently, by the method described in Example 28, the recombinant *E. coli* BL21 (DE3)/pET-BC2LCN(127Q39L/C72G)cys and the expression vector pET-BC2LCN(127Q39L/C72G)cys were obtained. As a result of confirmation of the nucleotide sequence by sequence analysis, it was confirmed that the expression vector pET-BC2LCN(127Q39L/C72G)cys contains the nucleotide sequence of SEQ ID NO: 30, which encodes the amino acid sequence of SEQ ID NO: 15.

(2) Preparation of Expression Vector pET-BC2LCN (127Q39x/Q65y/C72z)cys and Recombinant *E. coli* BL21 (DE3)/pET-BC2LCN(127Q39x/Q65y/C72z)cys The expression vector pET-BC2LCN(127Q39x/Q65y/C72z)cys is an expression vector for expression of the fucose-binding protein 127Q39x/Q65y/C72z, and the recombinant *E. coli* BL21 (DE3)/pET-BC2LCN(127Q39x/Q65y/C72z)cys is a transformant for production of the fucose-binding protein 127Q39x/Q65y/C72z. Here, x and y each represent the 19 kinds of amino acid residues other than a glutamine residue, and z represents the 19 kinds of amino acid residues other than a cysteine residue. The following is one example of preparation of the expression vector and the transformant, and illustrates a method of preparing the expression vector pET-BC2LCN(127Q39L/Q65L/C72G) cys and the recombinant *E. coli* BL21 (DE3)/pET-BC2LCN (127Q39L/Q65L/C72G)cys for production of the fucose-binding protein 127Q39L/Q65L/C72G (SEQ ID NO: 47) by adding an oligopeptide containing a polyhistidine sequence to the N-terminus, and adding an oligopeptide sequence containing a cysteine residue to the C-terminus, of the amino acid sequence of the fucose-binding protein of SEQ ID NO: 16 (amino acid sequence which is the same as the amino acid sequence of SEQ ID NO: 3 except that the glutamine residue at position 39 is substituted with a leucine residue, that the glutamine residue at position 65 is substituted with a leucine residue, and that the cysteine residue at position 72 is substituted with a glycine residue). In the amino acid sequence of SEQ ID NO: 47, the sequence from position 5 to position 10 corresponds to the oligopeptide containing a polyhistidine sequence; the sequence from position 15 to position 141 corresponds to the amino acid sequence of SEQ ID NO: 16; and the sequence from position 142 to position 148 corresponds to the oligopeptide sequence containing a cysteine residue.

A nucleotide sequence encoding the fucose-binding protein 127Q39L/Q65L/C72G (nucleotide sequence having XbaI and XhoI restriction sites, shown in SEQ ID NO: 65; GenScript) was synthesized, and digested with the restriction enzymes XbaI and XhoI, followed by performing ligation reaction with the expression vector pET28a (+) (manufactured by Merck Millipore) treated with the restriction enzymes XbaI and XhoI. In the nucleotide sequence of SEQ ID NO: 65, the sequence from position 54 to position 71 corresponds to a polynucleotide encoding the oligopeptide containing a polyhistidine sequence; the sequence from position 84 to position 464 corresponds to a polynucleotide encoding the polypeptide corresponding to the amino acid sequence of SEQ ID NO: 16; and the sequence from position 465 to position 485 corresponds to a polynucleotide encoding the oligopeptide containing a cysteine residue. Subsequently, by the method described in Example 28, the recombinant *E. coli* BL21 (DE3)/pET-BC2LCN(127Q39L/Q65L/C72G)cys and the expression vector pET-BC2LCN (127Q39L/Q65L/C72G)cys were obtained. As a result of confirmation of the nucleotide sequence by sequence analysis, it was confirmed that the expression vector pET-BC2LCN(127Q39L/Q65L/C72G)cys contains the nucleotide sequence of SEQ ID NO: 31, which encodes the amino acid sequence of SBQ ID NO: 16.

By the same methods as in (1) and (2) of Example 29, the expression vector PET-BC2LCN(127Q39x/C72z or 127Q39x/Q65y/C72z)cys for expression of the eight kinds of recombinant proteins shown in Table 24 (the fucose-binding protein 127Q39x/C72z or the fucose-binding protein 127Q39x/Q65y/C72z), and transformants having these were prepared.

[Table 24]

TABLE 24

| Recombinant protein | Amino acid substitution | | |
| | Position 39[*1] | Position 65[*1] | Position 72[*1] |
|---|---|---|---|
| Fucose-binding protein 127Q39L/C72G | Leucine residue | None | Glycine residue |
| Fucose-binding protein 127Q39K/C72G | Lysine residue | None | Glycine residue |
| Fucose-binding protein 127Q39R/C72G | Arginine residue | None | Glycine residue |
| Fucose-binding protein 127Q39E/C72G | Glutamic acid residue | None | Glycine residue |
| Fucose-binding protein 127Q39V/C72G | Valine residue | None | Glycine residue |
| Fucose-binding protein 127Q39L/Q65L | Leucine residue | Leucine residue | None |
| Fucose-binding protein 127Q65L/C72G | None | Leucine residue | Glycine residue |
| Fucose-binding protein 127Q39L/Q65L/C72G | Leucine residue | Leucine residue | Glycine residue |

[*1]Amino acid substitution of the glutamine residue at position 53 in the fucose-binding protein 127 (SEQ ID NO: 34)
[*2]Amino acid substitution of the glutamine residue at position 79 in the fucose-binding protein 127 (SEQ ID NO: 34)
[*3]Amino acid substitution of the glutamine residue at position 86 in the fucose-binding protein 127 (SEQ ID NO: 34)

(3) Production of Fucose-Binding Protein 127Q39x/Q65y/C72z

Using the transformants prepared in (1), production of recombinant proteins, collection of soluble protein extracts, and purification of fucose-binding proteins from the soluble protein extracts by nickel chelate affinity chromatography were carried out by the method described in Comparative Example 1, to produce the eight kinds of recombinant proteins described in Table 24 (the fucose-binding protein 127Q39x/Q65y/C72z).

(4) Evaluation of Thermal Stabilities of Recombinant Proteins

In order to investigate the thermal stabilities of the recombinant proteins produced in (2), the sugar-chain binding affinity of each recombinant protein after heat treatment was evaluated by the same method as described in (3) of Reference Example 2 except that the heat treatment temperature was 84° C. or 88° C.

Table 25 shows the result of evaluation of the sugar-chain binding capacity of each recombinant protein after the heat treatment at 84° C. or 88° C. for 30 minutes. In Table 25, the sugar-chain binding capacity of each recombinant protein is expressed as a relative value with respect to the sugar-chain binding capacity after treatment at room temperature, which is taken as 100%. The evaluation of the sugar-chain binding affinity after treatment at room temperature was carried out also by the same method as described in (3) of Reference Example 2. As shown in Table 25, the following recombinant proteins retained sugar-chain binding capacity even after the heat treatment at 84° C. or 88° C. for 30 minutes: the fucose-binding protein 127Q39L/C72G and the fucose-binding protein 127Q39L/Q65L/C72G.

[Table 25]

TABLE 25

| Recombinant protein | Sugar-chain binding capacity (%)* | |
| | After treatment at 84° C. | After treatment at 88° C. |
| --- | --- | --- |
| Fucose-binding protein 127Q39L/C72G | 79.0 | 16.0 |
| Fucose-binding protein 127Q39K/C72G | 0.0 | Not measured |
| Fucose-binding protein 127Q39R/C72G | 0.0 | Not measured |
| Fucose-binding protein 127Q39E/C72G | 0.0 | Not measured |
| Fucose-binding protein 127Q39V/C72G | 0.0 | Not measured |
| Fucose-binding protein 127Q39L/Q65L | 0.0 | Not measured |
| Fucose-binding protein 127Q65L/C72G | 0.0 | Not measured |
| Fucose-binding protein 127Q39L/Q65L/C72G | 83.0 | 24.0 |
| Fucose-binding protein 127Q39L | 8.0 | 0.0 |
| Fucose-binding protein 127C72G | 0.0 | Not measured |
| Fucose-binding protein 127 | 0.0 | Not measured |

(5) Measurement of Denaturation Midpoint Temperatures

The fucose-binding protein 127Q39L/C72G and the fucose-binding protein 127Q39L/Q65L/C72G, which exhibited sugar-chain binding capacity even after the best treatment at 88° C. for 30 minutes in (3), were subjected to measurement of the denaturation midpoint temperature by the method described in (2) of Example 12. As a result, the denaturation midpoint temperature of the fucose-binding protein 127Q39L/C72G was found to be 94.4±0.5° C., and the denaturation midpoint temperature of the fucose-binding protein 127Q39L/Q65L/C72G was found to be 95.6±0.5° C.

Table 26 shows the denaturation midpoint temperatures of the fucose-binding protein 127C72G (Example 12), fucose-binding protein 127C72A (Example 13), fucose-binding protein 127Q39L (Example 28), fucose-binding protein 127Q39L/C72G (Example 29), fucose-binding protein 127Q39L/Q65L/C72G (Example 29), and recombinant BC2LCN(155)cys (Comparative Example 3).

[Table 26]

TABLE 26

| Example/Comparative Example | Recombinant protein | Denaturation midpoint temperature (° C.) |
| --- | --- | --- |
| Example 12 | Fucose-binding protein 127C72G | 88.3 ± 0.5 |
| Example 13 | Fucose-binding protein 127C72A | 83.4 ± 0.5 |
| Example 28 | Fucose-binding protein 127Q39L | 90.2 ± 0.5 |
| Example 29 | Fucose-binding protein 127Q39L/C72G | 94.4 ± 0.5 |
| Example 29 | Fucose-binding protein 127Q39L/Q65L/C72G | 95.6 ± 0.5 |
| Comparative Example 3 | Recombinant BC2LCN(155)cys | 82.3 ± 0.5 |

(6) Evaluation of Binding Affinities to Sugar Chains

As a result of evaluation of the binding affinity of the fucose-binding protein 127Q39L/C72G to H type 3 sugar chain by the method described in (2) of Example 7, the dissociation constant for H type 3 sugar chain was found to be 3.9 nM. As a result of evaluation of the binding affinities of the fucose-binding protein 127Q39L/Q65L/C72G to H type 1 sugar chain and H type 3 sugar chain, the dissociation constant for H type 1 sugar chain was found to be 3.9 nM, and the dissociation constant for H type 3 sugar chain was found to be 4.6 nM.

Table 27 shows the dissociation constants of the fucose-binding protein 127C72G (Example 12), fucose-binding protein 127C72A (Example 13), fucose-binding protein 127Q39L (Example 28), fucose-binding protein 127Q39L/C72G (Example 29), fucose-binding protein 127Q39L/Q65L/C72G (Example 29), and recombinant BC2LCN(155)cys (Comparative Example 2), for H type 1 sugar chain and H type 3 sugar chain.

[Table 27]

TABLE 27

| Example/Comparative Example | Recombinant protein | Dissociation constant (nM) | |
| | | H type 1 sugar chain | H type 3 sugar chain |
| --- | --- | --- | --- |
| Example 12 | Fucose-binding protein 127C72G | 1.2 | 1.1 |
| Example 13 | Fucose-binding protein 127C72A | 0.7 | 2.0 |
| Example 28 | Fucose-binding protein 127Q39L | Not measured | 1.1 |
| Example 29 | Fucose-binding protein 127Q39L/C72G | Not measured | 3.9 |
| Example 29 | Fucose-binding protein 127Q39L/Q65L/C72G | 3.9 | 4.6 |
| Comparative Example 2 | Recombinant BC2LCN(155)cys | 3.9 | 11 |

Example 30 Production of Fucose-Binding Protein 127Q39L and Evaluation of Productivity Example 30 is related to production of the fucose-binding protein 127Q39L (SEQ ID NO: 44; fucose-binding protein prepared by adding an oligopeptide containing a polyhistidine sequence to the N-terminus, and adding an oligopeptide sequence containing cysteine to the C-terminus, of the amino acid sequence of the fucose-binding protein of SEQ ID NO: 13), and evaluation of the productivity thereof. Production of the fucose-binding protein 127Q39L using the recombinant *E. coli* BL21 (DE3)/pET-BC2LCN(127Q39L) cys described in Example 28, collection of the soluble protein extract, and purification of the fucose-binding protein 127Q39L from the soluble protein extract by nickel chelate affinity chromatography were carried out by the methods described in (2) of Comparative Example 1 and (3) of Comparative Example 1, to produce the desired fucose-binding protein 127Q39L. The productivity of the fucose-binding protein 127Q39L per 1-L culture broth was calculated according to the method described in (4) of Comparative Example 1. As a result, the productivity was found to be 450 mg/L-culture broth. The solution containing the fucose-binding protein 127Q39L produced was dialyzed against D-PBS(−), and then its concentration was adjusted to an appropriate concentration using D-PBS(−). The solution was then used in the later-described production of an adsorbent.

Example 31 Production of Adsorbent 127Q39L by Immobilization of Fucose-Binding Protein 127Q39L on Insoluble Carrier Example 31 is related to production of an adsorbent (hereinafter referred to as adsorbent 127Q39L) by immobilization of the fucose-binding protein 127Q39L produced in Example 30 on an insoluble carrier. The desired adsorbent 127Q39L was produced by the same method as described in Example 14 except that the fucose-binding protein 127Q39L produced in Example 30 was used instead of the purified 129 solution (solution of the fucose-binding protein 129 in D-PBS(−)) produced in Example 1. According to the method described in (3) of Example 14, the amount of the fucose-binding protein 127Q39LG immobilized per 1 mL of the adsorbent 127Q39L was calculated. As a result, the immobilized amount was found to be 316 μg/mL-adsorbent. The adsorbent 127Q39L in the water-wet state had an average particle size of 182 μm and a particle size range of 150 to 250 μm.

Example 32 Evaluation of Cell Adsorption Capacities of Adsorbents—10

Example 32 is related to evaluation of the adsorption capacity of adsorbent 127Q39L for 201B7 cells. Using the adsorbent 127Q39L produced in Example 31, a column packed with the adsorbent 127Q39L produced was prepared according to the method described in (1) of Example 18 (adsorbent volume: 500 μL). Subsequently, a cell suspension of 201B7 cells prepared by the method described in (2) of Example 22 was applied to the column prepared, in an amount of $3.3 \times 10^{6}$ cells/mL-adsorbent. Thereafter, application of the cell suspension to the column packed with the adsorbent, collection of the effluent cell suspension, and measurement of the fluorescence intensity of the effluent cell suspension were sequentially carried out by the method described in (3) of Example 22. As a result of calculation of the effluent rate of the 201B7 cells for adsorbent 127Q39L, the effluent rate was found to be 3.5%. Thus, it became clear that the adsorbent 127Q39L/Q65L/C72G, which was prepared by immobilizing the fucose-binding protein 127Q39L of the present invention on the insoluble carrier, has a high iPS-cell adsorption capacity.

Example 33 Production of Fucose-Binding Protein 127Q39L/C72G and Evaluation of Productivity Example 33 is related to production of the fucose-binding protein 127Q39L/C72G (SEQ ID NO: 46; fucose-binding protein prepared by adding an oligopeptide containing a polyhistidine sequence to the N-terminus, and adding an oligopeptide sequence containing cysteine to the C-terminus, of the amino acid sequence of the fucose-binding protein of SEQ ID NO: 15), and evaluation of the productivity thereof. Production of the fucose-binding protein 127Q39L/C72G using the recombinant *E. coli* BL21 (DE3)/pET-BC2LCN(127Q39L/C72G)cys described in Example 29, collection of the soluble protein extract, and purification of the fucose-binding protein 127Q39L/C72G from the soluble protein extract by nickel chelate affinity chromatography were carried out by the methods described in (2) of Comparative Example 1 and (3) of Comparative Example 1, to produce the desired fucose-binding protein 127Q39L/C72G. The productivity of the fucose-binding protein 127Q39L/C72G per 1-L culture broth was calculated according to the method described in (4) of Comparative Example 1. As a result, the productivity was found to be 480 mg/L-culture broth. The solution containing the fucose-binding protein 127Q39L/C72G produced was dialyzed against D-PBS(−), and then its concentration was adjusted to an appropriate concentration using D-PBS(−). The solution was then used in the later-described production of an adsorbent.

Example 34 Production of Adsorbent 127Q39L/C72G by Immobilization of Fucose-Binding Protein 127Q39L/C72G on Insoluble Carrier Example 34 is related to production of an adsorbent (hereinafter referred to as adsorbent 127Q39L/C72G) by immobilization of the fucose-binding protein 127Q39L/C72G produced in Example 33 on an insoluble carrier. The desired adsorbent 127Q39L/C72G was produced by the same method as described in Example 14 except that the fucose-binding protein 127Q39L/C72G produced in Example 33 was used instead of the purified 129 solution (solution of fucose-binding protein 129 in D-PBS(−)) produced in Example 1.

According to the method described in (3) of Example 14, the amount of the fucose-binding protein 127Q39L/C72G immobilized per 1 mL of the adsorbent 127Q39L/C72G was calculated. As a result, the immobilized amount was found to be 327 μg/mL-adsorbent. The adsorbent 127Q39L/Q65L/C72G in the water-wet state had an average particle size of 181 μm and a particle size range of 150 to 250 μm.

Example 35 Evaluation of Cell Adsorption Capacity of Adsorbent—11

Example 35 is related to evaluation of the adsorption capacity of the adsorbent 127Q39L/C72G for 201B7 cells. Using the adsorbent 127Q39L/C72G produced in Example 34, a column packed with the adsorbent 127Q39L/C72G produced was prepared according to the method described in (1) of Example 18 (adsorbent volume: 500 μL). Subsequently, a cell suspension of 201B7 cells prepared by the method described in (2) of Example 22 was applied to the column prepared, in an amount of 3.3× 10⁶ cells/mL-adsorbent. Thereafter, application of the cell suspension to the column packed with the adsorbent, collection of the effluent cell suspension, and measurement of the fluorescence intensity of the effluent cell suspension were sequentially carried out by the method described in (3) of Example 22. As a result of calculation of the effluent rate of the 201B7 cells for adsorbent 127Q39L/C72G, the effluent rate was found to be 2.3%. Thus, it became clear that adsorbent 127Q39L/C72G, which was prepared by immobilizing the fucose-binding protein 127Q39L/C72G of the present invention on the insoluble carrier, has a high iPS-cell adsorption capacity.

Example 36 Production of Fucose-Binding Protein 127Q39L/Q65L/C72G and Evaluation of Productivity Example 36 is related to production of the fucose-binding protein 127Q39L/Q65L/C72G (SEQ ID NO: 47; fucose-binding protein prepared by adding an oligopeptide containing a polyhistidine sequence to the N-terminus, and adding an oligopeptide sequence containing cysteine to the C-terminus, of the amino acid sequence of the fucose-binding protein of SEQ ID NO: 16), and evaluation of the productivity thereof.

Production of the fucose-binding protein 127Q39L/Q65L/C72G using the recombinant E. coli BL21 (DE3)/pET-BC2LCN(127Q39L/Q65L/C72G)cys described in Example 29, collection of the soluble protein extract, and purification of the fucose-binding protein 127Q39L/Q65L/C72G from the soluble protein extract by nickel chelate affinity chromatography were carried out by the methods described in (2) of Comparative Example 1 and (3) of Comparative Example 1, to produce the desired fucose-binding protein 127Q39L/Q65L/C72G. The productivity of the fucose-binding protein 127Q39L/Q65L/C72G per 1-L culture broth was calculated according to the method described in (4) of Comparative Example 1. As a result, the productivity was found to be 506 mg/L-culture broth. The solution containing the fucose-binding protein 127Q39L/Q65L/C72G produced was dialyzed against D-PBS(−), and then its concentration was adjusted to an appropriate concentration using D-PBS(−). The solution was then used in the later-described measurement of the denaturation midpoint temperature, evaluation of the sugar-chain binding affinity, and production of an adsorbent.

Example 37 Production of Adsorbent 127Q39L/Q65L/C72G by Immobilization of Fucose-Binding Protein 127Q39L/Q65L/C72G on Insoluble Carrier Example 37 is related to production of an adsorbent (hereinafter referred to as adsorbent 127Q39L/Q65L/C72G) by immobilization of the fucose-binding protein 127Q39L/Q65L/C72G produced in Example 36 on an insoluble carrier.

The desired adsorbent 127Q39L/Q65L/C72G was produced by the same method as described in Example 14 except that the fucose-binding protein 127Q39L/Q65L/C72G produced in Example 36 was used instead of the purified 129 solution (solution of fucose-binding protein 129 in D-PBS(−)) produced in Example 1.

According to the method described in (3) of Example 14, the amount of the fucose-binding protein 127Q39L/Q65L/C72G immobilized per 1 mL of the adsorbent 127Q39L/Q65L/C72G was calculated. As a result, the immobilized amount was found to be 273 μg/mL-adsorbent. The adsorbent 127Q39L/Q65L/C72G in the water-wet state had an average particle size of 180 μm and a particle size range of 150 to 250 μm.

Example 38 Evaluation of Cell Adsorption Capacity of Adsorbent—12

Example 38 is related to evaluation of the adsorption capacity of the adsorbent 127Q39L/Q65L/C72G for 201B7 cells.

(1) Preparation of Column Packed with Adsorbent

Using the adsorbent 127Q39L/Q65L/C72G produced in Example 37, a column packed with the adsorbent 127Q39L/Q65L/C72G produced was prepared according to the method described in (1) of Example 18 (adsorbent volume: 500 μL). Subsequently, a cell suspension of 201B7 cells prepared by the method described in (2) of Example 22 was applied to the column prepared, in an amount of 3.3×10⁶ cells/mL-adsorbent. Thereafter, application of the cell suspension to the column packed with the adsorbent, collection of the effluent cell suspension, and measurement of the fluorescence intensity of the effluent cell suspension were sequentially carried out by the method described in (3) of Example 22. As a result of calculation of the effluent rate of the 201B7 cells for the adsorbent 127Q39L/Q65L/C72G, the effluent rate was found to be 8.1%. Thus, it became clear that the adsorbent 127Q39L/Q65L/C72G, which was prepared by immobilizing the fucose-binding protein 127Q39L/Q65L/C72G of the present invention on the insoluble carrier, has a high iPS-cell adsorption capacity.

Comparative Example 12 Production of Fucose-Binding Protein 127Q39L/C72G/Q106L and Evaluation of Thermal Stability Comparative Example 12 is related to production of a fucose-binding protein (hereinafter referred to as fucose-binding protein 127Q39L/C72G/Q106L) by adding an oligopeptide containing a polyhistidine sequence to the N-terminus, and adding an oligopeptide containing a cysteine residue to the C-terminus, of the amino acid sequence which is the same as the amino acid sequence of SEQ ID NO: 3 except that the glutamine residue at position 39 is substituted with a leucine residue, that the cysteine residue at position 72 is substituted with a glycine residue, and that the glutamine residue at position 106 is substituted with a leucine residue, and evaluation of the thermal stability thereof. The fucose-binding protein 127Q39L/C72G/Q106L is the fucose-binding protein which is the same as the fucose-binding protein 127 of SEQ ID NO: 34 except that the glutamine residue at position 53 is substituted with a leucine residue, that the cysteine residue at position 86 is substituted with a glycine residue, and that the glutamine residue at position 120 is substituted with a leucine residue.

By the same method as in Example 29, the expression vector pET-BC2LCN(127Q39L/C72G/Q106L)cys for expression of the fucose-binding protein 127Q39L/C72G/Q106L, and a transformant having the expression vector were prepared. Subsequently, using the transformant prepared, the fucose-binding protein 127Q39L/C72G/Q106L was prepared by the same method as in Example 29.

In order to investigate the thermal stability of the fucose-binding protein 127Q39L/C72G/Q106L produced, the sugar-chain binding affinity of the protein after heat treatment was evaluated according to the same method as described in (3) of Reference Example 2 except that the heat treatment temperature was 83° C. For comparison, the fucose-binding protein 127Q39L/C72G produced in Example 29 was also subjected to evaluation of the sugar-chain binding affinity after heat treatment, by the same method. Table 28 shows the results of the evaluation of the sugar-chain binding capacities of the fucose-binding protein 127Q39L/C72G/Q106L and the fucose-binding protein 127Q39L/C72G after the heat treatment at 83° C. for 30 minutes. In Table 28, the sugar-chain binding capacity of each recombinant protein is expressed as a relative value with respect to the sugar-chain binding capacity after treatment at room temperature, which is taken as 100%. As shown in Table 28, it became clear that the fucose-binding protein 127Q39L/C72G/Q106L has a lower thermal stability than the fucose-binding protein 127Q39L/C72G. Thus, it became clear that, unlike substitution of the glutamine residue at position 39 in the amino acid sequence of SEQ ID NO: 3 to a leucine residue, substitution of the glutamine residue at position 106 in the amino acid sequence of SEQ ID NO: 3 to a leucine residue is not effective for improvement of the thermal stability.

[Table 28]

TABLE 28

| Recombinant protein | Sugar-chain binding capacity (%)* |
| --- | --- |
| Fucose-binding protein 127Q39L/C72G/Q106L | 33.0 |
| Fucose-binding protein 127Q39L/C72G | 57.0 |

*Relative value with respect to the sugar-chain binding capacity after treatment at room temperature, which is taken as 100%

Comparative Example 13 Production of Fucose-Binding Protein 127Q39L/Q65L/C72G/Q106L and Evaluation of Thermal Stability Comparative Example 13 is related to production of a fucose-binding protein (hereinafter referred to as fucose-binding protein 127Q39L/Q65L/C72G/Q106L) by adding an oligopeptide containing a polyhistidine sequence to the N-terminus, and adding an oligopeptide containing a cysteine residue to the C-terminus, of the amino acid sequence which is the same as the amino acid sequence of SEQ ID NO: 3 except that the glutamine residue at position 39 is substituted with a leucine residue, that the glutamine residue at position 65 is substituted with a leucine residue, that the cysteine residue at position 72 is substituted with a glycine residue, and that the glutamine residue at position 106 is substituted with a leucine residue, and evaluation of the thermal stability thereof. The fucose-binding protein 127Q39L/Q65L/C72G/Q106L is the fucose-binding protein 127 of SEQ ID NO: 34 except that the glutamine residue at position 53 is substituted with a leucine residue, that the glutamine residue at position 79 is substituted with a leucine residue, that the cysteine residue at position 86 is substituted with a glycine residue, and that the glutamine residue at position 120 is substituted with a leucine residue.

By the same method as in Example 29, the expression vector pET-BC2LCN(127Q39L/Q65L/C72G/Q106L)cys for expression of the fucose-binding protein 127Q39L/Q65L/C72G/Q106L, and a transformant having the expression vector were prepared. Subsequently, using the transformant prepared, the fucose-binding protein 127Q39L/Q65L/C72G/Q106L was produced by the same method as in Example 29.

In order to investigate the thermal stability of the fucose-binding protein 127Q39L/Q65L/C72G/Q106L produced, the sugar-chain binding affinity of the protein after heat treatment was evaluated according to the same method as described in (3) of Reference Example 2 except that the heat treatment temperature was 83° C. For comparison, the fucose-binding protein 127Q39L/Q65L/C72G produced in Example 29 was also subjected to evaluation of the sugar-chain binding affinity after heat treatment, by the same method. Table 29 shows the results of the evaluation of the sugar-chain binding capacities of the fucose-binding protein 127Q39L/Q65L/C72G/Q106L and the fucose-binding protein 127Q39L/Q65L/C72G after the heat treatment at 83° C. for 30 minutes. In Table 29, the sugar-chain binding capacity of each recombinant protein is expressed as a relative value with respect to the sugar-chain binding capacity after treatment at room temperature, which is taken as 100%. As shown in Table 29, it became clear that the fucose-binding protein 127Q39L/Q65L/C72G/Q106L has a lower thermal stability than the fucose-binding protein 127Q39L/Q65L/C72G. Thus, it became clear that, unlike substitution of the glutamine residues at positions 39 and 65 in the amino acid sequence of SEQ ID NO: 3 to leucine residues, substitution of the glutamine residue at position 106 in the amino acid sequence of SEQ ID NO: 3 to a leucine residue is not effective for improvement of the thermal stability.

[Table 29]

TABLE 29

| Recombinant protein | Sugar-chain binding capacity (%)* |
| --- | --- |
| Fucose-binding protein 127Q39L/Q65L/C72G/Q106L | 41.0 |
| Fucose-binding protein 127Q39L/Q65L/C72G | 69.0 |

*Relative value with respect to the sugar-chain binding capacity after treatment at room temperature, which is taken as 100%

Reference Example 11 Evaluation of Cell-Passing Abilities of Columns Packed with Insoluble Carriers with Various Particle Sizes Having No Fucose-Binding Protein Immobilized Thereon Reference Example 11 is related to evaluation of the cell-passing abilities of columns packed with insoluble carriers with various particle sizes having no fucose-binding protein immobilized thereon, using SP2/0-Ag14 cells (obtained from DS Pharma Biomedical Co., Ltd.; ECACC cell line number: 85072401; hereinafter referred to as SP2/0 cells), which are mouse myeloma cells having no sugar chain containing a structure composed of "Fucα1-2Galβ1-3GlcNAc and/or Fucα1-2Galβ1-3GalNAc".

(1) Preparation of Adsorbents, and Preparation of Columns Packed with Adsorbents Columns were prepared by attaching a mesh filter (manufactured by Japan BD; membrane removed from the lid of a cell strainer tube) having a mesh size of 40 μm between a 5.0-mL syringe (manufactured by Terumo Corporation) and an injection needle (manufactured by Terumo Corporation; 22 G). As insoluble carriers, Toyopearl HW-40EC (manufactured by Tosoh Corporation), which has a particle size of 100 to 300 μm, and Toyopearl HW-40C (manufactured by Tosoh Corporation), which has a particle size of 50 to 150 μm, were used. Each insoluble carrier was subjected to replacement with MACS buffer, and prepared into a 50% suspension such that the precipitation volume of the insoluble carrier after being left to stand for not less than 12 hours was 50%. Into each column prepared, 4.0 mL of the suspension was applied for packing the column with the insoluble carrier (adsorbent volume, 2.0 mL). As a control for comparison, a column not packed with an insoluble carrier was provided.

(2) Culture of SP2/0 Cells and Preparation of Cell Suspension for Evaluation

SP2/0 cells are floating cells. Using GIT medium (manufactured by Nihon Pharmaceutical Co., Ltd.), the cells were plated on a petri dish for suspension culture (manufactured by Sumitomo Bakelite Co., Ltd.), and cultured in an atmosphere of 5% $CO_2$ at 37° C.

After the culture, the cells were collected into a 50-mL tube, and centrifuged at 1500 rpm for 5 minutes, followed by discarding the supernatant. Subsequently, the precipitated cells were suspended in MACS buffer, and centrifugation was carried out again, followed by discarding the supernatant to wash the cells. After carrying out the cell washing operation twice, the cells were suspended in MACS buffer, and filtered using a cell strainer, to prepare a $1.0 \times 10^7$ cells/mL SP2/0 cell suspension.

(3) SP2/0 Cell-Passing Abilities of Columns Packed with Insoluble Carriers

Each column packed with each insoluble carrier was placed in an upright position, and the $1.0 \times 10^7$ cells/mL SP2/0 cell suspension prepared by the above method was applied to the column in an amount of $1.0 \times 10^6$ cells/mL-adsorbent.

Subsequently, 4 mL of MACS buffer was applied from the top of the column, and the effluent from the needle section was collected as an effluent cell suspension into another container. The cell concentration in the effluent cell suspension collected was measured using a Coulter Counter Z2 (manufactured by Beckman Coulter, Inc.), and the effluent rate (%) of the SP2/0 cells for each column was calculated as follows: "effluent rate (%)=number of effluent cells per syringe column/number of cells applied". Table 30 shows the cell effluent rate for each column. The effluent rate for the column packed with Toyopearl HW-40EC (particle size, 100 to 300 μm) was 73%; the effluent rate for the column packed with Toyopearl HW-40C (particle size, 50 to 150 μm) was 31%; and the effluent rate for the column not packed with an insoluble carrier was 100%. As a result of measurement of the cell diameters of SP2/0 cells using the Coulter Counter Z2, the average cell diameter of the SP2/0 cells was found to be 11.0 μm, and the dispersion was found to be 11.9%, indicating that the cells have sizes equivalent to those of normal animal cells. From these results, it became clear that a particle size of 100 to 300 μm is suitable for the insoluble carrier since such a particle size allows animal cells having common sizes to pass smoothly through gaps of the insoluble carrier. Theoretically, in the case of closest packing with spherical particles having a particle size of 100 to 300 μm, the size of cells that can pass through the gaps between the particles is estimated to be 15.5 to 46.5 μm. This supports the results of the present Reference Example. On the other hand, the cause of the low cell effluent rate for the column packed with Toyopearl HW-40C (particle size, 50 to 150 μm) may be as follows. Theoretically, in the case of closest packing with spherical particles having a particle size of 50 to 150 μm, the size of cells that can pass through the gaps between the particles is estimated to be 7.8 to 23.3 μm. Since the insoluble carrier has a particle size of 50 to 150 μm, clogging of the cells may have occurred due to the narrow gaps of the insoluble carrier.

[Table 30]

TABLE 30

| Insoluble carrier | SP2/0 cell effluent rate |
|---|---|
| Toyopearl HW-40EC | 73% |
| Toyopearl HW-40C | 31% |
| None | 100% |

INDUSTRIAL APPLICABILITY

By the present invention, a fucose-binding protein having excellent properties can be provided. More specifically, by the present invention, a fucose-binding protein that shows improved productivity in cases of expression in a host such as *Escherichia coli*, improved binding affinity to a fucose-containing sugar chain such as a sugar chain containing a structure composed of Fucα1-2Galβ1-3GlcNAc and/or Fucα1-2Galβ1-3GalNAc, and/or improved thermal stability, can be provided.

Further, by use of the fucose-binding protein of the present invention, undifferentiated cells can be selectively separated from a cell mixture containing the undifferentiated cells, and/or cancer cells can be selectively separated from a cell mixture containing the cancer cells. Thus, since the present invention can be used for highly sensitive detection and/or selective separation of undifferentiated cells and/or cancer cells, it is useful in the field of medicine, especially in the field of regenerative medicine.

The invention claimed is:

1. A fucose-binding protein comprising an amino acid sequence having at least 90% identity to amino acid residues 1 to X of SEQ ID NO: 1, wherein X is an integer of 110-140, wherein the amino acid sequence comprises at least one amino acid substitution at an amino acid residue position corresponding to an amino acid residue position of SEQ ID NO: 1 selected from the group consisting of residue position 39, 72, 65, 81, and 36;

wherein the fucose-binding protein has binding affinity to a sugar chain containing a structure composed of Fucα1-2Galβ1-3GlcNAc and/or a sugar chain containing a structure composed of Fucα1-2Galβ1-3GalNAc.

2. The fucose-binding protein according to claim 1, wherein the at least one amino acid substitution is selected from the group consisting of:

a leucine residue or a methionine residue at position 39;
    a glycine residue or an alanine residue at position 72;
    a leucine residue at position 65; a cysteine residue, a glutamine residue, a histidine residue, a methionine residue, a valine residue, a lysine residue, a serine residue, an isoleucine residue, a tyrosine residue, a glycine residue, a proline residue, a leucine residue, or an asparagine residue at position 81; and a cysteine residue at position 36.

3. The fucose-binding protein according to claim 1, having a total length of 95 to 175 residues.

4. The fucose-binding protein according to claim 1, wherein the length of the amino acid sequence is 95 to 155 residues.

5. The fucose-binding protein according to claim 1, comprising the amino acid sequence of any of SEQ ID NOs: 4, 5 and 7-16.

6. The fucose-binding protein according to claim 1 wherein the C-terminus of the amino acid sequence comprises an amino acid sequence containing a cysteine residue, or wherein the N-terminus of the amino acid sequence further comprises a polyhistidine sequence.

7. A DNA encoding the fucose-binding protein according to claim 1.

8. An expression vector comprising the DNA according to claim 7.

9. A transformant comprising the DNA according to claim 7.

10. The transformant according to claim 9, wherein the transformant is *Escherichia coli*.

11. A method of producing a fucose-binding protein, the method comprising:

culturing a transformant comprising a DNA encoding the fucose-binding protein to allow expression of the fucose-binding protein; and
    collecting the expressed fucose-binding protein;
    wherein the fucose-binding protein is the fucose-binding protein according to claim 1.

12. An adsorbent comprising:

an insoluble carrier; and
    the fucose-binding protein according to claim 1, wherein the fucose-binding protein is immobilized on the insoluble carrier.

13. A method of producing an adsorbent, the method comprising:

producing a reactive insoluble carrier from an insoluble carrier; and immobilizing the fucose-binding protein according to claim 1 on the reactive insoluble carrier;
    wherein the adsorbent comprises the fucose-binding protein is immobilized on the insoluble carrier.

14. The method according to claim 13, wherein the reactive insoluble carrier is an insoluble carrier comprising a maleimide group or a haloacetyl group.

15. A column packed with the adsorbent according to claim 12.

16. A method of separating cells, the method comprising:

bringing the adsorbent according to claim 12 into contact with a cell mixture; and separating cells adsorbed on the adsorbent, from cells not adsorbed on the adsorbent.

17. The method according to claim 16, wherein the cell mixture is a mixture containing first cells and second cells, wherein the first cells are each a cell containing a sugar chain containing a structure composed of Fucα1-2Galβ1-3GlcNAc and/or a sugar chain containing a structure composed of Fucα1-2Galβ1-3GalNAc; and wherein the second cells are each a cell containing neither a sugar chain containing a structure composed of Fucα1-2Galβ1-3GlcNAc nor a sugar chain containing a structure composed of Fucα1-2Galβ1-3GalNAc.

18. The method according to claim 17, wherein the first cells are each an undifferentiated cell, and the second cells are each a differentiated cell.

19. The method according to claim 17, wherein the first cells are each a cancer cell.

20. A method of purifying a substance containing a fucose-containing sugar chain, the method comprising:

bringing the adsorbent according to claim 12 into contact with the substance containing the fucose-containing sugar chain; wherein the substance is bound to the adsorbent; and eluting the substance bound to the adsorbent, wherein the fucose-containing sugar chain is a sugar chain containing a structure composed of Fucα1-2Galβ1-3GlcNAc and/or a sugar chain containing a structure composed of Fucα1-2Galβ1-3GalNAc.

21. The method according to claim 20, wherein the substance is the fucose-containing sugar chain a glycoconjugates containing the fucose-containing sugar chain.

22. The method according to claim 16, wherein the adsorbent is packed in a column.

23. The method according to claim 16, wherein the adsorbent is packed in a column.

* * * * *

SEQUENCE LISTING

```
<160> NUMBER OF SEQ ID NOS: 67

<210> SEQ ID NO 1
<211> LENGTH: 155
<212> TYPE: PRT
<213> ORGANISM: Burkholderia cenocepacia

<400> SEQUENCE: 1

Pro Leu Leu Ser Ala Ser Ile Val Ser Ala Pro Val Val Thr Ser Glu
1               5                   10                  15
```

```
Thr Tyr Val Asp Ile Pro Gly Leu Tyr Leu Asp Val Ala Lys Ala Gly
            20                  25                  30

Ile Arg Asp Gly Lys Leu Gln Val Ile Leu Asn Val Pro Thr Pro Tyr
            35                  40                  45

Ala Thr Gly Asn Asn Phe Pro Gly Ile Tyr Phe Ala Ile Ala Thr Asn
        50                  55                  60

Gln Gly Val Val Ala Asp Gly Cys Phe Thr Tyr Ser Ser Lys Val Pro
65                  70                  75                  80

Glu Ser Thr Gly Arg Met Pro Phe Thr Leu Val Ala Thr Ile Asp Val
                85                  90                  95

Gly Ser Gly Val Thr Phe Val Lys Gly Gln Trp Lys Ser Val Arg Gly
            100                 105                 110

Ser Ala Met His Ile Asp Ser Tyr Ala Ser Leu Ser Ala Ile Trp Gly
        115                 120                 125

Thr Ala Ala Pro Ser Ser Gln Gly Ser Gly Asn Gln Gly Ala Glu Thr
    130                 135                 140

Gly Gly Thr Gly Ala Gly Asn Ile Gly Gly Gly
145                 150                 155
```

```
<210> SEQ ID NO 2
<211> LENGTH: 129
<212> TYPE: PRT
<213> ORGANISM: Artificial Sequence
<220> FEATURE:
<223> OTHER INFORMATION: BC2LCN129

<400> SEQUENCE: 2

Pro Leu Leu Ser Ala Ser Ile Val Ser Ala Pro Val Val Thr Ser Glu
1               5                   10                  15

Thr Tyr Val Asp Ile Pro Gly Leu Tyr Leu Asp Val Ala Lys Ala Gly
            20                  25                  30

Ile Arg Asp Gly Lys Leu Gln Val Ile Leu Asn Val Pro Thr Pro Tyr
            35                  40                  45

Ala Thr Gly Asn Asn Phe Pro Gly Ile Tyr Phe Ala Ile Ala Thr Asn
        50                  55                  60

Gln Gly Val Val Ala Asp Gly Cys Phe Thr Tyr Ser Ser Lys Val Pro
65                  70                  75                  80

Glu Ser Thr Gly Arg Met Pro Phe Thr Leu Val Ala Thr Ile Asp Val
                85                  90                  95

Gly Ser Gly Val Thr Phe Val Lys Gly Gln Trp Lys Ser Val Arg Gly
            100                 105                 110

Ser Ala Met His Ile Asp Ser Tyr Ala Ser Leu Ser Ala Ile Trp Gly
        115                 120                 125

Thr
```

```
<210> SEQ ID NO 3
<211> LENGTH: 127
<212> TYPE: PRT
<213> ORGANISM: Artificial Sequence
<220> FEATURE:
<223> OTHER INFORMATION: BC2LCN127

<400> SEQUENCE: 3

Pro Leu Leu Ser Ala Ser Ile Val Ser Ala Pro Val Val Thr Ser Glu
1               5                   10                  15

Thr Tyr Val Asp Ile Pro Gly Leu Tyr Leu Asp Val Ala Lys Ala Gly
            20                  25                  30
```

```
Ile Arg Asp Gly Lys Leu Gln Val Ile Leu Asn Val Pro Thr Pro Tyr
        35                  40                  45

Ala Thr Gly Asn Asn Phe Pro Gly Ile Tyr Phe Ala Ile Ala Thr Asn
    50                  55                  60

Gln Gly Val Val Ala Asp Gly Cys Phe Thr Tyr Ser Ser Lys Val Pro
65                  70                  75                  80

Glu Ser Thr Gly Arg Met Pro Phe Thr Leu Val Ala Thr Ile Asp Val
                85                  90                  95

Gly Ser Gly Val Thr Phe Val Lys Gly Gln Trp Lys Ser Val Arg Gly
            100                 105                 110

Ser Ala Met His Ile Asp Ser Tyr Ala Ser Leu Ser Ala Ile Trp
        115                 120                 125
```

```
<210> SEQ ID NO 4
<211> LENGTH: 129
<212> TYPE: PRT
<213> ORGANISM: Artificial Sequence
<220> FEATURE:
<223> OTHER INFORMATION: BC2LCN129G36C

<400> SEQUENCE: 4
```

```
Pro Leu Leu Ser Ala Ser Ile Val Ser Ala Pro Val Val Thr Ser Glu
1               5                   10                  15

Thr Tyr Val Asp Ile Pro Gly Leu Tyr Leu Asp Val Ala Lys Ala Gly
                20                  25                  30

Ile Arg Asp Cys Lys Leu Gln Val Ile Leu Asn Val Pro Thr Pro Tyr
        35                  40                  45

Ala Thr Gly Asn Asn Phe Pro Gly Ile Tyr Phe Ala Ile Ala Thr Asn
    50                  55                  60

Gln Gly Val Val Ala Asp Gly Cys Phe Thr Tyr Ser Ser Lys Val Pro
65                  70                  75                  80

Glu Ser Thr Gly Arg Met Pro Phe Thr Leu Val Ala Thr Ile Asp Val
                85                  90                  95

Gly Ser Gly Val Thr Phe Val Lys Gly Gln Trp Lys Ser Val Arg Gly
            100                 105                 110

Ser Ala Met His Ile Asp Ser Tyr Ala Ser Leu Ser Ala Ile Trp Gly
        115                 120                 125

Thr
```

```
<210> SEQ ID NO 5
<211> LENGTH: 127
<212> TYPE: PRT
<213> ORGANISM: Artificial Sequence
<220> FEATURE:
<223> OTHER INFORMATION: BC2LCN127G36C

<400> SEQUENCE: 5
```

```
Pro Leu Leu Ser Ala Ser Ile Val Ser Ala Pro Val Val Thr Ser Glu
1               5                   10                  15

Thr Tyr Val Asp Ile Pro Gly Leu Tyr Leu Asp Val Ala Lys Ala Gly
                20                  25                  30

Ile Arg Asp Cys Lys Leu Gln Val Ile Leu Asn Val Pro Thr Pro Tyr
        35                  40                  45

Ala Thr Gly Asn Asn Phe Pro Gly Ile Tyr Phe Ala Ile Ala Thr Asn
    50                  55                  60

Gln Gly Val Val Ala Asp Gly Cys Phe Thr Tyr Ser Ser Lys Val Pro
65                  70                  75                  80
```

```
Glu Ser Thr Gly Arg Met Pro Phe Thr Leu Val Ala Thr Ile Asp Val
                85              90              95

Gly Ser Gly Val Thr Phe Val Lys Gly Gln Trp Lys Ser Val Arg Gly
            100             105             110

Ser Ala Met His Ile Asp Ser Tyr Ala Ser Leu Ser Ala Ile Trp
        115             120             125
```

<210> SEQ ID NO 6
<211> LENGTH: 126
<212> TYPE: PRT
<213> ORGANISM: Artificial Sequence
<220> FEATURE:
<223> OTHER INFORMATION: BC2LCN126

<400> SEQUENCE: 6

```
Pro Leu Leu Ser Ala Ser Ile Val Ser Ala Pro Val Val Thr Ser Glu
1               5               10              15

Thr Tyr Val Asp Ile Pro Gly Leu Tyr Leu Asp Val Ala Lys Ala Gly
            20              25              30

Ile Arg Asp Gly Lys Leu Gln Val Ile Leu Asn Val Pro Thr Pro Tyr
        35              40              45

Ala Thr Gly Asn Asn Phe Pro Gly Ile Tyr Phe Ala Ile Ala Thr Asn
    50              55              60

Gln Gly Val Val Ala Asp Gly Cys Phe Thr Tyr Ser Ser Lys Val Pro
65              70              75              80

Glu Ser Thr Gly Arg Met Pro Phe Thr Leu Val Ala Thr Ile Asp Val
                85              90              95

Gly Ser Gly Val Thr Phe Val Lys Gly Gln Trp Lys Ser Val Arg Gly
            100             105             110

Ser Ala Met His Ile Asp Ser Tyr Ala Ser Leu Ser Ala Ile
        115             120             125
```

<210> SEQ ID NO 7
<211> LENGTH: 129
<212> TYPE: PRT
<213> ORGANISM: Artificial Sequence
<220> FEATURE:
<223> OTHER INFORMATION: BC2LCN129E81C

<400> SEQUENCE: 7

```
Pro Leu Leu Ser Ala Ser Ile Val Ser Ala Pro Val Val Thr Ser Glu
1               5               10              15

Thr Tyr Val Asp Ile Pro Gly Leu Tyr Leu Asp Val Ala Lys Ala Gly
            20              25              30

Ile Arg Asp Gly Lys Leu Gln Val Ile Leu Asn Val Pro Thr Pro Tyr
        35              40              45

Ala Thr Gly Asn Asn Phe Pro Gly Ile Tyr Phe Ala Ile Ala Thr Asn
    50              55              60

Gln Gly Val Val Ala Asp Gly Cys Phe Thr Tyr Ser Ser Lys Val Pro
65              70              75              80

Cys Ser Thr Gly Arg Met Pro Phe Thr Leu Val Ala Thr Ile Asp Val
                85              90              95

Gly Ser Gly Val Thr Phe Val Lys Gly Gln Trp Lys Ser Val Arg Gly
            100             105             110

Ser Ala Met His Ile Asp Ser Tyr Ala Ser Leu Ser Ala Ile Trp Gly
        115             120             125

Thr
```

<210> SEQ ID NO 8
<211> LENGTH: 129
<212> TYPE: PRT
<213> ORGANISM: Artificial Sequence
<220> FEATURE:
<223> OTHER INFORMATION: BC2LCN129E81Q

<400> SEQUENCE: 8

Pro Leu Leu Ser Ala Ser Ile Val Ser Ala Pro Val Val Thr Ser Glu
1               5                   10                  15

Thr Tyr Val Asp Ile Pro Gly Leu Tyr Leu Asp Val Ala Lys Ala Gly
                20                  25                  30

Ile Arg Asp Gly Lys Leu Gln Val Ile Leu Asn Val Pro Thr Pro Tyr
            35                  40                  45

Ala Thr Gly Asn Asn Phe Pro Gly Ile Tyr Phe Ala Ile Ala Thr Asn
        50                  55                  60

Gln Gly Val Val Ala Asp Gly Cys Phe Thr Tyr Ser Ser Lys Val Pro
65                  70                  75                  80

Gln Ser Thr Gly Arg Met Pro Phe Thr Leu Val Ala Thr Ile Asp Val
                85                  90                  95

Gly Ser Gly Val Thr Phe Val Lys Gly Gln Trp Lys Ser Val Arg Gly
            100                 105                 110

Ser Ala Met His Ile Asp Ser Tyr Ala Ser Leu Ser Ala Ile Trp Gly
        115                 120                 125

Thr

<210> SEQ ID NO 9
<211> LENGTH: 129
<212> TYPE: PRT
<213> ORGANISM: Artificial Sequence
<220> FEATURE:
<223> OTHER INFORMATION: BC2LCN129E81H

<400> SEQUENCE: 9

Pro Leu Leu Ser Ala Ser Ile Val Ser Ala Pro Val Val Thr Ser Glu
1               5                   10                  15

Thr Tyr Val Asp Ile Pro Gly Leu Tyr Leu Asp Val Ala Lys Ala Gly
                20                  25                  30

Ile Arg Asp Gly Lys Leu Gln Val Ile Leu Asn Val Pro Thr Pro Tyr
            35                  40                  45

Ala Thr Gly Asn Asn Phe Pro Gly Ile Tyr Phe Ala Ile Ala Thr Asn
        50                  55                  60

Gln Gly Val Val Ala Asp Gly Cys Phe Thr Tyr Ser Ser Lys Val Pro
65                  70                  75                  80

His Ser Thr Gly Arg Met Pro Phe Thr Leu Val Ala Thr Ile Asp Val
                85                  90                  95

Gly Ser Gly Val Thr Phe Val Lys Gly Gln Trp Lys Ser Val Arg Gly
            100                 105                 110

Ser Ala Met His Ile Asp Ser Tyr Ala Ser Leu Ser Ala Ile Trp Gly
        115                 120                 125

Thr

<210> SEQ ID NO 10
<211> LENGTH: 129
<212> TYPE: PRT
<213> ORGANISM: Artificial Sequence
<220> FEATURE:
<223> OTHER INFORMATION: BC2LCN129E81M -continued

```
<400> SEQUENCE: 10

Pro Leu Leu Ser Ala Ser Ile Val Ser Ala Pro Val Val Thr Ser Glu
1               5                   10                  15

Thr Tyr Val Asp Ile Pro Gly Leu Tyr Leu Asp Val Ala Lys Ala Gly
                20                  25                  30

Ile Arg Asp Gly Lys Leu Gln Val Ile Leu Asn Val Pro Thr Pro Tyr
            35                  40                  45

Ala Thr Gly Asn Asn Phe Pro Gly Ile Tyr Phe Ala Ile Ala Thr Asn
        50                  55                  60

Gln Gly Val Val Ala Asp Gly Cys Phe Thr Tyr Ser Ser Lys Val Pro
65                  70                  75                  80

Met Ser Thr Gly Arg Met Pro Phe Thr Leu Val Ala Thr Ile Asp Val
                85                  90                  95

Gly Ser Gly Val Thr Phe Val Lys Gly Gln Trp Lys Ser Val Arg Gly
            100                 105                 110

Ser Ala Met His Ile Asp Ser Tyr Ala Ser Leu Ser Ala Ile Trp Gly
        115                 120                 125

Thr

<210> SEQ ID NO 11
<211> LENGTH: 127
<212> TYPE: PRT
<213> ORGANISM: Artificial Sequence
<220> FEATURE:
<223> OTHER INFORMATION: BC2LCN127C72G

<400> SEQUENCE: 11

Pro Leu Leu Ser Ala Ser Ile Val Ser Ala Pro Val Val Thr Ser Glu
1               5                   10                  15

Thr Tyr Val Asp Ile Pro Gly Leu Tyr Leu Asp Val Ala Lys Ala Gly
                20                  25                  30

Ile Arg Asp Gly Lys Leu Gln Val Ile Leu Asn Val Pro Thr Pro Tyr
            35                  40                  45

Ala Thr Gly Asn Asn Phe Pro Gly Ile Tyr Phe Ala Ile Ala Thr Asn
        50                  55                  60

Gln Gly Val Val Ala Asp Gly Gly Phe Thr Tyr Ser Ser Lys Val Pro
65                  70                  75                  80

Glu Ser Thr Gly Arg Met Pro Phe Thr Leu Val Ala Thr Ile Asp Val
                85                  90                  95

Gly Ser Gly Val Thr Phe Val Lys Gly Gln Trp Lys Ser Val Arg Gly
            100                 105                 110

Ser Ala Met His Ile Asp Ser Tyr Ala Ser Leu Ser Ala Ile Trp
        115                 120                 125

<210> SEQ ID NO 12
<211> LENGTH: 127
<212> TYPE: PRT
<213> ORGANISM: Artificial Sequence
<220> FEATURE:
<223> OTHER INFORMATION: BC2LCN127C72A

<400> SEQUENCE: 12

Pro Leu Leu Ser Ala Ser Ile Val Ser Ala Pro Val Val Thr Ser Glu
1               5                   10                  15

Thr Tyr Val Asp Ile Pro Gly Leu Tyr Leu Asp Val Ala Lys Ala Gly
                20                  25                  30
```

-continued

```
Ile Arg Asp Gly Lys Leu Gln Val Ile Leu Asn Val Pro Thr Pro Tyr
        35              40              45

Ala Thr Gly Asn Asn Phe Pro Gly Ile Tyr Phe Ala Ile Ala Thr Asn
    50              55              60

Gln Gly Val Val Ala Asp Gly Ala Phe Thr Tyr Ser Ser Lys Val Pro
65              70              75              80

Glu Ser Thr Gly Arg Met Pro Phe Thr Leu Val Ala Thr Ile Asp Val
                85              90              95

Gly Ser Gly Val Thr Phe Val Lys Gly Gln Trp Lys Ser Val Arg Gly
            100             105             110

Ser Ala Met His Ile Asp Ser Tyr Ala Ser Leu Ser Ala Ile Trp
        115             120             125
```

```
<210> SEQ ID NO 13
<211> LENGTH: 127
<212> TYPE: PRT
<213> ORGANISM: Artificial Sequence
<220> FEATURE:
<223> OTHER INFORMATION: BC2LCN127Q39L
```

```
<400> SEQUENCE: 13
```

```
Pro Leu Leu Ser Ala Ser Ile Val Ser Ala Pro Val Val Thr Ser Glu
1               5               10              15

Thr Tyr Val Asp Ile Pro Gly Leu Tyr Leu Asp Val Ala Lys Ala Gly
                20              25              30

Ile Arg Asp Gly Lys Leu Leu Val Ile Leu Asn Val Pro Thr Pro Tyr
        35              40              45

Ala Thr Gly Asn Asn Phe Pro Gly Ile Tyr Phe Ala Ile Ala Thr Asn
    50              55              60

Gln Gly Val Val Ala Asp Gly Cys Phe Thr Tyr Ser Ser Lys Val Pro
65              70              75              80

Glu Ser Thr Gly Arg Met Pro Phe Thr Leu Val Ala Thr Ile Asp Val
                85              90              95

Gly Ser Gly Val Thr Phe Val Lys Gly Gln Trp Lys Ser Val Arg Gly
            100             105             110

Ser Ala Met His Ile Asp Ser Tyr Ala Ser Leu Ser Ala Ile Trp
        115             120             125
```

```
<210> SEQ ID NO 14
<211> LENGTH: 127
<212> TYPE: PRT
<213> ORGANISM: Artificial Sequence
<220> FEATURE:
<223> OTHER INFORMATION: BC2LCN127Q39M
```

```
<400> SEQUENCE: 14
```

```
Pro Leu Leu Ser Ala Ser Ile Val Ser Ala Pro Val Val Thr Ser Glu
1               5               10              15

Thr Tyr Val Asp Ile Pro Gly Leu Tyr Leu Asp Val Ala Lys Ala Gly
                20              25              30

Ile Arg Asp Gly Lys Leu Met Val Ile Leu Asn Val Pro Thr Pro Tyr
        35              40              45

Ala Thr Gly Asn Asn Phe Pro Gly Ile Tyr Phe Ala Ile Ala Thr Asn
    50              55              60

Gln Gly Val Val Ala Asp Gly Cys Phe Thr Tyr Ser Ser Lys Val Pro
65              70              75              80

Glu Ser Thr Gly Arg Met Pro Phe Thr Leu Val Ala Thr Ile Asp Val
                85              90              95
```

-continued

```
Gly Ser Gly Val Thr Phe Val Lys Gly Gln Trp Lys Ser Val Arg Gly
            100                 105                 110

Ser Ala Met His Ile Asp Ser Tyr Ala Ser Leu Ser Ala Ile Trp
            115                 120                 125

<210> SEQ ID NO 15
<211> LENGTH: 127
<212> TYPE: PRT
<213> ORGANISM: Artificial Sequence
<220> FEATURE:
<223> OTHER INFORMATION: BC2LCN127Q39L/C72G

<400> SEQUENCE: 15

Pro Leu Leu Ser Ala Ser Ile Val Ser Ala Pro Val Val Thr Ser Glu
1               5                   10                  15

Thr Tyr Val Asp Ile Pro Gly Leu Tyr Leu Asp Val Ala Lys Ala Gly
            20                  25                  30

Ile Arg Asp Gly Lys Leu Leu Val Ile Leu Asn Val Pro Thr Pro Tyr
            35                  40                  45

Ala Thr Gly Asn Asn Phe Pro Gly Ile Tyr Phe Ala Ile Ala Thr Asn
        50                  55                  60

Gln Gly Val Val Ala Asp Gly Gly Phe Thr Tyr Ser Ser Lys Val Pro
65                  70                  75                  80

Glu Ser Thr Gly Arg Met Pro Phe Thr Leu Val Ala Thr Ile Asp Val
            85                  90                  95

Gly Ser Gly Val Thr Phe Val Lys Gly Gln Trp Lys Ser Val Arg Gly
            100                 105                 110

Ser Ala Met His Ile Asp Ser Tyr Ala Ser Leu Ser Ala Ile Trp
            115                 120                 125

<210> SEQ ID NO 16
<211> LENGTH: 127
<212> TYPE: PRT
<213> ORGANISM: Artificial Sequence
<220> FEATURE:
<223> OTHER INFORMATION: BC2LCN127Q39L/Q65L/C72G

<400> SEQUENCE: 16

Pro Leu Leu Ser Ala Ser Ile Val Ser Ala Pro Val Val Thr Ser Glu
1               5                   10                  15

Thr Tyr Val Asp Ile Pro Gly Leu Tyr Leu Asp Val Ala Lys Ala Gly
            20                  25                  30

Ile Arg Asp Gly Lys Leu Leu Val Ile Leu Asn Val Pro Thr Pro Tyr
            35                  40                  45

Ala Thr Gly Asn Asn Phe Pro Gly Ile Tyr Phe Ala Ile Ala Thr Asn
        50                  55                  60

Leu Gly Val Val Ala Asp Gly Gly Phe Thr Tyr Ser Ser Lys Val Pro
65                  70                  75                  80

Glu Ser Thr Gly Arg Met Pro Phe Thr Leu Val Ala Thr Ile Asp Val
            85                  90                  95

Gly Ser Gly Val Thr Phe Val Lys Gly Gln Trp Lys Ser Val Arg Gly
            100                 105                 110

Ser Ala Met His Ile Asp Ser Tyr Ala Ser Leu Ser Ala Ile Trp
            115                 120                 125

<210> SEQ ID NO 17
<211> LENGTH: 387
<212> TYPE: DNA
```

-continued

<213> ORGANISM: Artificial Sequence
<220> FEATURE:
<223> OTHER INFORMATION: DNA coding for BC2LCN129

<400> SEQUENCE: 17

```
ccccttttga gcgcaagcat tgtcagcgca ccggttgtga cctccgaaac ctatgtggat      60
ataccgggcc tgtatctgga tgtggcgaaa gcggggattc gtgatggcaa actgcaggtg     120
attctgaatg tgccgacccc gtatgcgacc ggcaacaact ttccgggaat ttactttgcg     180
attgcgacca atcagggcgt tgtggcggat ggctgtttta cctatagctc caaggtaccg     240
gagagcacgg ggcgtatgcc gtttaccttg gtggcgacca ttgatgtggg ctcgggcgtg     300
accttcgtga aaggccagtg gaaatcagtg cggggcagcg cgatgcatat tgatagctac     360
gcgagccttt cggcgatttg gggcacc                                        387
```

<210> SEQ ID NO 18
<211> LENGTH: 381
<212> TYPE: DNA
<213> ORGANISM: Artificial Sequence
<220> FEATURE:
<223> OTHER INFORMATION: DNA coding for BC2LCN127

<400> SEQUENCE: 18

```
ccccttttga gcgcaagcat tgtcagcgca ccggttgtga cctccgaaac ctatgtggat      60
ataccgggcc tgtatctgga tgtggcgaaa gcggggattc gtgatggcaa actgcaggtg     120
attctgaatg tgccgacccc gtatgcgacc ggcaacaact ttccgggaat ttactttgcg     180
attgcgacca atcagggcgt tgtggcggat ggctgtttta cctatagctc caaggtaccg     240
gagagcacgg ggcgtatgcc gtttaccttg gtggcgacca ttgatgtggg ctcgggcgtg     300
accttcgtga aaggccagtg gaaatcagtg cggggcagcg cgatgcatat tgatagctac     360
gcgagccttt cggcgatttg g                                              381
```

<210> SEQ ID NO 19
<211> LENGTH: 387
<212> TYPE: DNA
<213> ORGANISM: Artificial Sequence
<220> FEATURE:
<223> OTHER INFORMATION: DNA coding for BC2LCN129G36C

<400> SEQUENCE: 19

```
ccccttttga gcgcaagcat tgtcagcgca ccggttgtga cctccgaaac ctatgtggat      60
ataccgggcc tgtatctgga tgtggcgaaa gcggggattc gtgattgcaa actgcaggtg     120
attctgaatg tgccgacccc gtatgcgacc ggcaacaact ttccgggaat ttactttgcg     180
attgcgacca atcagggcgt tgtggcggat ggctgtttta cctatagctc caaggtaccg     240
gagagcacgg ggcgtatgcc gtttaccttg gtggcgacca ttgatgtggg ctcgggcgtg     300
accttcgtga aaggccagtg gaaatcagtg cggggcagcg cgatgcatat tgatagctac     360
gcgagccttt cggcgatttg gggcacc                                        387
```

<210> SEQ ID NO 20
<211> LENGTH: 381
<212> TYPE: DNA
<213> ORGANISM: Artificial Sequence
<220> FEATURE:
<223> OTHER INFORMATION: DNA coding for BC2LCN127G36C

<400> SEQUENCE: 20

```
ccccttttga gcgcaagcat tgtcagcgca ccggttgtga cctccgaaac ctatgtggat      60
```

```
ataccgggcc tgtatctgga tgtggcgaaa gcggggattc gtgattgcaa actgcaggtg        120
attctgaatg tgccgacccc gtatgcgacc ggcaacaact ttccgggaat ttactttgcg        180
attgcgacca atcagggcgt tgtggcggat ggctgtttta cctatagctc caaggtaccg        240
gagagcacgg ggcgtatgcc gtttaccttg gtggcgacca ttgatgtggg ctcgggcgtg        300
accttcgtga aaggccagtg gaaatcagtg cggggcagcg cgatgcatat tgatagctac        360
gcgagccttt cggcgatttg g                                                  381
```

<210> SEQ ID NO 21
<211> LENGTH: 378
<212> TYPE: DNA
<213> ORGANISM: Artificial Sequence
<220> FEATURE:
<223> OTHER INFORMATION: DNA coding for BC2LCN126

<400> SEQUENCE: 21

```
ccccttttga gcgcaagcat tgtcagcgca ccggttgtga cctccgaaac ctatgtggat         60
ataccgggcc tgtatctgga tgtggcgaaa gcggggattc gtgatggcaa actgcaggtg        120
attctgaatg tgccgacccc gtatgcgacc ggcaacaact ttccgggaat ttactttgcg        180
attgcgacca atcagggcgt tgtggcggat ggctgtttta cctatagctc caaggtaccg        240
gagagcacgg ggcgtatgcc gtttaccttg gtggcgacca ttgatgtggg ctcgggcgtg        300
accttcgtga aaggccagtg gaaatcagtg cggggcagcg cgatgcatat tgatagctac        360
gcgagccttt cggcgatt                                                      378
```

<210> SEQ ID NO 22
<211> LENGTH: 387
<212> TYPE: DNA
<213> ORGANISM: Artificial Sequence
<220> FEATURE:
<223> OTHER INFORMATION: DNA coding for BC2LCN129E81C

<400> SEQUENCE: 22

```
ccccttttga gcgcaagcat tgtcagcgca ccggttgtga cctccgaaac ctatgtggat         60
ataccgggcc tgtatctgga tgtggcgaaa gcggggattc gtgatggcaa actgcaggtg        120
attctgaatg tgccgacccc gtatgcgacc ggcaacaact ttccgggaat ttactttgcg        180
attgcgacca atcagggcgt tgtggcggat ggctgtttta cctatagctc caaggtaccg        240
tgcagcacgg ggcgtatgcc gtttaccttg gtggcgacca ttgatgtggg ctcgggcgtg        300
accttcgtga aaggccagtg gaaatcagtg cggggcagcg cgatgcatat tgatagctac        360
gcgagccttt cggcgatttg gggcacc                                            387
```

<210> SEQ ID NO 23
<211> LENGTH: 387
<212> TYPE: DNA
<213> ORGANISM: Artificial Sequence
<220> FEATURE:
<223> OTHER INFORMATION: DNA coding for BC2LCN129E81Q

<400> SEQUENCE: 23

```
ccccttttga gcgcaagcat tgtcagcgca ccggttgtga cctccgaaac ctatgtggat         60
ataccgggcc tgtatctgga tgtggcgaaa gcggggattc gtgatggcaa actgcaggtg        120
attctgaatg tgccgacccc gtatgcgacc ggcaacaact ttccgggaat ttactttgcg        180
attgcgacca atcagggcgt tgtggcggat ggctgtttta cctatagctc caaggtaccg        240
```

```
cagagcacgg ggcgtatgcc gtttaccttg gtggcgacca ttgatgtggg ctcgggcgtg     300
accttcgtga aaggccagtg gaaatcagtg cggggcagcg cgatgcatat tgatagctac     360
gcgagccttt cggcgatttg gggcacc                                         387

<210> SEQ ID NO 24
<211> LENGTH: 387
<212> TYPE: DNA
<213> ORGANISM: Artificial Sequence
<220> FEATURE:
<223> OTHER INFORMATION: DNA coding for BC2LCN129E81H

<400> SEQUENCE: 24
ccccttttga gcgcaagcat tgtcagcgca ccggttgtga cctccgaaac ctatgtggat      60
ataccgggcc tgtatctgga tgtggcgaaa gcggggattc gtgatggcaa actgcaggtg     120
attctgaatg tgccgacccc gtatgcgacc ggcaacaact ttccgggaat ttactttgcg     180
attgcgacca tcagggcgt tgtggcggat ggctgtttta cctatagctc caaggtaccg     240
catagcacgg ggcgtatgcc gtttaccttg gtggcgacca ttgatgtggg ctcgggcgtg     300
accttcgtga aaggccagtg gaaatcagtg cggggcagcg cgatgcatat tgatagctac     360
gcgagccttt cggcgatttg gggcacc                                         387

<210> SEQ ID NO 25
<211> LENGTH: 387
<212> TYPE: DNA
<213> ORGANISM: Artificial Sequence
<220> FEATURE:
<223> OTHER INFORMATION: DNA coding for BC2LCN129E81M

<400> SEQUENCE: 25
ccccttttga gcgcaagcat tgtcagcgca ccggttgtga cctccgaaac ctatgtggat      60
ataccgggcc tgtatctgga tgtggcgaaa gcggggattc gtgatggcaa actgcaggtg     120
attctgaatg tgccgacccc gtatgcgacc ggcaacaact ttccgggaat ttactttgcg     180
attgcgacca tcagggcgt tgtggcggat ggctgtttta cctatagctc caaggtaccg     240
atgagcacgg ggcgtatgcc gtttaccttg gtggcgacca ttgatgtggg ctcgggcgtg     300
accttcgtga aaggccagtg gaaatcagtg cggggcagcg cgatgcatat tgatagctac     360
gcgagccttt cggcgatttg gggcacc                                         387

<210> SEQ ID NO 26
<211> LENGTH: 381
<212> TYPE: DNA
<213> ORGANISM: Artificial Sequence
<220> FEATURE:
<223> OTHER INFORMATION: DNA coding for BC2LCN127C72G

<400> SEQUENCE: 26
ccccttttga gcgcaagcat tgtcagcgca ccggttgtga cctccgaaac ctatgtggat      60
ataccgggcc tgtatctgga tgtggcgaaa gcggggattc gtgatggcaa actgcaggtg     120
attctgaatg tgccgacccc gtatgcgacc ggcaacaact ttccgggaat ttactttgcg     180
attgcgacca tcagggcgt tgtggcggat ggcgggttta cctatagctc caaggtaccg     240
gagagtactg ggcgtatgcc gtttaccttg gtggcgacca ttgatgtggg ctcgggcgtg     300
accttcgtga aaggccagtg gaaatcagtg cggggatccg cgatgcatat tgatagctac     360
gcgagccttt cggcgatttg g                                               381
```

```
<210> SEQ ID NO 27
<211> LENGTH: 381
<212> TYPE: DNA
<213> ORGANISM: Artificial Sequence
<220> FEATURE:
<223> OTHER INFORMATION: DNA coding for BC2LCN127C72A

<400> SEQUENCE: 27 cccctttttga gcgcaagcat tgtcagcgca ccggttgtga cctccgaaac ctatgtggat      60
ataccgggcc tgtatctgga tgtggcgaaa gcggggattc gtgatggcaa actgcaggtg     120
attctgaatg tgccgacccc gtatgcgacc ggcaacaact ttccgggaat ttactttgcg     180
attgcgacca atcagggcgt tgtggcggat ggcgccttta cctatagctc caaggtaccg     240
gagagtactg ggcgtatgcc gtttaccttg gtggcgacca ttgatgtggg ctcgggcgtg     300
accttcgtga aaggccagtg gaaatcagtg cggggatccg cgatgcatat tgatagctac     360
gcgagccttt cggcgatttg g                                                381

<210> SEQ ID NO 28
<211> LENGTH: 381
<212> TYPE: DNA
<213> ORGANISM: Artificial Sequence
<220> FEATURE:
<223> OTHER INFORMATION: DNA coding for BC2LCN127Q39L

<400> SEQUENCE: 28 cccctttttga gcgcaagcat tgtcagcgca ccggttgtga cctccgaaac ctatgtggat      60
ataccgggcc tgtatctgga tgtggcgaaa gcggggattc gtgatggcaa actgctggtg     120
attctgaatg tgccgacccc gtatgcgacc ggcaacaact ttccgggaat ttactttgcg     180
attgcgacca atcagggcgt tgtggcggat ggctgtttta cctatagctc caaggtaccg     240
gagagcacgg ggcgtatgcc gtttaccttg gtggcgacca ttgatgtggg ctcgggcgtg     300
accttcgtga aaggccagtg gaaatcagtg cggggcagcg cgatgcatat tgatagctac     360
gcgagccttt cggcgatttg g                                                381

<210> SEQ ID NO 29
<211> LENGTH: 381
<212> TYPE: DNA
<213> ORGANISM: Artificial Sequence
<220> FEATURE:
<223> OTHER INFORMATION: DNA coding for BC2LCN127Q39M

<400> SEQUENCE: 29 cccctttttga gcgcaagcat tgtcagcgca ccggttgtga cctccgaaac ctatgtggat      60
ataccgggcc tgtatctgga tgtggcgaaa gcggggattc gtgatggcaa actgatggtg     120
attctgaatg tgccgacccc gtatgcgacc ggcaacaact ttccgggaat ttactttgcg     180
attgcgacca atcagggcgt tgtggcggat ggctgtttta cctatagctc caaggtaccg     240
gagagcacgg ggcgtatgcc gtttaccttg gtggcgacca ttgatgtggg ctcgggcgtg     300
accttcgtga aaggccagtg gaaatcagtg cggggcagcg cgatgcatat tgatagctac     360
gcgagccttt cggcgatttg g                                                381

<210> SEQ ID NO 30
<211> LENGTH: 381
<212> TYPE: DNA
<213> ORGANISM: Artificial Sequence
<220> FEATURE:
<223> OTHER INFORMATION: DNA coding for BC2LCN127Q39L/C72G
```

-continued

<400> SEQUENCE: 30 cccctttttga gcgcaagcat tgtcagcgca ccggttgtga cctccgaaac ctatgtggat      60
ataccgggcc tgtatctgga tgtggcgaaa gcggggattc gtgatggcaa actgctggtg     120
attctgaatg tgccgacccc gtatgcgacc ggcaacaact ttccgggaat ttactttgcg     180
attgcgacca atcagggcgt tgtggcggat ggcggtttta cctatagctc caaggtaccg     240
gagagcacgg ggcgtatgcc gtttaccttg gtggcgacca ttgatgtggg ctcgggcgtg     300
accttcgtga aaggccagtg gaaatcagtg cggggcagcg cgatgcatat tgatagctac     360
gcgagccttt cggcgatttg g                                                381

<210> SEQ ID NO 31
<211> LENGTH: 381
<212> TYPE: DNA
<213> ORGANISM: Artificial Sequence
<220> FEATURE:
<223> OTHER INFORMATION: DNA coding for BC2LCN127Q39L/Q65L/C72G

<400> SEQUENCE: 31 cccctttttga gcgcaagcat tgtcagcgca ccggttgtga cctccgaaac ctatgtggat      60
ataccgggcc tgtatctgga tgtggcgaaa gcggggattc gtgatggcaa actgctggtg     120
attctgaatg tgccgacccc gtatgcgacc ggcaacaact ttccgggaat ttactttgcg     180
attgcgacca atctgggcgt tgtggcggat ggcggtttta cctatagctc caaggtaccg     240
gagagcacgg ggcgtatgcc gtttaccttg gtggcgacca ttgatgtggg ctcgggcgtg     300
accttcgtga aaggccagtg gaaatcagtg cggggcagcg cgatgcatat tgatagctac     360
gcgagccttt cggcgatttg g                                                381

<210> SEQ ID NO 32
<211> LENGTH: 174
<212> TYPE: PRT
<213> ORGANISM: Artificial Sequence
<220> FEATURE:
<223> OTHER INFORMATION: Recombinant BC2LCN155cys

<400> SEQUENCE: 32

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
            20                  25                  30

Val Asp Ile Pro Gly Leu Tyr Leu Asp Val Ala Lys Ala Gly Ile Arg
        35                  40                  45

Asp Gly Lys Leu Gln Val Ile Leu Asn Val Pro Thr Pro Tyr Ala Thr
    50                  55                  60

Gly Asn Asn Phe Pro Gly Ile Tyr Phe Ala Ile Ala Thr Asn Gln Gly
65                  70                  75                  80

Val Val Ala Asp Gly Cys Phe Thr Tyr Ser Ser Lys Val Pro Glu Ser
            85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
        115                 120                 125

Met His Ile Asp Ser Tyr Ala Ser Leu Ser Ala Ile Trp Gly Thr Ala
    130                 135                 140

Ala Pro Ser Ser Gln Gly Ser Gly Asn Gln Gly Ala Glu Thr Gly Gly
145                 150                 155                 160

```
Thr Gly Ala Gly Asn Ile Gly Gly Gly Ala Ser Gly Gly Cys
                165                 170

<210> SEQ ID NO 33
<211> LENGTH: 150
<212> TYPE: PRT
<213> ORGANISM: Artificial Sequence
<220> FEATURE:
<223> OTHER INFORMATION: Recombinant BC2LCN129cys

<400> SEQUENCE: 33

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
            20                  25                  30

Val Asp Ile Pro Gly Leu Tyr Leu Asp Val Ala Lys Ala Gly Ile Arg
        35                  40                  45

Asp Gly Lys Leu Gln Val Ile Leu Asn Val Pro Thr Pro Tyr Ala Thr
        50                  55                  60

Gly Asn Asn Phe Pro Gly Ile Tyr Phe Ala Ile Ala Thr Asn Gln Gly
65                  70                  75                  80

Val Val Ala Asp Gly Cys Phe Thr Tyr Ser Ser Lys Val Pro Glu Ser
                85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
            115                 120                 125

Met His Ile Asp Ser Tyr Ala Ser Leu Ser Ala Ile Trp Gly Thr Gly
        130                 135                 140

Gly Gly Ser Gly Gly Cys
145                 150

<210> SEQ ID NO 34
<211> LENGTH: 148
<212> TYPE: PRT
<213> ORGANISM: Artificial Sequence
<220> FEATURE:
<223> OTHER INFORMATION: Recombinant BC2LCN127cys

<400> SEQUENCE: 34

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
            20                  25                  30

Val Asp Ile Pro Gly Leu Tyr Leu Asp Val Ala Lys Ala Gly Ile Arg
        35                  40                  45

Asp Gly Lys Leu Gln Val Ile Leu Asn Val Pro Thr Pro Tyr Ala Thr
        50                  55                  60

Gly Asn Asn Phe Pro Gly Ile Tyr Phe Ala Ile Ala Thr Asn Gln Gly
65                  70                  75                  80

Val Val Ala Asp Gly Cys Phe Thr Tyr Ser Ser Lys Val Pro Glu Ser
                85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
            115                 120                 125

Met His Ile Asp Ser Tyr Ala Ser Leu Ser Ala Ile Trp Gly Gly Gly
```

-continued

```
         130              135              140

Ser Gly Gly Cys
145

<210> SEQ ID NO 35
<211> LENGTH: 150
<212> TYPE: PRT
<213> ORGANISM: Artificial Sequence
<220> FEATURE:
<223> OTHER INFORMATION: Recombinant BC2LCN129G36Ccys

<400> SEQUENCE: 35

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
            20                  25                  30

Val Asp Ile Pro Gly Leu Tyr Leu Asp Val Ala Lys Ala Gly Ile Arg
        35                  40                  45

Asp Cys Lys Leu Gln Val Ile Leu Asn Val Pro Thr Pro Tyr Ala Thr
    50                  55                  60

Gly Asn Asn Phe Pro Gly Ile Tyr Phe Ala Ile Ala Thr Asn Gln Gly
65                  70                  75                  80

Val Val Ala Asp Gly Cys Phe Thr Tyr Ser Ser Lys Val Pro Glu Ser
                85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
        115                 120                 125

Met His Ile Asp Ser Tyr Ala Ser Leu Ser Ala Ile Trp Gly Thr Gly
    130                 135                 140

Gly Gly Ser Gly Gly Cys
145                 150

<210> SEQ ID NO 36
<211> LENGTH: 148
<212> TYPE: PRT
<213> ORGANISM: Artificial Sequence
<220> FEATURE:
<223> OTHER INFORMATION: Recombinant BC2LCN127G36Ccys

<400> SEQUENCE: 36

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
            20                  25                  30

Val Asp Ile Pro Gly Leu Tyr Leu Asp Val Ala Lys Ala Gly Ile Arg
        35                  40                  45

Asp Cys Lys Leu Gln Val Ile Leu Asn Val Pro Thr Pro Tyr Ala Thr
    50                  55                  60

Gly Asn Asn Phe Pro Gly Ile Tyr Phe Ala Ile Ala Thr Asn Gln Gly
65                  70                  75                  80

Val Val Ala Asp Gly Cys Phe Thr Tyr Ser Ser Lys Val Pro Glu Ser
                85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
        115                 120                 125
```

```
Met His Ile Asp Ser Tyr Ala Ser Leu Ser Ala Ile Trp Gly Gly Gly
    130                 135                 140

Ser Gly Gly Cys
145
```

```
<210> SEQ ID NO 37
<211> LENGTH: 140
<212> TYPE: PRT
<213> ORGANISM: Artificial Sequence
<220> FEATURE:
<223> OTHER INFORMATION: Recombinant BC2LCN126

<400> SEQUENCE: 37

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
            20                  25                  30

Val Asp Ile Pro Gly Leu Tyr Leu Asp Val Ala Lys Ala Gly Ile Arg
        35                  40                  45

Asp Gly Lys Leu Gln Val Ile Leu Asn Val Pro Thr Pro Tyr Ala Thr
    50                  55                  60

Gly Asn Asn Phe Pro Gly Ile Tyr Phe Ala Ile Ala Thr Asn Gln Gly
65                  70                  75                  80

Val Val Ala Asp Gly Cys Phe Thr Tyr Ser Ser Lys Val Pro Glu Ser
                85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
        115                 120                 125

Met His Ile Asp Ser Tyr Ala Ser Leu Ser Ala Ile
    130                 135                 140
```

```
<210> SEQ ID NO 38
<211> LENGTH: 150
<212> TYPE: PRT
<213> ORGANISM: Artificial Sequence
<220> FEATURE:
<223> OTHER INFORMATION: Recombinant BC2LCN127E81Ccys

<400> SEQUENCE: 38

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
            20                  25                  30

Val Asp Ile Pro Gly Leu Tyr Leu Asp Val Ala Lys Ala Gly Ile Arg
        35                  40                  45

Asp Gly Lys Leu Gln Val Ile Leu Asn Val Pro Thr Pro Tyr Ala Thr
    50                  55                  60

Gly Asn Asn Phe Pro Gly Ile Tyr Phe Ala Ile Ala Thr Asn Gln Gly
65                  70                  75                  80

Val Val Ala Asp Gly Cys Phe Thr Tyr Ser Ser Lys Val Pro Cys Ser
                85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
        115                 120                 125

Met His Ile Asp Ser Tyr Ala Ser Leu Ser Ala Ile Trp Gly Thr Gly
    130                 135                 140
```

-continued

```
Gly Gly Ser Gly Gly Cys
145                 150

<210> SEQ ID NO 39
<211> LENGTH: 150
<212> TYPE: PRT
<213> ORGANISM: Artificial Sequence
<220> FEATURE:
<223> OTHER INFORMATION: Recombinant BC2LCN127E81Qcys

<400> SEQUENCE: 39

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
            20                  25                  30

Val Asp Ile Pro Gly Leu Tyr Leu Asp Val Ala Lys Ala Gly Ile Arg
        35                  40                  45

Asp Gly Lys Leu Gln Val Ile Leu Asn Val Pro Thr Pro Tyr Ala Thr
        50                  55                  60

Gly Asn Asn Phe Pro Gly Ile Tyr Phe Ala Ile Ala Thr Asn Gln Gly
65                  70                  75                  80

Val Val Ala Asp Gly Cys Phe Thr Tyr Ser Ser Lys Val Pro Gln Ser
                85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
            115                 120                 125

Met His Ile Asp Ser Tyr Ala Ser Leu Ser Ala Ile Trp Gly Thr Gly
        130                 135                 140

Gly Gly Ser Gly Gly Cys
145                 150

<210> SEQ ID NO 40
<211> LENGTH: 150
<212> TYPE: PRT
<213> ORGANISM: Artificial Sequence
<220> FEATURE:
<223> OTHER INFORMATION: Recombinant BC2LCN127E81Hcys

<400> SEQUENCE: 40

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
            20                  25                  30

Val Asp Ile Pro Gly Leu Tyr Leu Asp Val Ala Lys Ala Gly Ile Arg
        35                  40                  45

Asp Gly Lys Leu Gln Val Ile Leu Asn Val Pro Thr Pro Tyr Ala Thr
        50                  55                  60

Gly Asn Asn Phe Pro Gly Ile Tyr Phe Ala Ile Ala Thr Asn Gln Gly
65                  70                  75                  80

Val Val Ala Asp Gly Cys Phe Thr Tyr Ser Ser Lys Val Pro His Ser
                85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
            115                 120                 125

Met His Ile Asp Ser Tyr Ala Ser Leu Ser Ala Ile Trp Gly Thr Gly
```

```
                130             135             140

Gly Gly Ser Gly Gly Cys
145                 150

<210> SEQ ID NO 41
<211> LENGTH: 150
<212> TYPE: PRT
<213> ORGANISM: Artificial Sequence
<220> FEATURE:
<223> OTHER INFORMATION: Recombinant BC2LCN127E81Mcys

<400> SEQUENCE: 41

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
                20                  25                  30

Val Asp Ile Pro Gly Leu Tyr Leu Asp Val Ala Lys Ala Gly Ile Arg
            35                  40                  45

Asp Gly Lys Leu Gln Val Ile Leu Asn Val Pro Thr Pro Tyr Ala Thr
        50                  55                  60

Gly Asn Asn Phe Pro Gly Ile Tyr Phe Ala Ile Ala Thr Asn Gln Gly
65                  70                  75                  80

Val Val Ala Asp Gly Cys Phe Thr Tyr Ser Ser Lys Val Pro Met Ser
                85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
        115                 120                 125

Met His Ile Asp Ser Tyr Ala Ser Leu Ser Ala Ile Trp Gly Thr Gly
        130                 135                 140

Gly Gly Ser Gly Gly Cys
145                 150

<210> SEQ ID NO 42
<211> LENGTH: 148
<212> TYPE: PRT
<213> ORGANISM: Artificial Sequence
<220> FEATURE:
<223> OTHER INFORMATION: Recombinant BC2LCN127C72Gcys

<400> SEQUENCE: 42

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
                20                  25                  30

Val Asp Ile Pro Gly Leu Tyr Leu Asp Val Ala Lys Ala Gly Ile Arg
            35                  40                  45

Asp Gly Lys Leu Gln Val Ile Leu Asn Val Pro Thr Pro Tyr Ala Thr
        50                  55                  60

Gly Asn Asn Phe Pro Gly Ile Tyr Phe Ala Ile Ala Thr Asn Gln Gly
65                  70                  75                  80

Val Val Ala Asp Gly Gly Phe Thr Tyr Ser Ser Lys Val Pro Glu Ser
                85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
        115                 120                 125
```

```
Met His Ile Asp Ser Tyr Ala Ser Leu Ser Ala Ile Trp Gly Gly Gly
    130                 135                 140

Ser Gly Gly Cys
145

<210> SEQ ID NO 43
<211> LENGTH: 148
<212> TYPE: PRT
<213> ORGANISM: Artificial Sequence
<220> FEATURE:
<223> OTHER INFORMATION: Recombinant BC2LCN127C72Acys

<400> SEQUENCE: 43

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
            20                  25                  30

Val Asp Ile Pro Gly Leu Tyr Leu Asp Val Ala Lys Ala Gly Ile Arg
        35                  40                  45

Asp Gly Lys Leu Gln Val Ile Leu Asn Val Pro Thr Pro Tyr Ala Thr
    50                  55                  60

Gly Asn Asn Phe Pro Gly Ile Tyr Phe Ala Ile Ala Thr Asn Gln Gly
65                  70                  75                  80

Val Val Ala Asp Gly Ala Phe Thr Tyr Ser Ser Lys Val Pro Glu Ser
            85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
            115                 120                 125

Met His Ile Asp Ser Tyr Ala Ser Leu Ser Ala Ile Trp Gly Gly Gly
    130                 135                 140

Ser Gly Gly Cys
145

<210> SEQ ID NO 44
<211> LENGTH: 148
<212> TYPE: PRT
<213> ORGANISM: Artificial Sequence
<220> FEATURE:
<223> OTHER INFORMATION: Recombinant BC2LCN127Q39Lcys

<400> SEQUENCE: 44

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
            20                  25                  30

Val Asp Ile Pro Gly Leu Tyr Leu Asp Val Ala Lys Ala Gly Ile Arg
        35                  40                  45

Asp Gly Lys Leu Leu Val Ile Leu Asn Val Pro Thr Pro Tyr Ala Thr
    50                  55                  60

Gly Asn Asn Phe Pro Gly Ile Tyr Phe Ala Ile Ala Thr Asn Gln Gly
65                  70                  75                  80

Val Val Ala Asp Gly Cys Phe Thr Tyr Ser Ser Lys Val Pro Glu Ser
            85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
            115                 120                 125
```

```
Met His Ile Asp Ser Tyr Ala Ser Leu Ser Ala Ile Trp Gly Gly Gly
    130                 135                 140

Ser Gly Gly Cys
145

<210> SEQ ID NO 45
<211> LENGTH: 148
<212> TYPE: PRT
<213> ORGANISM: Artificial Sequence
<220> FEATURE:
<223> OTHER INFORMATION: Recombinant BC2LCN127Q39Mcys

<400> SEQUENCE: 45

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
            20                  25                  30

Val Asp Ile Pro Gly Leu Tyr Leu Asp Val Ala Lys Ala Gly Ile Arg
        35                  40                  45

Asp Gly Lys Leu Met Val Ile Leu Asn Val Pro Thr Pro Tyr Ala Thr
    50                  55                  60

Gly Asn Asn Phe Pro Gly Ile Tyr Phe Ala Ile Ala Thr Asn Gln Gly
65                  70                  75                  80

Val Val Ala Asp Gly Cys Phe Thr Tyr Ser Ser Lys Val Pro Glu Ser
                85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
        115                 120                 125

Met His Ile Asp Ser Tyr Ala Ser Leu Ser Ala Ile Trp Gly Gly Gly
    130                 135                 140

Ser Gly Gly Cys
145

<210> SEQ ID NO 46
<211> LENGTH: 148
<212> TYPE: PRT
<213> ORGANISM: Artificial Sequence
<220> FEATURE:
<223> OTHER INFORMATION: Recombinant BC2LCN127Q39L/C72Gcys

<400> SEQUENCE: 46

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
            20                  25                  30

Val Asp Ile Pro Gly Leu Tyr Leu Asp Val Ala Lys Ala Gly Ile Arg
        35                  40                  45

Asp Gly Lys Leu Leu Val Ile Leu Asn Val Pro Thr Pro Tyr Ala Thr
    50                  55                  60

Gly Asn Asn Phe Pro Gly Ile Tyr Phe Ala Ile Ala Thr Asn Gln Gly
65                  70                  75                  80

Val Val Ala Asp Gly Gly Phe Thr Tyr Ser Ser Lys Val Pro Glu Ser
                85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
```

-continued

```
            115             120             125

Met His Ile Asp Ser Tyr Ala Ser Leu Ser Ala Ile Trp Gly Gly Gly
    130             135             140

Ser Gly Gly Cys
145

<210> SEQ ID NO 47
<211> LENGTH: 148
<212> TYPE: PRT
<213> ORGANISM: Artificial Sequence
<220> FEATURE:
<223> OTHER INFORMATION: Recombinant BC2LCN127Q39L/Q65L/C72Gcys

<400> SEQUENCE: 47

Met Gly Ser Ser His His His His His His Ser Trp Ser Ser Pro Leu
1               5                   10                  15

Leu Ser Ala Ser Ile Val Ser Ala Pro Val Val Thr Ser Glu Thr Tyr
                20                  25                  30

Val Asp Ile Pro Gly Leu Tyr Leu Asp Val Ala Lys Ala Gly Ile Arg
            35                  40                  45

Asp Gly Lys Leu Leu Val Ile Leu Asn Val Pro Thr Pro Tyr Ala Thr
        50                  55                  60

Gly Asn Asn Phe Pro Gly Ile Tyr Phe Ala Ile Ala Thr Asn Leu Gly
65                  70                  75                  80

Val Val Ala Asp Gly Gly Phe Thr Tyr Ser Ser Lys Val Pro Glu Ser
                85                  90                  95

Thr Gly Arg Met Pro Phe Thr Leu Val Ala Thr Ile Asp Val Gly Ser
            100                 105                 110

Gly Val Thr Phe Val Lys Gly Gln Trp Lys Ser Val Arg Gly Ser Ala
        115                 120                 125

Met His Ile Asp Ser Tyr Ala Ser Leu Ser Ala Ile Trp Gly Gly Gly
    130             135             140

Ser Gly Gly Cys
145

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
taatacgact cactataggg                                               20

<210> SEQ ID NO 49
<211> LENGTH: 39
<212> TYPE: DNA
<213> ORGANISM: Artificial Sequence
<220> FEATURE:
<223> OTHER INFORMATION: primer

<400> SEQUENCE: 49
accgccagaa ccaccaccgg tgccccaaat cgccgaaag                           39

<210> SEQ ID NO 50
<211> LENGTH: 36
<212> TYPE: DNA
<213> ORGANISM: Artificial Sequence
<220> FEATURE:
<223> OTHER INFORMATION: primer
```

<400> SEQUENCE: 50
agctgactcg agtcagcaac cgccagaacc accacc                                     36

<210> SEQ ID NO 51
<211> LENGTH: 40
<212> TYPE: DNA
<213> ORGANISM: Artificial Sequence
<220> FEATURE:
<223> OTHER INFORMATION: primer

<400> SEQUENCE: 51
accgccagaa ccaccacccc aaatcgccga aaggctcgcg                                 40

<210> SEQ ID NO 52
<211> LENGTH: 32
<212> TYPE: DNA
<213> ORGANISM: Artificial Sequence
<220> FEATURE:
<223> OTHER INFORMATION: primer

<400> SEQUENCE: 52
gtagcaaact gcagtttgca atcacgaatc cc                                         32

<210> SEQ ID NO 53
<211> LENGTH: 38
<212> TYPE: DNA
<213> ORGANISM: Artificial Sequence
<220> FEATURE:
<223> OTHER INFORMATION: primer

<400> SEQUENCE: 53
tgctagctcg agctaaatcg ccgaaaggct cgcgtagc                                   38

<210> SEQ ID NO 54
<211> LENGTH: 19
<212> TYPE: DNA
<213> ORGANISM: Artificial Sequence
<220> FEATURE:
<223> OTHER INFORMATION: primer

<400> SEQUENCE: 54
gctagttatt gctcagcgg                                                        19

<210> SEQ ID NO 55
<211> LENGTH: 36
<212> TYPE: DNA
<213> ORGANISM: Artificial Sequence
<220> FEATURE:
<223> OTHER INFORMATION: primer

<400> SEQUENCE: 55
ctctatccgg taccgtgaag cacggggcgt atgccg                                     36

<210> SEQ ID NO 56
<211> LENGTH: 36
<212> TYPE: DNA
<213> ORGANISM: Artificial Sequence
<220> FEATURE:
<223> OTHER INFORMATION: primer

<400> SEQUENCE: 56
ctctatccgg taccgcagag cacggggcgt atgccg                                     36

<210> SEQ ID NO 57

<211> LENGTH: 36
<212> TYPE: DNA
<213> ORGANISM: Artificial Sequence
<220> FEATURE:
<223> OTHER INFORMATION: primer

<400> SEQUENCE: 57
ctctatccgg taccgcatag cacggggcgt atgccg                                    36

<210> SEQ ID NO 58
<211> LENGTH: 36
<212> TYPE: DNA
<213> ORGANISM: Artificial Sequence
<220> FEATURE:
<223> OTHER INFORMATION: primer

<400> SEQUENCE: 58
ctctatccgg taccgatgag cacggggcgt atgccg                                    36

<210> SEQ ID NO 59
<211> LENGTH: 38
<212> TYPE: DNA
<213> ORGANISM: Artificial Sequence
<220> FEATURE:
<223> OTHER INFORMATION: primer

<400> SEQUENCE: 59
ccaaggtacc ttggagctat aggtaaaccc gccatccg                                  38

<210> SEQ ID NO 60
<211> LENGTH: 38
<212> TYPE: DNA
<213> ORGANISM: Artificial Sequence
<220> FEATURE:
<223> OTHER INFORMATION: primer

<400> SEQUENCE: 60
ccaaggtacc ttggagctat aggtaaaggc gccatccg                                  38

<210> SEQ ID NO 61
<211> LENGTH: 36
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: b is c, g, or t

<400> SEQUENCE: 61
ctctatccgg taccgnnbag cacggggcgt atgccg                                    36

<210> SEQ ID NO 62
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(28)
<223> OTHER INFORMATION: v is a, c, or g
<220> FEATURE:
<221> NAME/KEY: misc_feature
<222> LOCATION: (29)..(30)
<223> OTHER INFORMATION: n is a, c, g, or t

<400> SEQUENCE: 62
ccaaggtacc ttggagctat aggtaaavnn gccatccg                              38

<210> SEQ ID NO 63
<211> LENGTH: 494
<212> TYPE: DNA
<213> ORGANISM: Artificial Sequence
<220> FEATURE:
<223> OTHER INFORMATION: DNA coding for BC2LCN127Q39Lcys

<400> SEQUENCE: 63
tctagaaata attttgttta actttaagaa ggagatatac catgggcagc agccatcatc      60
atcatcatca cagctggagc tcgccccttt tgagcgcaag cattgtcagc gcaccggttg     120
tgacctccga aacctatgtg gatataccgg gcctgtatct ggatgtggcg aaagcgggga    180
ttcgtgatgg caaactgctg gtgattctga atgtgccgac cccgtatgcg accggcaaca    240
actttccggg aatttacttt gcgattgcga ccaatcaggg cgttgtggcg gatggctgtt    300
ttacctatag ctccaaggta ccggagagca cggggcgtat gccgtttacc ttggtggcga    360
ccattgatgt gggctcgggc gtgaccttcg tgaaaggcca gtggaaatca gtgcggggca    420
gcgcgatgca tattgatagc tacgcgagcc tttcggcgat ttggggtggt ggttctggcg    480
gttgctgact cgag                                                      494

<210> SEQ ID NO 64
<211> LENGTH: 494
<212> TYPE: DNA
<213> ORGANISM: Artificial Sequence
<220> FEATURE:
<223> OTHER INFORMATION: DNA coding for BC2LCN127Q39L/C72Gcys

<400> SEQUENCE: 64
tctagaaata attttgttta actttaagaa ggagatatac catgggcagc agccatcatc      60
atcatcatca cagctggagc tcgccccttt tgagcgcaag cattgtcagc gcaccggttg     120
tgacctccga aacctatgtg gatataccgg gcctgtatct ggatgtggcg aaagcgggga    180
ttcgtgatgg caaactgctg gtgattctga atgtgccgac cccgtatgcg accggcaaca    240
actttccggg aatttacttt gcgattgcga ccaatcaggg cgttgtggcg gatggcggtt    300
ttacctatag ctccaaggta ccggagagca cggggcgtat gccgtttacc ttggtggcga    360
ccattgatgt gggctcgggc gtgaccttcg tgaaaggcca gtggaaatca gtgcggggca    420
gcgcgatgca tattgatagc tacgcgagcc tttcggcgat ttggggtggt ggttctggcg    480
gttgctgact cgag                                                      494

<210> SEQ ID NO 65
<211> LENGTH: 494
<212> TYPE: DNA
<213> ORGANISM: Artificial Sequence
<220> FEATURE:
<223> OTHER INFORMATION: DNA coding for BC2LCN127Q39L/Q65L/C72Gcys

<400> SEQUENCE: 65
tctagaaata attttgttta actttaagaa ggagatatac catgggcagc agccatcatc      60
atcatcatca cagctggagc tcgccccttt tgagcgcaag cattgtcagc gcaccggttg     120
tgacctccga aacctatgtg gatataccgg gcctgtatct ggatgtggcg aaagcgggga    180

-continued

```
ttcgtgatgg caaactgctg gtgattctga atgtgccgac cccgtatgcg accggcaaca      240
actttccggg aatttacttt gcgattgcga ccaatctggg cgttgtggcg gatggcggtt      300
ttacctatag ctccaaggta ccggagagca cggggcgtat gccgtttacc ttggtggcga      360
ccattgatgt gggctcgggc gtgaccttcg tgaaaggcca gtggaaatca gtgcggggca      420
gcgcgatgca tattgatagc tacgcgagcc tttcggcgat ttggggtggt ggttctggcg      480
gttgctgact cgag                                                        494
```

```
<210> SEQ ID NO 66
<211> LENGTH: 5
<212> TYPE: PRT
<213> ORGANISM: Artificial Sequence
<220> FEATURE:
<223> OTHER INFORMATION: oligopeptide

<400> SEQUENCE: 66

Ala Ser Gly Gly Cys
1               5

<210> SEQ ID NO 67
<211> LENGTH: 7
<212> TYPE: PRT
<213> ORGANISM: Artificial Sequence
<220> FEATURE:
<223> OTHER INFORMATION: oligopeptide

<400> SEQUENCE: 67

Gly Gly Gly Ser Gly Gly Cys
1               5
```